United States Patent [19]
Murphy et al.

[11] Patent Number: 5,750,400
[45] Date of Patent: *May 12, 1998

[54] CODING SEQUENCES OF THE HUMAN BRCA1 GENE

[75] Inventors: Patricia D. Murphy, Slingerland, N.Y.; Antonette C. Allen, Severn, Md.; Christopher P. Alvares, Potomac, Md.; Brenda S. Critz, Frederick, Md.; Sheri J. Olson, Arlington, Va.; Denise B. Schelter, Silver Spring; Bin Zeng, Rockville, both of Md.

[73] Assignee: OncorMed, Inc., Gaithersburg, Md.

[*] Notice: The term of this patent shall not extend beyond the expiration date of Pat. No. 5,654,155.

[21] Appl. No.: 798,691

[22] Filed: Feb. 12, 1997

Related U.S. Application Data

[62] Division of Ser. No. 598,591, Feb. 12, 1996, Pat. No. 5,654,155.

[51] Int. Cl.$^6$ .................. C12Q 1/68; C12P 19/34; C07H 21/04; C07H 21/02
[52] U.S. Cl. .......... 435/6; 435/91.2; 435/91.1; 435/91.21; 536/23.1; 536/23.5; 536/24.3; 536/24.33
[58] Field of Search ............. 435/6, 91.2, 91.1, 435/91.21; 536/23.1, 24.3, 24.33, 23.5

[56] References Cited

U.S. PATENT DOCUMENTS 4,458,066 7/1984 Caruthers et al. ............ 536/25.34
5,693,473 12/1997 Shattuck-Eidens et al. ............ 435/6

FOREIGN PATENT DOCUMENTS 0705903 10/1996 European Pat. Off. .

OTHER PUBLICATIONS

Holt, et al., Gene Therapy Protocol ORDA #: 9603-149 ORDA approved Protocol for BRCA1 Gene Therapy, pp. 1003-1030 (1995).
Arteaga, et al., "Tissue-Targeted Antisense c-fos Retroviral Vector Inhibits Established Breast Cancer Xenografts in Nude Mice", Cancer Research 56:1098-1103 (1996).
Beaucage, et al., "Deoxynucleoside Phosphoramidites-A New Class of Key Intermediates for Deoxypolynucleotide Synthesis", Tetrahedron Letters 22(20): 1859-1662 (1991).
Beaudet, et al., "A Suggested Nomenclature for Designating Mutations", Human Mutation 2:245-248 (1993).
Conner, et al., "Detection of Sickle Cell β-globin Allele by Hybridization with Synthetic Oligonucleotides", Proc. Natl. Acad. Sci. 80:278-282 (1983).
Easton, et al., "Breast and Ovarian Cancer Incidence in BRCA1-Mutation Carriers", American Journal of Human Genetics 56:265-271 (1995).
Friedman, et al., "Confirmation of BRCA1 by Analysis of Germline Mutations Linked to Breast and Ovarian Cancer in Ten Families", Nature Genetics 8:399-404 (1994).
Friend, et al., Breast Cancer Information on the Web Nature Genetics 11:238 (1995).
Holt, et al., "Growth Retardation and Tumor Inhibition by BRCA1", Nature Genetics 12:298-302 (1996).
Hoskins, et al., "Assessment and Counseling for Women With a Family History of Breast Cancer", JAMA, 273(7):577-585 (1995).
Jensen, et al., "BRCA1 is Secreted and Exhibits Properties of a Granin", Nature Genetics 12:303-308 (1996).
Landgren, et al., "A Ligase-Mediated Gene Detection Technique", Science 241:1007-1021 (1988).
Landgren, et al., "DNA Diagnostics-Molecular Techniques and Automation", Science 242:229-237 (1988).
Miki, Y. et al., "A Strong Candidate for the Breast and Ovarian Cancer Susceptibility Gene BRCA1", Science 266:66-71 (1994).
Rowell, S., et al., "Inherited Predisposition to Breast and Ovarian Cancer", American Journal of Human Genetics 55:861-865 (1994).
Steeg, "Granin Expectations in Breast Cancer?", Nature Genetics 12:223-225 (1996).
Thompson, et al., "Decreased Expression of BRCA1 Accelerates Growth and is Often Present During Sporadic Breast Cancer Progression", Nature Genetics 9:444-450 (1995).
Maniatis, et al., "Isolation of High-Molecular-Weight, Eukaryotic DNA from Cells Grown in Tissue Culture," Molecular Cloning: A Laboratory Manual Cold Spring Harbor, NY pp. 280-281 (1982).
Copy of cover page and first two pages of book—PCR. A Practical Approach, ILR Press, Eds. M.J. McPherson, P. Quirke, and G. R. Taylor (1992), 2 pages.
Saiki, et al., "A Novel Method for the Detection of Polymorphic Restriction Sites by Cleavage of Oligonucleotide Probes: Application to Sickle-Cell Anemia," Bio/Technology 3:1008-1012 (1985).
Database Genbank, Accession No. U14680, 1994.

Primary Examiner—Sheela Huff
Attorney, Agent, or Firm—Albert P. Halluin; R. Thomas Gallegos; Howrey & Simon

[57] ABSTRACT

This invention is directed to three coding sequences of the BRCA1 gene. The three coding sequences, BRCA1$^{(omi1)}$, BRCA1$^{(omi2)}$ and BRCA1$^{(omi3)}$ as well as their frequencies of occurrence are provided together with the protein sequences they code for. Another aspect of this invention is a method of determining the consensus sequence for any gene. Another aspect of the invention is a method of identifying an individual having an increased genetic susceptibility to breast or ovarian cancer because they have inherited a causative mutation in their BRCA1 gene. This invention is also related to a method of performing gene therapy with any of the isolated BRCA1 coding sequences.

8 Claims, 1 Drawing Sheet

CODING SEQUENCES OF THE HUMAN BRCA1 GENE

This application is a Continuation-In Part of U.S. application Ser. No. 08/598,591 filed on Feb. 12, 1996, now patented U.S. Pat. No. 5,654,155.

FIELD OF THE INVENTION

This invention relates to a gene which has been associated with breast and ovarian cancer where the gene is found to be mutated. More specifically, this invention relates to the three coding sequences of the BRCA1 gene BRCA1$^{(omi1)}$, BRCA1$^{(omi2)}$, and BRCA1$^{(omi3)}$) isolated from human subjects.

BACKGROUND OF THE INVENTION

It has been estimated that about 5–10% of breast cancer is inherited Rowell, S., et al., *American Journal of Human Genetics* 55:861–865 (1994). Located on chromosome 17, BRCA1 is the first gene identified to be conferring increased risk for breast and ovarian cancer. Miki et al., *Science* 266:66–71 (1994). Mutations in this "tumor suppressor" gene are thought to account for roughly 45% of inherited breast cancer and 80–90% of families with increased risk of early onset breast and ovarian cancer. Easton et al., *American Journal of Human Genetics* 52:678–701 (1993).

Locating one or more mutations in the BRCA1 region of chromosome 17 provides a promising approach to reducing the high incidence and mortality associated with breast and ovarian cancer through the early detection of women at high risk. These women, once identified, can be targeted for more aggressive prevention programs. Screening is carried out by a variety of methods which include karyotyping, probe binding and DNA sequencing.

In DNA sequencing technology, genomic DNA is extracted from whole blood and the coding sequences of the BRCA1 gene are amplified. The coding sequences might be sequenced completely and the results are compared to the DNA sequence of the gene. Alternatively, the coding sequence of the sample gene may be compared to a panel of known mutations before completely sequencing the gene and comparing it to a normal sequence of the gene.

If a mutation in the BRCA1 coding sequence is found, it may be possible to provide the individual with increased expression of the gene through gene transfer therapy. It has been demonstrated that the gene transfer of the BRCA1 coding sequence into cancer cells inhibits their growth and reduces tumorigenesis of human cancer cells in nude mice. Jeffrey Holt and his colleagues conclude that the product of BRCA1 expression is a secreted tumor growth inhibitor, making BRCA1 an ideal gene for gene therapy studies. Transduction of only a moderate percentage of tumor cells apparently produces enough growth inhibitor to inhibit all tumor cells. Arteaga, C L, and J T Holt *Cancer Research* 56: 1098–1103 (1996), Holt, J T et al., *Nature Genetics* 12: 298–302 (1996).

The observation of Holt et al. that the BRCA1 growth inhibitor is a secreted protein leads to the possible use of injection of the growth inhibitor into the area of the tumor for tumor suppression.

The BRCA1 gene is divided into 24 separate exons. Exons 1 and 4 are noncoding, in that they are not part of the final functional BRCA1 protein product. The BRCA1 coding sequence spans roughly 5600 base pairs (bp). Each exon consists of 200–400 bp, except for exon 11 which contains about 3600 bp. To sequence the coding sequence of the BRCA1 gene, each exon is amplified separately and the resulting PCR products are sequenced in the forward and reverse directions. Because exon 11 is so large, we have divided it into twelve overlapping PCR fragments of roughly 350 bp each (segments "A" through "L" of BRCA1 exon 11).

Many mutations and polymorphisms have already been reported in the BRCA1 gene. A world wide web site has been built to facilitate the detection and characterization of alterations in breast cancer susceptibility genes. Such mutations in BRCA1 can be accessed through the Breast Cancer Information Core at: http://www.nchgr.nih.gov/dir/lab_transfer/bic. This data site became publicly available on Nov. 1, 1995. Friend, S. et al. *Nature Genetics* 11:238, (1995).

The genetics of Breast/Ovarian Cancer Syndrome is autosomal dominant with reduced penetrance. In simple terms, this means that the syndrome runs through families such that both sexes can be carriers (only women get the disease but men can pass it on), all generations will likely have breast/ovarian or both diseases and sometimes in the same individual, occasionally women carriers either die young before they have the time to manifest disease (and yet offspring get it) or they never develop breast or ovarian cancer and die of old age (the latter people are said to have "reduced penetrance" because they never develop cancer). Pedigree analysis and genetic counseling is absolutely essential to the proper workup of a family prior to any lab work.

Until now, only a single coding sequence for the BRCA1 gene has been available for comparison to patient samples. That sequence is available as GenBank Accession Number U14680. There is a need in the art, therefore, to have available a coding sequence which is the BRCA1 coding sequence found in the majority of the population, a "consensus coding sequence", BRCA1$^{(omi1)}$ Seq. ID. NO. 1. A consensus coding sequence will make it possible for true mutations to be easily identified or differentiated from polymorphisms. Identification of mutations of the BRCA1 gene and protein would allow more widespread diagnostic screening for hereditary breast and ovarian cancer than is currently possible. Two additional coding sequences have been isolated and characterize. The BRCA1$^{(omi2)}$ SEQ. ID. NO.: 3, and BRCA1$^{(omi3)}$ SEQ. ID. NO.:5 coding sequences also have utility in diagnosis, gene therapy and in making therapeutic BRCA1 protein.

A coding sequence of the BRCA1 gene which occurs most commonly in the human gene pool is provided. The most commonly occurring coding sequence more accurately reflects the most likely sequence to be found in a subject. Use of the coding sequence BRCA1$^{(omi1)}$ SEQ. ID. NO.: 1, rather than the previously published BRCA1 sequence, will reduce the likelihood of misinterpreting a "sequence variation" found in the population (i.e. polymorphism) with a pathologic "mutation" (i.e. causes disease in the individual or puts the individual at a high risk of developing the disease). With large interest in breast cancer predisposition testing, misinterpretation is particularly worrisome. People who already have breast cancer are asking the clinical question: "is my disease caused by a heritable genetic mutation?" The relatives of the those with breast cancer are asking the question: "Am I also a carrier of the mutation my relative has? Thus, is my risk increased, and should I undergo a more aggressive surveillance program."

SUMMARY OF THE INVENTION

The present invention is based on the isolation of three coding sequences of the BRCA1 gene found in human individuals.

It is an object of the invention to provide the most commonly occurring coding sequence of the BRCA1 gene.

It is another object of this invention to provide two other coding sequences of BRCA1 gene.

It is another object of the invention to provide three protein sequences coded for by three of the coding sequences of the BRCA1 gene.

It is another object of the invention to provide a list of the codon pairs which occur at each of seven polymorphic points on the BRCA1 gene.

It is another object of the invention to provide the rates of occurrence for the codons.

It is another object of the invention to provide a method wherein BRCA1, or parts thereof, is amplified with one or more oligonucleotide primers.

It is another object of this invention to provide a method of identifying individuals who carry no mutation(s) of the BRCA1 coding sequence and therefore have no increased genetic susceptibility to breast or ovarian cancer based on their BRCA1 genes.

It is another object of this invention to provide a method of identifying a mutation leading to an increased genetic susceptibility to breast or ovarian cancer.

There is a need in the art for a sequence of the BRCA1 gene and for the protein sequence of BRCA1 as well as for an accurate list of codons which occur at polymorphic points on a sequence.

A person skilled in the art of genetic susceptibility testing will find the present invention useful for:

a) identifying individuals having a BRCA1 gene with no coding mutations, who therefore cannot be said to have an increased genetic susceptibility to breast or ovarian cancer from their BRCA1 genes;

b) avoiding misinterpretation of polymorphisms found in the BRCA1 gene;

c) determining the presence of a previously unknown mutation in the BRCA1 gene.

d) identifying a mutation which increases the genetic susceptibility to breast or ovarian cancer.

e) probing a human sample of the BRCA1 gene.

f) performing gene therapy.

g) for making a functioning tumor growth inhibitor protein coded for by one of the BRCA1$^{omi}$ genes.

DETAILED DESCRIPTION OF THE INVENTION

DEFINITIONS

Figure 1:
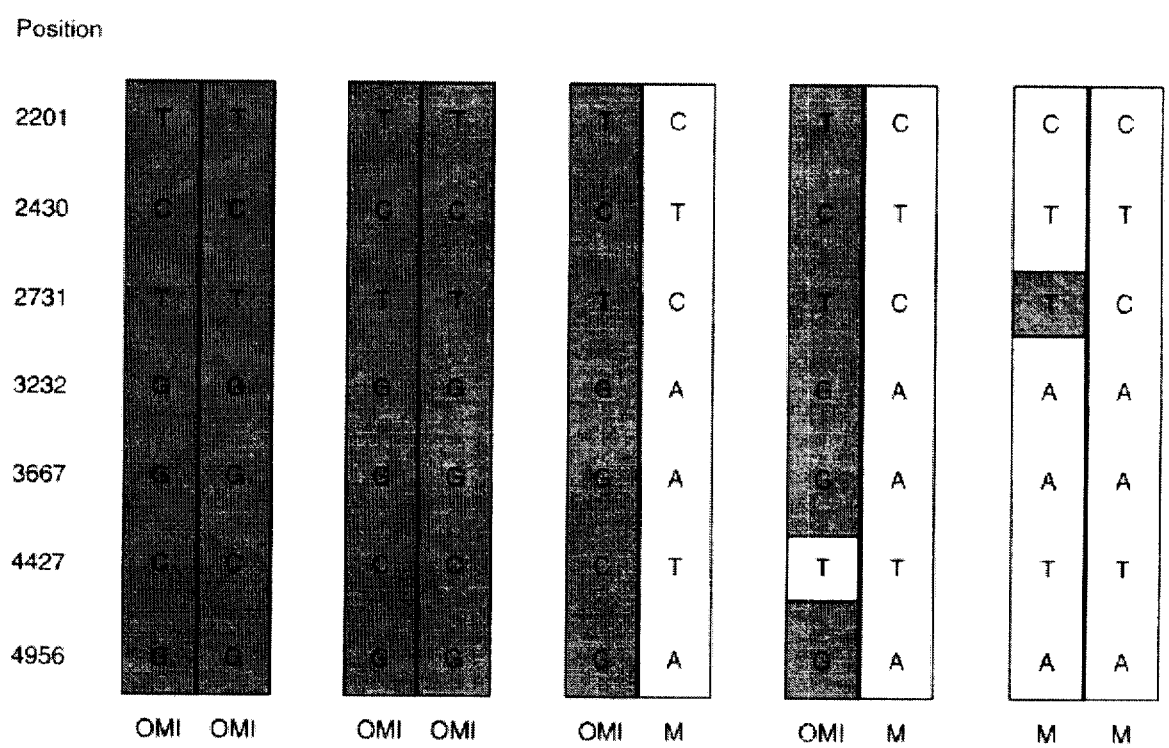
As shown in FIG. 1, the alternative alleles at polymorphic (non-mutation causing variations) sites along a chromosome can be represented as a "haplotype" within a gene such as BRCA1. The BRCA1$^{(omi1)}$ haplotype is shown in FIG. 1 with dark shading (encompassing the alternative alleles found at nucleotide sites 2201, 2430, 2731, 3232, 3667, 4427, and 4956). For comparison, the haplotype that is in GenBank is shown with no shading. As can be seen from the figure, the common "consensus" haplotype is found intact in five separate chromosomes labeled with the OMI symbol (numbers 1-5 from left to right). Two additional haplotypes (BRCA1$^{(omi2)}$, and BRCA1$^{(omi3)}$) are represented with mixed dark and light shading (numbers 7 and 9 from left to right). In total, 7 of 10 haplotypes along the BRCA1 gene are unique.

The following definitions are provided for the purpose of understanding this invention.

"Breast and Ovarian cancer" is understood by those skilled in the art to include breast and ovarian cancer in women and also breast and prostate cancer in men. BRCA1 is associated genetic susceptibility to inherited breast and ovarian cancer in women and also breast and prostate cancer in men. Therefore, claims in this document which recite breast and/or ovarian cancer refer to breast, ovarian and prostate cancers in men and women.

"Coding sequence" or "DNA coding sequence" refers to those portions of a gene which, taken together, code for a peptide (protein), or which nucleic acid itself has function.

"Protein" or "peptide" refers to a sequence amino acids which has function.

"BRCA1$^{(omi)}$" refers collectively to the "BRCA1$^{(omi1)}$", "BRCA1$^{(omi2)}$" and "BRCA1$^{(omi3)}$" coding sequences.

"BRCA1$^{(omi1)}$" refers to SEQ. ID. NO.: 1, a coding sequence for the BRCA1 gene. The coding sequence was found by end to end sequencing of BRCA1 alleles from individuals randomly drawn from a Caucasian population found to have no family history of breast or ovarian cancer. The sequenced gene was found not to contain any mutations. BRCA1$^{(omi1)}$ was determined to be a consensus sequence by calculating the frequency with which the coding sequence occurred among the sample alleles sequenced.

"BRCA1$^{(omi2)}$" and "BRCA1$^{(omi3)}$" refer to SEQ. ID. NO.: 3, and SEQ. ID. NO.: 5 respectively. They are two additional coding sequences for the BRCA1 gene which were also isolated from individuals randomly drawn from a Caucasian population found to have no family history of breast or ovarian cancer.

"Primer" as used herein refers to a sequence comprising about 20 or more nucleotides of the BRCA1 gene.

"Genetic susceptibility" refers to the susceptibility to breast or ovarian cancer due to the presence of a mutation in the BRCA1 gene.

A "target polynucleotide" refers to the nucleic acid sequence of interest e.g., the BRCA1 encoding polynucleotide. Other primers which can be used for primer hybridization will be known or readily ascertainable to those of skill in the art.

"Consensus" means the most commonly occurring in the population.

"Consensus genomic sequence" means the allele of the target gene which occurs with the greatest frequency in a population of individuals having no family history of disease associated with the target gene.

"Substantially complementary to" refers to a probe or primer sequences which hybridize to the sequences provided under stringent conditions and/or sequences having sufficient homology with BRCA1 sequences, such that the allele specific oligonucleotide probe or primers hybridize to the BRCA1 sequences to which they are complimentary.

"Haplotype" refers to a series of alleles within a gene on a chromosome.

"Isolated" as used herein refers to substantially free of other nucleic acids, proteins, lipids, carbohydrates or other materials with which they may be associated. Such association is typically either in cellular material or in a synthesis medium.

"Mutation" refers to a base change or a gain or loss of base pair(s) in a DNA sequence, which results in a DNA sequence which codes for a non-functioning protein or a protein with substantially reduced or altered function.

"Polymorphism" refers to a base change which is not associated with known pathology.

"Tumor growth inhibitor protein" refers to the protein coded for by the BRCA1 gene. The functional protein is thought to suppress breast and ovarian tumor growth.

One embodiment of the invention is an isolated consensus DNA sequence of the BRCA1 coding sequence as set forth in SEQ. ID. NO.: 1.

A further embodiment of the invention is a consensus protein sequence of The BRCA1 protein as set forth in SEQ. ID. NO.: 2.

A further embodiment of the invention is an isolated coding sequence of the BRCA1 gene as set forth in SEQ. ID. NO.: 3.

A further embodiment of the invention is a protein sequence of the BRCA1 protein as set forth in SEQ. ID. NO.: 4.

A further embodiment of the invention is an isolated coding sequence of the BRCA1 gene as set forth in SEQ. ID. NO.: 5.

A further embodiment of the invention is a protein sequence of the BRCA1 protein as set forth in SEQ. ID. NO.: 6.

A further embodiment of the invention is a BRCA1 gene with a BRCA1 coding sequence not associated with breast or ovarian cancer which comprises an alternative pair of codons, AGC and AGT, which occur at position 2201 at frequencies of about 35–45%, and from about 55–65%, respectively.

A further embodiment of the invention is a BRCA1 gene with a BRCA1 coding sequence not associated with breast or ovarian cancer which comprises an alternative pair of codons, AGC and AGT, which occur at position 2201 at frequencies of about 40%, and from about 55–65%, respectively.

A further embodiment of the invention is a set of at least two alternative codon pairs which occur at polymorphic positions in a BRCA1 gene with a BRCA1 coding sequence not associated with breast or ovarian cancer, wherein codon pairs are selected from the group consisting of:

(1) AGC and AGT at position 2201;
(2) TTG and CTG at position 2430;
(3) CCG and CTG at position 2731;
(4) GAA and GGA at position 3232;
(5) AAA and AGA at position 3667;
(6) TCT and TCC at position 4427; and
(7) AGT and GGT at position 4956.

A further embodiment of the invention is a set of at least two alternative codon pairs from the group of alternative codon pairs which occur at polymorphic positions in a BRCA1 gene with a BRCA1 coding sequence not associated with breast or ovarian cancer as recited above, wherein the codon pairs occur in the following frequencies, respectively, in a population of individuals free of disease:

(1) at position 2201, AGC and AGT occur at frequencies from about 35–45%, and from about 55–65%, respectively;
(2) at position 2430, TTG and CTG occur at frequencies from about 35–45%, and from about 55–65%, respectively;
(3) at position 2731, CCG and CTG occur at frequencies from about 25–35%, and from about 65–75%, respectively;
(4) at position 3232, GAA and GGA occur at frequencies from about 35–45%, and from about 55–65%, respectively;
(5) at position 3667, AAA and AGA occur at frequencies from about 35–45%, and from about 55–65%, respectively;
(6) at position 4427, TCT and TCC occur at frequencies from about 45–55%, and from about 45–55%, respectively; and (7) at position 4956, AGT and GGT occur at frequencies from about 35–45%, and from about 55–65%, respectively.

A further embodiment of the invention is a set of at least three alternative codon pairs from the group of alternative codon pairs as recited above.

A further embodiment of the invention is a set of at least four alternative codon pairs from the group of alternative codon pairs as recited above.

A further embodiment of the invention is a set of at least five alternative codon pairs from the group of alternative codon pairs as recited above.

A further embodiment of the invention is a set of at least six alternative codon pairs from the group of alterative codon pairs as recited above.

A further embodiment of tie invention is a set of at least seven alternative codon pairs from the group of alternative codon pairs as recited above.

A further embodiment of the invention is a method of identifying individuals having a BRCA1 gene with a BRCA1 coding sequence not associated with disease comprising the steps of:

(1) amplifying a DNA fragment of an individual's BRCA1 coding sequence using an oligonucleotide primer which specifically hybridizes to sequences within the gene;

(2) sequencing said amplified DNA fragment by dideoxy sequencing;

(3) repeating steps (1) and (2) until said individual's BRCA1 coding sequence is completely sequenced;

(4) comparing the sequence of said amplified DNA fragment to BRCA1$^{(omi)}$ DNA sequence, SEQ ID. NO.: 1, SEQ. ID. NO. 3, or SEQ. ID. NO.: 5;

(5) determining the presence or absence of each of the following polymorphic variations in said individual's BRCA1 coding sequence:

(a) AGC and AGT at position 2201;
(b) TTG and CTG at position 2430;
(c) CCG and CTG at position 2731;
(d) GAA and GGA at position 3232;
(e) AAA and AGA at position 3667;
(f) TCT and TCC at position 4427; and
(g) AGT and GGT at position 4956;

(6) determining any sequence differences between said individual's BRCA1 coding sequences and SEQ. ID. NO.: 1, SEQ. ID. NO.: 3, or SEQ. ID. NO.: 5 wherein the presence of said polymorphic variations and the absence of a variation outside of positions 2201, 2430, 2731, 3232, 3667, 4427, and 4956, is correlated with an absence of increased genetic susceptibility to breast or ovarian cancer resulting from a BRCA1 mutation in the BRCA1 coding sequence.

A further embodiment of the invention is a method as described above, wherein codon variations occur at the following frequencies, respectively, in a population of individuals free of disease:

(1) at position 2201, AGC and AGT occur at frequencies from about 35–45%, and from about 55–65%, respectively,
(2) at position 2430, TTG and CTG occur at frequencies from about 35–45%, and from about 55–65%, respectively;
(3) at position 2731, CCG and CTG occur at frequencies from about 25–35%, and from about 65–75%, respectively;
(4) at position 3232, GAA and GGA occur at frequencies from about 35–45%, and from about 55–65%, respectively;
(5) at position 3667, AAA and AGA occur at frequencies from about 35–45%, and from about 55–65%, respectively;
(6) at position 4427, TCT and TCC occur at frequencies from about 45–55%, and from about 45–55%, respectively; and (7) at position 4956, AGT and GGT occur at frequencies from about 35–45%, and from about 55–65%, respectively.

A further embodiment of the invention is a method as described above, wherein said oligonucleotide prier is labeled with a radiolabel, a fluorescent label, a bioluminescent label, a chemiluminescent label, or an enzyme label.

A further embodiment of the invention is a method of detecting an increased genetic susceptibility to breast and ovarian cancer in an individual resulting from the presence of a mutation in the BRCA1 coding sequence, comprising the steps of:

(1) amplifying a DNA fragment of an individual's BRCA1 coding sequence using an oligonucleotide primer which specifically hybridizes to sequences within the gene;

(2) sequencing said amplified DNA fragment by dideoxy sequencing;

(3) repeating steps (1) and (2) until said individual's BRCA1 coding sequence is completely sequenced;

(4) comparing the sequence of said amplified DNA fragment to BRCA1$^{(omi)}$ DNA sequence, SEQ. ID. NO.: 1, SEQ. ID. NO.: 3, or SEQ. ID NO.: 5;

(5) determining any sequence differences between said individual's BRCA1 coding sequences and SEQ. ID. NO.: 1, SEQ. ID. NO.: 3, or SEQ. ID. NO.: 5 to determine the presence or absence of base changes in said individual's BRCA1 coding sequence wherein a said base change is not any one of the following:

(a) AGC and AGT at position 2201;

(b) TTG and CTG at position 2430;

(c) CCG and CTG at position 2731;

(d) GAA and GGA at position 3232;

(e) AAA and AGA at position 3667;

(f) TCT and TCC at position 4427; and (g) AGT and GGT at position 4956; and is correlated with an absence of increased genetic susceptibility to breast or ovarian cancer resulting from a BRCA1 mutation in the BRCA1 coding sequence.

A further embodiment of the invention is a method according to the method above, wherein codon variations occur at the following frequencies, respectively, in a population free of disease:

(1) at position 2201, AGC and AGT occur at frequencies from about 35–45%, and from about 55–65%, respectively;

(2) at position 2430, TTG and CTG occur at frequencies from about 35–45%, and from about 55–65%, respectively;

(3) at position 2731, CCG and CTG occur at frequencies from about 25–35%, and from about 65–75%, respectively;

(4) at position 3232, GAA and GGA occur at frequencies from about 35–45%, and from about 55–65%, respectively;

(5) at position 3667, AAA and AGA occur at frequencies from about 35–45%, and from about 55–65%, respectively;

(6) at position 4427, TCT and TCC occur at frequencies from about 45–55%, and from about 45–55%, respectively; and (7) at position 4956, AGT and GGT occur at frequencies from about 35–45%, and from about 55–65%, respectively.

A further embodiment of the invention is a method according to the method above, wherein said oligonucleotide primer is labeled with a radiolabel, a fluorescent label, a bioluminescent label, a chemiluminescent label, or an enzyme label.

A further embodiment of the invention is a set of codon pairs, which occur at polymorphic position in a BRCA1 gene with a BRCA1 coding sequence as set forth in SEQ. ID. NO.: 1, wherein said set of codon pairs is:

(a) AGC and AGT at position 2201;

(b) TTG and CTG at position 2430;

(c) CCG and CTG at position 2731;

(d) GAA and GGA at position 3232;

(e) AAA and AGA at position 3667;

(f) TCT and TCC at position 4427; and (g) AGT and GGT at position 4956.

A further embodiment of the invention is a set of at least two alternative codon pairs from the set of codon pairs above, wherein said set of at least two alternative codon pairs occur at the following frequencies:

(1) at position 2201, AGC and AGT occur at frequencies of about 40%, and from about 55–65% respectively;

(2) at position 2430, TTG and CTG occur at frequencies from about 35–45%, and from about 55–65%, respectively;

(3) at position 2731, CCG and CTG occur at frequencies from about 25–35%, and from about 65–75%, respectively;

(4) at position 3232 GAA and GGA occur at frequencies from about 35–45%, and from about 55–65%, respectively;

(5) at position 3667, AAA and AGA occur at frequencies from about 35–45%, and from about 55–65%, respectively;

(6) at position 4427, TCT and TCC occur at frequencies from about 45–55%, and from about 45–55%, respectively; and (7) at position 4956, AGT and GGT occur at frequencies from about 35–45%, and from about 55–65%, respectively.

A further embodiment of the invention is a BRCA1 coding sequence as set forth in SEQ. ID. NO.: 1, wherein the codon pairs occur at the following frequencies:

(1) at position 2201, AGC and AGT occur at frequencies of about 40%, and from about 55–65%, respectively;

(2) at position 2430, TTG and CTG occur at frequencies from about 35–45%, and from about 55–65%, respectively;

(3) at position 2731, CCG and CTG occur at frequencies from about 25–35%, and from about 65–75%, respectively;

(4) at position 3232, GAA and GGA occur at frequencies from about 35–45%, and from about 55–65%, respectively;

(5) at position 3667, AAA and AGA occur at frequencies from about 35–45%, and from about 55–65%, respectively;

(6) at position 4427, TCT and TCC occur at frequencies from about 45–55%, and from about 45–55%, respectively; and (7) at position 4956, AGT and GGT occur at frequencies from about 35–45%, and from about 55–65%, respectively.

A further embodiment of the invention is a method of determining the consensus genomic sequence or consensus coding sequence for a target gene, comprising the steps of:

(1) screening a number of individuals in a population for a family history which indicates inheritance of normal alleles for a target gene.

(2) isolating at least one allele of the target gene from individuals found to have a family history which indicates inheritance of normal alleles for a target gene;

(3) sequencing each allele;

(4) comparing the nucleic acid sequence of the genomic sequence or of the coding sequence of each allele of the target gene to determine similarities and differences in the nucleic acid sequence; and (5) determining which allele of the target gene occurs with the greatest frequency.

A further embodiment of the invention is a method of performing gene therapy, comprising the steps of:

(1) transfecting cancer cells in vivo with an effective amount of a vector transformed with a BRCA1 coding sequences of SEQ. ID. NO.: 1, SEQ. ID. NO.: 3, OR SEQ. ID NO.: 5;

(2) allowing the cells to take up the vector; and (3) measuring a reduction in tumor growth.

A further embodiment of the invention is a method of performing protein therapy, comprising the steps of:

(1) injecting into a patient an effective amount of BRCA1 tumor growth inhibiting protein of SEQ. ID. NO.: 2, SEQ. ID. NO.: 4, or SEQ. ID. NO.: 6;

(2) allowing the cells to take up the protein; and (3) measuring a reduction in tumor growth.

SEQUENCING

Any nucleic acid specimen, in purified or non-purified form, can be utilized as the starting nucleic acid or acids, providing it contains, or is suspected of containing, the specific nucleic acid sequence containing a polymorphic locus. Thus, the process may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. See TABLE II. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et. al. in *Molecular Cloning: A Laboratory Manual*, Cold Spring Harbor, N.Y., p 280–281, 1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The primers used to carry out this invention embrace oligonucleotides of sufficient length and appropriate sequence to provide initiation of polymerization. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers used to carry out this invention are designed to be substantially complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the mutation to hybridize therewith and permit amplification of the genomic locus.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859–1862, 1981. One method for synthesizing oligonucleotides on a modified solid support is described in U.S. Pat. No. 4,458,066.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (e.i., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. Amplification is described in *PCR. A Practical Approach*, ILR Press, Eds. M. J. McPherson, P. Quirke, and G. R. Taylor, 1992.

The amplification products may be detected by Southern blots analysis, without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et.al., *Bio/Technology*, 3:1008–1012, 1985), allele-specific oligonucleotide (ASO) probe analysis (Conner, et. al., *Proc. Natl. Acad. Sci. U.S.A.*, 80:278, 1983), oligonucleotide ligation assays (OLAs) (Landgren, et. al., *Science*, 241:1007, 1988), and the like. Molecular techniques for DNA analysis have been reviewed (Landgren, et. al., *Science*, 242:229–237, 1988).

Preferably, the method of amplifying is by PCR, as described herein and as is commonly used by those of ordinary skill in the art. Alternative methods of amplification have been described and can also be employed as long as the BRCA1 locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. Another amplification system useful in the method of the invention is the QB Replicase System. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking DNA repair. Nucleic acid amplification by strand displacement activation (SDA) utilizes a short primer containing a recognition site for hincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented Temperature cycling.

Another method is a process for amplifying nucleic acid sequences from a DNA or RNA template which may be purified or may exist in a mixture of nucleic acids. The resulting nucleic acid sequences may be exact copies of the template, or may be modified. The process has advantages over PCR in that it increases the fidelity of copying a specific nucleic acid sequence, and it allows one to more efficiently detect a particular point mutation in a single assay. A target nucleic acid is amplified enzymatically while avoiding strand displacement. Three primers are used. A first primer is complementary to the first end of the target. A second primer is complementary to the second end of the target. A third primer which is similar to the first end of the target and which is substantially complementary to at least a portion of the first primer such that when the third primer is hybridized to the first primer, the position of the third primer complementary to the base at the 5' end of the first primer contains a modification which substantially avoids strand displacement. This method is detailed in U.S. Pat. No. 5,593,840 to Bhatnagar et al. 1997. Although PCR is the preferred method of amplification if the invention, these other methods can also be used to amplify the BRCA1 locus as described in the method of the invention.

The BRCA1$^{(omi)}$ DNA coding sequences were obtained by end to end sequencing of the BRCA1 alleles of five subjects in the manner described above followed by analysis of the data obtained. The data obtained provided us with the opportunity to evaluate seven previously published polymorphisms and to affirm or correct where necessary, the frequency of occurrence of alternative codons.

GENE THERAPY

The coding sequences can be used for gene therapy.

A variety of methods are known for gene transfer, any of which might be available for use.

Direct Injection of Recombinant DNA In Vivo

1. Direct injection of "naked" DNA directly with a syringe and needle into a specific tissue, infused through a vascular bed, or transferred through a catheter into endothelial cells.

2. Direct injection of DNA that is contained in artificially generated lipid vesicles.

3. Direct injection of DNA conjugated to a targeting structure, such as an antibody.

4. Direct injection by particle bombardment, where the DNA is coated onto gold particles and shot into the cells.

Human Artificial Chromosomes

This novel gene delivery approach involves the use of human chromosomes that have been striped down to contain only the essential components for replication and the genes desired for transfer.

Receptor-Mediated Gene Transfer

DNA is linked to a targeting molecule that will bind to specific cell-surface receptors, inducing endocytosis and transfer of the DNA into mammalian cells. One such technique uses poly-L-lysine to link asialoglycoprotein to DNA. An adenovirus is also added to the complex to disrupt the lysosomes and thus allow the DNA to avoid degradation and move to the nucleus. Infusion of these particles intravenously has resulted in gene transfer into hepatocytes.

RECOMBINANT VIRUS VECTORS

Several vectors are used in gene therapy. Among them are the Moloney Murine Leukemia Virus (MoMLV) Vectors, the adenovirus vectors, the adeno-Associated Virus (AAV) vectors, the herpes simplex virus (HSV) vectors, the poxvirus vectors, and human immunodeficiency virus (HIV) vectors.

GENE REPLACEMENT AND REPAIR

The ideal genetic manipulation for treatment of a genetic disease would be the actual replacement of the defective gene with a normal copy of the gene. Homologous recombination is the term used for switching out a section of DNA and replacing it with a new piece. By this technique, the defective gene can be replaced with a normal gene which expresses a functioning BRCA1 tumor growth inhibitor protein.

A complete description of gene therapy can also be found in "Gene Therapy A Primer For Physicians 2d Ed. by Kenneth W. Culver, M.D. Publ. Mary Ann Liebert Inc. (1996). Two Gene Therapy Protocols for BRCA1 are approved by the Recombinant DNA Advisory Committee for Jeffrey T. Holt et al. They are listed as 9602-148, and 9603-149 and are available from the NIH. The isolated BRCA1 gene can be synthesized or constructed from amplification products and inserted into a vector such as the LXSN vector.

The BRCA1 amino acid and nucleic acid sequence may be used to make diagnostic probes and antibodies. Labeled diagnostic probes may be used by any hybridization method to determine the level of BRCA1 protein in serum or lysed cell suspension of a patient, or solid surface cell sample.

The BRCA1 amino acid sequence may be used to provide a level of protection for patients against risk of breast or ovarian cancer or to reduce the size of a tumor. Methods of making and extracting proteins are well known. Itakura et al. U.S. Pat. Nos. 4,704,362, 5,221,619, and 5,583,013. BRCA1 has been shown to be secreted. Jensen, R. A. et al. *Nature Genetics* 12: 303–308 (1996).

EXAMPLE 1

Determination of the Coding Sequence of a BRCA1$^{(omi)}$ Gene from Five Individuals

MATERIALS AND METHODS

Approximately 150 volunteers were screened in order to identify individuals with no cancer history in their immediate family (i.e. first and second degree relatives). Each person was asked to fill out a hereditary cancer prescreening questionnaire See TABLE I below. Five of these were randomly chosen for end-to-end sequencing of their BRCA1 gene. A first degree relative is a parent, sibling, or offspring. A second degree relative is an aunt, uncle, grandparent, grandchild, niece, nephew, or half-sibling.

TABLE I

Hereditary Cancer Pre-Screening Questionnaire

Part A: Answer the following questions about your family

1. To your knowledge, has anyone in your family been diagnosed with a very specific hereditary colon disease called Familial Adenomatous Polyposis (FAP)?
2. To your knowledge, have you or any aunt had breast cancer diagnosed before the age 35?
3. Have you had Inflammatory Bowel Disease, also called Crohn's Disease or Ulcerative Colitis, for more than 7 years?

Part B: Refer to the list of cancers below for your responses only to questions in Part B

| Bladder Cancer | Lung Cancer | Pancreatic Cancer |
| Breast Cancer | Gastric Cancer | Prostate Cancer |
| Colon Cancer | Malignant Melanoma | Renal Cancer |
| Endometrial Cancer | Ovarian Cancer | Thyroid Cancer |

4. Have your mother or father, your sisters or brothers or your children had any of the listed cancers?
5. Have there been diagnosed in your mother's brothers or sisters, or your mother's parents more than one of the cancers in the above list?
6. Have there been diagnosed in your father's brothers or sisters, or your father's parents more than one of the cancers in the above list?

Part C: Refer to the list of relatives below for responses only to questions in Part C

| You | Your mother |
| Your sisters or brothers | Your mother's sisters or brothers (maternal aunts and uncles) |
| Your children | Your mother's parents (maternal grandparents) |

7. Have there been diagnosed in these relatives 2 or more identical types of cancer? Do not count "simple" skin cancer, also called basal cell or squamous cell skin cancer.
8. Is there a total of 4 or more of any cancers in ths list of relatives above other than "simple" skin cancers?

Part D: Refer to the list of relatives below for responses only to questions in Part D.

| You | Your father |
| Your sisters or brothers | Your father's sisters or brothers (paternal aunts and uncles) |
| Your children | Your father's parents (paternal grandparents) |

9. Have there been diagnosed in these relatives 2 or more identical types of cancer? Do not count "simple" skin cancer, also called basal cell or squamous cell skin cancer.
10. Is there a total of 4 or more of any cancers in the list of relatives above other than "simple" skin cancers?

Genomic DNA was isolated from white blood cells of five subjects selected from analysis of their answers to the questions above. Dideoxy sequence analysis was performed following polymerase chain reaction amplification.

All exons of the BRCA1 gene were subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye was attached for automated sequencing using the Taq Dye Terminator® Kit (Perkin-Elmer cat# 401628). DNA sequencing was performed in both forward and reverse directions on an Applied Biosystems, Inc. (ABI) automated Model 377® sequencer. The software used for analysis of the resulting data was Sequence Navigator® software purchased through ABI.

1. Polymerase Chain Reaction (PCR) Amplification

Genomic DNA (100 nanograms) extracted from white blood cells of five subjects. Each of the five samples was sequenced end to end. Each sample was amplified in a final volume of 25 microliters containing 1 microliter (100 nanograms) genomic DNA, 2.5 microliters 10× PCR buffer (100 mM Tris, pH 8.3, 500 mM KCl, 1.2 mM $MgCl_2$), 2.5 microliters 10× dNTP mix (2 mM each nucleotide), 2.5 microliters forward primer, 2.5 microliters reverse primer, and 1 microliter Taq polymerase (5 units), and 13 microliters of water.

The primers in Table II, below were used to carry out amplification of the various sections of the BRCA1 gene samples. The primers were synthesized on an DNA/RNA Model 394® Synthesizer.

TABLE II

BRCA1 PRIMERS AND SEQUENCING DATA

| EXON | | SEQUENCE | | | | | | | SEQ ID NO. | MER | Mg++ | SIZE |
|---|---|---|---|---|---|---|---|---|---|---|---|---|
| EXON 2 | 2F | 5' | GAA | GTT | GTC | ATT TTA | TAA | ACC TTT-3' | 7 | 24 | 1.6 | ~275 |
| | 2R | 5' | TGT | CTT | TTC | TTC CCT | AGT | ATG T-3' | 8 | 22 | | |
| EXON 3 | 3F | 5' | TCC | TGA | CAC | AGC AGA | CAT | TTA-3' | 9 | 21 | 1.4 | ~375 |
| | 3R | 5' | TTG | GAT | TTT | CGT TCT | CAC | TTA-3' | 10 | 21 | | |
| EXON 5 | 5F | 5' | CTC | TTA | AGG | GCA GTT | GTG | AG-3' | 11 | 20 | 1.2 | ~275 |
| | 5R | 5' | TTC | CTA | CTG | TGG TTG | CTT | CC | 12 | 20[1] | | |
| EXON 6 | 6/7F | 5' | CTT | ATT | TTA | GTG TCC | TTA | AAA GG-3' | 13 | 23 | 1.6 | ~250 |
| | 6R | 5' | TTT | CAT | GGA | CAG CAC | TTG | AGT G-3' | 14 | 22 | | |
| EXON 7 | 7F | 5' | CAC | AAC | AAA | GAG CAT | ACA | TAG GG-3' | 15 | 23 | 1.6 | ~275 |
| | 6/7R | 5' | TCG | GGT | TCA | CTC TGT | AGA | AG-3' | 16 | 20 | | |
| EXON 8 | 8F1 | 5' | TTC | TCT | TCA | GGA GGA | AAA | GCA-3' | 17 | 21 | 1.2 | ~270 |
| | 8R1 | 5' | GCT | GCC | TAC | CAC AAA | TAC | AAA-3' | 18 | 21 | | |
| EXON 9 | 9F | 5' | CCA | CAG | TAG | ATG CTC | AGT | AAATA-3' | 19 | 23 | 1.2 | ~250 |
| | 9R | 5' | TAG | GAA | AAT | ACC AGC | TTC | ATA GA-3' | 20 | 23 | | |
| EXOM 10 | 10F | 5' | TGG | TCA | GCT | TTC TGT | AAT | CG-3' | 21 | 20 | 1.6 | ~250 |
| | 10R | 5' | GTA | TCT | ACC | CAC TCT | CTT | CTT CAG-3' | 22 | 24 | | |
| EXON 11A | 11AF | 5' | CCA | CCT | CCA | AGG TGT | ATC | A-3' | 23 | 19 | 1.2 | 372 |
| | 11AR | 5' | TGT | TAT | GTT | GGC TCC | TTG | CT-3' | 24 | 20 | | |
| EXON 11B | 11BF1 | 5' | CAC | TAA | AGA | CAG AAT | GAA | TCT A-3; | 25 | 21 | 1.2 | ~400 |
| | 11BR1 | 5' | GAA | GAA | CCA | GAA TAT | TCA | TCT A-3' | 26 | 21 | | |
| EXON 11C | 11CF1 | 5' | TGA | TGG | GGA | GTC TGA | ATC | AA-3' | 27 | 20 | 1.2 | ~400 |
| | 11CR1 | 5' | TCT | GCT | TTC | TTG ATA | AAA | TCC T-3' | 28 | 22 | | |
| EXON 11D | 11DF1 | 5' | AGC | GTC | CCC | TCA CAA | ATA | AA-3' | 29 | 20 | 1.2 | ~400 |
| | 11DR1 | 5' | TCA | AGC | GCA | TGA ATA | TGC | CT-3' | 30 | 20 | | |
| EXON 11E | 11EF | 5' | GTA | TAA | GCA | ATA TGG | AAC | TCG A-3' | 31 | 22 | 1.2 | 388 |
| | 11ER | 5' | TTA | AGT | TCA | CTG GTA | TTT | GAA CA-3' | 32 | 23 | | |
| EXON 11F | 11FF | 5' | GAC | AGC | GAT | ACT TTC | CCA | GA-3' | 33 | 20 | 1.2 | 382 |
| | 11FR | 5' | TGG | AAC | AAC | CAT GAA | TTA | GTC-3' | 34 | 21 | | |
| EXON 11G | 11GF | 5' | GGA | AGT | TAG | CAC TCT | AGG | GA-3' | 35 | 20 | 1.2 | 423 |
| | 11GR | 5' | GCA | GTG | ATA | TTA ACT | GTC | TGT A-3' | 36 | 22 | | |
| EXON 11H | 11HF | 5' | TGG | GTC | CTT | AAA GAA | ACA | AAGT-3' | 37 | 22 | 1.2 | 366 |
| | 11HR | 5' | TCA | GGT | GAC | ATT GAA | TCT | TCC-3' | 38 | 21 | | |
| EXON 11I | 11IF | 5' | CCA | CTT | TTT | CCC ATC | AAG | TCA-3' | 39 | 21 | 1.2 | 377 |
| | 11IR | 5' | TCA | GGA | TGC | TTA CAA | TTA | CTT C-3' | 40 | 21 | | |
| EXON 11J | 11JF | 5' | CAA | AAT | TGA | ATG CTA | TGC | TTA GA-3' | 41 | 23 | 1.2 | 377 |
| | 11JR | 5' | TCG | GTA | ACC | CTG AGC | CAA | AT-3' | 42 | 20 | | |
| EXON 11K | 11KF | 5' | GCA | AAAGCG | TCC | AGA AAG | GA-3' | | 43 | 20 | 1.2 | 396 |
| | 11KR- | 15' | TAT | TTG | CAG | TCA AGT | CTT | CCA A-3' | 44 | 22 | | |

TABLE II-continued

BRCA1 PRIMERS AND SEQUENCING DATA

| EXON | SEQUENCE | | | | | | | | | SEQ.ID NO. | MER | Mg++ | SIZE |
|---|---|---|---|---|---|---|---|---|---|---|---|---|---|
| EXON 11L | 11LF-[1] | 15' | GTA | ATA | TTG | GCA | AAG | GCA | TCT-3' | 45 | 22 | 1.2 | 360 |
| | 11LR | 5' | TAA | AAT | GTG | CTC | CCC | AAA | AGC A-3' | 46 | 22 | | |
| EXON 12 | 12F | 5' | GTC | CTG | CCA | ATG | AGA | AGA | AA-3' | 47 | 20 | 1.2 | ~300 |
| | 12R | 5' | TGT | CAG | CAA | ACC | TAA | GAA | TGT-3' | 48 | 21 | | |
| EXON 13 | 13F | 5' | AAT | GGA | AAG | CTT | CTC | | AAAGTA-3' | 49 | 21 | 1.2 | ~325 |
| | 13R | 5' | ATG | TTG | GAG | CTA | GGT | CCT | TAC-3' | 50 | 21 | | |
| EXON 14 | 14F | 5' | CTA | ACC | TGA | ATT | ATC | ACT | ATC A-3' | 51 | 22 | 1.2 | ~310 |
| | 14R | 5' | GTG | TAT | AAATGC | | CTG | TAT | GCA-3' | 52 | 21 | | |
| EXON 15 | 15F | 5' | TGG | CTG | CCC | AGG | AAG | TAT | G-3' | 53 | 19 | 1.2 | ~375 |
| | 15R | 5' | AAC | CAG | AAT | ATC | TTT | ATG | TAG GA-3' | 54 | 23 | | |
| EXON 16 | 16F | 5' | AAT | TCT | TAA | CAG | AGA | CCA | GAA C-3' | 55 | 22 | 1.6 | ~550 |
| | 16R | 5' | AAA | ACT | CTT | TCC | AGA | ATG | TTG T-3' | 56 | 22 | | |
| EXON 17 | 17F | 5' | GTG | TAG | AAC | GTG | CAG | GAT | TG-3' | 57 | 20 | 1.2 | ~275 |
| | 17R | 5' | TCG | CCT | CAT | GTG | GTT | TTA-3' | | 58 | 18 | | |
| EXON 18 | 18F | 5' | GGC | TCT | TTA | GCT | TCT | TAG | GAC-3' | 59 | 21 | 1.2 | ~350 |
| | 18R | 5' | GAG | ACC | ATT | TTC | CCA | GCA | TC-3' | 60 | 20 | | |
| EXON 19 | 19F | 5' | CTG | TCA | TTC | TTC | CTG | TGC | TC-3' | 61 | 20 | 1.2 | ~250 |
| | 19R | 5' | CAT | TGT | TAA | GGA | AAG | TGG | TGC-3' | 62 | 21 | | |
| EXON 20 | 20F | 5' | ATA | TGA | CGT | GTC | TGC | TCC | AC-3' | 63 | 20 | 1.2 | ~425 |
| | 20R | 5' | GGG | AAT | CCA | AAT | TAC | ACA | GC-3' | 64 | 20 | | |
| EXON 21 | 21F | 5' | AAG | CTC | TTC | CTT | TTT | GAA | AGT C-3' | 65 | 22 | 1.6 | ~300 |
| | 21R | 5' | GTA | GAG | AAA | TAG | AAT | AGC | CTC T-3' | 66 | 22 | | |
| EXON 22 | 22F | 5' | TCC | CAT | TGA | GAG | GTC | TTG | CT-3' | 67 | 20 | 1.6 | ~300 |
| | 22R | 5' | GAG | AAG | ACT | TCT | GAG | GCT | AC-3' | 68 | 20 | | |
| EXON 23 | 23F-1 | 5' | TGA | AGT | GAC | AGT | TCC | AGT | AGT-3' | 69 | 21 | 1.2 | ~250 |
| | 23R-1 | 5' | CAT | TTT | AGC | CAT | TCA | TTC | AAC AA-3' | 70 | 23 | | |
| EXON 24 | 24F | 5' | ATG | AAT | TGA | CAC | TAA | TCT | CTG C-3' | 71 | 22 | 1.4 | ~285 |
| | 24R | 5' | GTA | GCC | AGG | ACA | GTA | GAA | GAA-3' | 72 | 21 | | |

[1]M13 tailed

Thirty-five cycles were performed, each consisting of denaturing (95° C.; 30 seconds), annealing (55° C.; 1 minute), and extension (72° C.; 90 seconds), except during the first cycle in which the denaturing time was increased to 5 minutes, and during the last cycle in which the extension time was increased to 5 minutes.

PCR products were purified using Qia-quick® PCR purification kits (Qiagen cat# 28104; Chatsworth, Calif.). Yield and purity of the PCR product determined spectrophotometrically at $OD_{260}$ on a Beckman DU 650 spectrophotometer.

2. Dideoxy Sequence Analysis

Fluorescent dye was attached to PCR products for automated sequencing using the Taq Dye Terminator® Kit (Perkin-Elmer cat# 401628). DNA sequencing was performed in both forward and reverse directions on an Applied Biosystems, Inc. (ABI) Foster City, Calif., automated Model 377® sequencer. The software used for analysis of the resulting data was "Sequence Navigator® software" purchased through ABI.

3. Results

Differences in the nucleic acids of the ten alleles from five individuals were found in seven locations on the gene. The changes and their positions are found on TABLE III, below.

TABLE III

| AMINO ACID CHANGE | NUCLEOTIDE CHANGE | PANEL TYPING | | | | | FREQUENCY |
|---|---|---|---|---|---|---|---|
| | | 1 | 2 | 3 | 4 | 5 | |
| SER(SER) (694) | 11E | C/C | C/T | C/T | T/T | T/T | 0.4 C 0.6 T |
| LEU(LEU) (771) | 11F | T/T | C/T | C/T | C/C | C/C | 0.4 T 0.6 C |
| PRO(LEU) (871) | 11G | C/T | C/T | C/T | T/T | T/T | 0.3 C 0.7 T |
| GLU(GLY) (1038) | 11I | A/A | A/G | A/G | G/G | G/G | 0.4 A 0.6 G |
| LYS(ARG) (1183) | 11J | A/A | A/G | A/G | G/G | G/G | 0.4 A 0.6 G |
| SER(SER) (1436) | 13 | T/T | T/T | T/C | C/C | C/C | 0.5 T 0.5 C |
| SER(GLY) (1613) | 16 | A/A | A/G | A/G | G/G | G/G | 0.4 A 0.6 G |

Tables 3 and 4 depict one aspect of the invention, sets of at least two alternative codon pairs wherein the codon pairs occur in the following frequencies, respectively, in a population of individuals free of disease:

at position 2201, AGC and AGT occur at frequencies from about 35–45%, and from about 55–65%, respectively;

at position 2430, TTG and CTG occur at frequencies from about 35–45%, and from about 55–65%, respectively;

at position 2731, CCG and CTG occur at frequencies from about 25–35%, and from about 65–75%, respectively;

at position 3232, GAA and GGA occur at frequencies from about 35–45%, and from about 55–65%, respectively;

at position 3667, AAA and AGA occur at frequencies from about 35–45%, and from about 55–65%, respectively;

at position 4427, TCT and TCC occur at frequencies from about 45–55%, and from about 45–55%, respectively; and at position 4956, AGT and GGT occur at frequencies from about 35–45%, and from about 55–65%, respectively.

The data show that for each of the samples. The BRCA1 gene is identical except in the region of seven polymorphisms. These polymorphic regions, together with their locations, the amino acid groups of each codon, the frequency of their occurrence and the amino acid coded for by each codon are found in TABLE IV below.

interpret the polymorphic variations without mistaking a variation for a mutation.

Exon 11 of the BRCA1 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the Taq Dye Terminator® Kit (Perkin-Elmer cat# 401628). DNA sequencing is performed in both forward and reverse directions on an Applied Biosystems, Inc. (ABI) automated Model 377® sequencer. The software used for analysis of the resulting data is "Sequence Navigator® software" purchased through ABI.

1. Polymerase Chain Reaction (PCR) Amplification

Genomic DNA (100 nanograms) extracted from white blood cells of the subject is amplified in a final volume of 25 microliters containing 1 microliter (100 nanograms) genomic DNA, 2.5 microliters 10× PCR buffer (100 mM

TABLE IV

CODON AND BASE CHANGES IN SEVEN POLYMORPHIC SITES OF BRCA1 GENE

| SAMPLE NAME | BASE CHANGE | POSITION nt/aa | EXON | CODON CHANGE | AA CHANGE | PUBLISHED FREQUENCY[2] | FREQUENCY IN THIS STUDY |
|---|---|---|---|---|---|---|---|
| 2,3,4,5 | C-T | 2201/694 | 11E | AGC(AGT) | SER—SER | UNPUBLISHED | C = 40% |
| 2,3,4,5 | T-C | 2430/771 | 11F | TTG(CTG) | LEU—LEU | T = 67%[13] | T = 40% |
| 1,2,3,4,5 | C-T | 2731/871 | 11G | CCG(CTG) | PRO—LEU | C = 34%[12] | C = 30% |
| 2,3,4,5 | A-G | 3232/1038 | 11I | GAA(GGA) | GLU—GLY | A = 67%[13] | A = 40% |
| 2,3,4,5 | A-G | 3667/1183 | 11J | AAA(AGA) | LYS—ARG | A = 68%[12] | A = 40% |
| 3,4,5 | T-C | 4427/1436 | 13 | TCT(TCC) | SER—SER | T = 67%[12] | T = 50% |
| 2,3,4,5 | A-G | 4956/1613 | 16 | AGT(GGT) | SER—GLY | A = 67%[12] | A = 40% |

[2]Reference numbers correspond to the Table of References below.

EXAMPLE 2

Determination of a Individual Using BRCA1$^{(OMI)}$ and the Seven Polymorphisms for Reference A person skilled in the art of genetic susceptibility testing will find the present invention useful for:

a) identifying individuals having a BRCA1 gene, who are therefore have no elevated genetic susceptibility to breast or ovarian cancer from a BRCA1 mutation;

b) avoiding misinterpretation of polymorphisms found in the BRCA1 gene;

Sequencing is carried out as in EXAMPLE 1 using a blood sample from the patient in question. However, a BRCA1$^{(omi)}$ sequence is used for reference and the polymorphic sites are compared to the nucleic acid sequences listed above for codons at each polymorphic site. A sample is one which compares to a BRCA1$^{(omi)}$ sequence and contains one of the base variations which occur at each of the polymorphic sites. The codons which occur at each of the polymorphic sites are paired here reference.

AGC and AGT at position 2201,

TTG and CTG at position 2430,

CCG and CTG at position 2731,

GAA and GGA at position 3232,

AAA and AGA at position 3667,

TCT and TCC at position 4427, and

AGT and GGT at position 4956.

The availability of these polymorphic pairs provides added assurance that one skilled in the art can correctly Tris, pH 8.3, 500 mM KCl, 1.2 mM MgCl$_2$), 2.5 microliters 10× dNTP mix (2 mM each nucleotide), 2.5 microliters forward primer (BRCA1-11K-F, 10 micromolar solution), 2.5 microliters reverse primer (BRCA1-11K-R, 10 micromolar solution), and 1 microliter Taq polymerase (5 units), and 13 microliters of water.

The PCR primers used to amplify a patient's sample BRCA1 gene are listed in Table II. The primers were synthesized on an DNA/RNA Model 3940® Synthesizer. Thirty-five cycles are of amplification are performed, each consisting of denaturing (95° C.; 30 seconds), annealing (55° C.; 1 minute), and extension (72° C.; 90 seconds), except during the first cycle in which the denaturing time is increased to 5 minutes, and during the last cycle in which the extension time is increased to 5 minutes.

PCR products are purified using Qia-quick® PCR purification kits (Qiagen, cat# 28104; Chatsworth, Calif.). Yield and purity of the PCR product determined spectrophotometrically at OD$_{260}$ on a Beckman DU 650 spectrophotometer.

2. Dideoxy Sequence Analysis

Fluorescent dye is attached to PCR products for automated sequencing using the Taq Dye Terminator® Kit (Perkin-Elmer cat# 401628). DNA sequencing is performed in both forward and reverse directions on an Applied Biosystems, Inc. (ABI) Foster City, Calif., automated Model 377® sequencer. The software used for analysis of the resulting data is "Sequence Navigator® software" purchased through ABI. The BRCA1$^{(omi1)}$ SEQ. ID. NO.:1 sequence is entered into the Sequence Navigator® software as the Standard for comparison. The Sequence Navigator® software compares the sample sequence to the BRCA1$^{(omi1)}$ SEQ. ID.

NO.:1 standard, base by base. The Sequence Navigator® software highlights all differences between the BRCA1$^{(omi1)}$ SEQ. ID. NO.:1 DNA sequence and the patient's sample sequence.

A first technologist checks the computerized results by comparing visually the BRCA1$^{(omi1)}$ SEQ. ID. NO.:1 standard against the patient's sample, and again highlights any differences between the standard and the sample. The first primary technologist then interprets the sequence variations at each position along the sequence. Chromatograms from each sequence variation are generated by the Sequence Navigator® software and printed on a color printer. The peaks are interpreted by the first primary technologist and a second primary technologist. A secondary technologist then reviews the chromatograms. The results are finally interpreted by a geneticist. In each instance, a variation is compared to known polymorphisms for position and base change. If the sample BRCA1 sequence matches the BRCA1$^{(omi1)}$ SEQ. ID. NO.:1 standard, with only variations within the known list of polymorphisms, it is interpreted as a gene sequence.

EXAMPLE 3

Determining the Absence of a Mutation in the BRCA1 Gene Using BRCA1$^{(omi1)}$ and Seven Polymorphisms for Reference A person skilled in the art of genetic susceptibility testing will find the present invention useful for determining the presence of a known or previously unknown mutation in the BRCA1 gene. A list of mutations of BRCA1 is publicly available in the Breast Cancer Information Core at: http://www.nchgr.nih.gov/dir/lab_transfer/bic. This data site became publicly available on Nov. 1, 1995. Friend, S. et al. Nature Genetics 11:238, (1995). Sequencing is carried out as in EXAMPLE 1 using a blood sample from the patient in question. However, a BRCA1$^{(omi)}$ sequence is used for reference and polymorphic sites are compared to the nucleic acid sequences listed above for codons at each polymorphic site. A sample is one which compares to the BRCA1$^{(omi2)}$ SEQ. ID. NO.: 3 sequence and contains one of the base variations which occur at each of the polymorphic sites. The codons which occur at each of the polymorphic sites are paired here reference.

AGC and AGT at position 2201,
TTG and CTG at position 2430,
CCG and CTG at position 2731,
GAA and GGA at position 3232,
AAA and AGA at position 3667,
TCT and TCC at position 4427, and
AGT and GGT at position 4956.

The availability of these polymorphic pairs provides added assurance that one skilled in the art can correctly interpret the polymorphic variations without mistaking a variation for a mutation.

Exon 11 of the BRCA1 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the Taq Dye Terminator® Kit (Perkin-Elmer cat# 401628). DNA sequencing is performed in both forward and reverse directions on an Applied Biosystems, Inc. (ABI) automated Model 377® sequencer.

The software used for analysis of the resulting data is "Sequence Navigator® software" purchased through ABI.

1. Polymerase Chain Reaction (PCR) Amplification

Genomic DNA (100 nanograms) extracted from white blood cells of the subject is amplified in a final volume of 25 microliters containing 1 microliter (100 nanograms) genomic DNA, 2.5 microliters 10× PCR buffer (100 mM Tris, pH 8.3, 500 mM KCl, 1.2 mM $MgCl_2$), 2.5 microliters 10× dNTP mix (2 mM each nucleotide), 2.5 microliters forward primer (BRCA1-11K-F, 10 micromolar solution), 2.5 microliters reverse primer (BRCA1-11K-R, 10 micromolar solution), and 1 microliter Taq polymerase (5 units), and 13 microliters of water.

The PCR primers used to amplify a patient's sample BRCA1 gene are listed in Table II. The primers were synthesized on an DNA/RNA Model 394® Synthesizer. Thirty-five cycles are of amplification are performed, each consisting of denaturing (95° C.; 30 seconds), annealing (55° C.; 1 minute), and extension (72° C.; 90 seconds), except during the first cycle in which the denaturing time is increased to 5 minutes, and during the last cycle in which the extension time is increased to 5 minutes.

PCR products are purified using Qia-quick® PCR purification kits (Qiagen, cat# 28104; Chatsworth, Calif.). Yield and purity of the PCR product determined spectrophotometrically at $OD_{260}$ on a Beckman DU 650 spectrophotometer.

2. Dideoxy Sequence Analysis

Fluorescent dye is attached to PCR products for automated sequencing using the Taq Dye Terminator® Kit (Perkin-Elmer cat# 401628). DNA sequencing is performed in both forward and reverse directions on an Applied Biosystems, Inc. (ABI) Foster City, Calif., automated Model 377® sequencer. The software used for analysis of the resulting data is "Sequence Navigator® software" purchased through ABI. The BRCA1$^{(omi2)}$ SEQ. ID. NO.: 3 sequence is entered into the Sequence Navigator® software as the Standard for comparison. The Sequence Navigator® software compares the sample sequence to the BRCA1$^{(omi2)}$ SEQ. ID. NO.: 3 standard, base by base. The Sequence Navigator® software highlights all differences between the BRCA1$^{(omi2)}$ SEQ. ID. NO.: 3 DNA sequence and the patient's sample sequence.

A first technologist checks the computerized results by comparing visually the BRCA1$^{(omi2)}$ SEQ. ID. NO.: 3 standard against the patient's sample, and again highlights any differences between the standard and the sample. The first primary technologist then interprets the sequence variations at each position along the sequence. Chromatograms from each sequence variation are generated by the Sequence Navigator® software and printed on a color printer. The peaks are interpreted by the first primary technologist and also by a second primary technologist. A secondary technologist then reviews the chromatograms. The results are finally interpreted by a geneticist. In each instance, a variation is compared to known polymorphisms for position and base change. If the sample BRCA1 sequence matches the BRCA1$^{(omi2)}$ SEQ. ID. NO.: 3 standard, with only variations within the known list of polymorphisms, it is interpreted as a gene sequence.

EXAMPLE 4

Determining the Presence of a Mutation in the BRCA1 Gene Using BRCA1$^{(omi)}$ and Seven Polymorphisms for Reference A person skilled in the art of genetic susceptibility testing will find the present invention useful for determining the presence of a known or previously unknown mutation in the BRCA1 gene. A list of mutations of BRCA1 is publicly available in the Breast Cancer Information Core at: http://www.nchgr.nih.gov/dir/lab_transfer/bic. This data site became publicly available on Nov. 1, 1995. Friend, S. et al. *Native Genetics* 11:238, (1995). In this example, a mutation in exon 11 is characterized by amplifying the region of the mutation with a primer which matches the region of the mutation.

Exon 11 of the BRCA1 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457-486, DePablo, F., Scanes, C., eds., Academic Press, Inc., 1993. Fluorescent dye is attached for automated sequencing using the Taq Dye Terminator® Kit (Perkin-Elmer cat# 401628). DNA sequencing is performed in both forward and reverse directions on an Applied Biosystems, Inc. (ABI) automated Model 377® sequencer. The software used for analysis of the resulting data is "Sequence Navigator® software" purchased through ABI.

1. Polymerase Chain Reaction (PCR) Amplification

Genomic DNA (100 nanograms) extracted from white blood cells of the subject is amplified in a final volume of 25 microliters containing 1 microliter (100 nanograms) genomic DNA, 2.5 microliters 10× PCR buffer (100 mM Tris, pH 8.3, 500 mM KCl, 1.2 mM $MgCl_2$), 2.5 microliters 10× dNTP mix (2 mM each nucleotide), 2.5 microliters forward primer (BRCA1-11K-F, 10 micromolar solution), 2.5 microliters reverse primer (BRCA1-11K-R, 10 micromolar solution), and 1 microliter Taq polymerase (5 units), and 13 microliters of water.

The PCR primers used to amplify segment K of exon 11 (where the mutation is found) are as follows:

BRCA1-11K-F: 5'-GCA AAA GCG TCC AGA AAG GA-3'
SEQ ID NO:69
BRCA1-11K-R: 5'-AGT CTT CCA ATT CAC TGC AC-3'
SEQ ID NO:70

The primers are synthesized on an DNA/RNA Model 394® Synthesizer.

Thirty-five cycles are performed, each consisting of denaturing (95° C.; 30 seconds), annealing (55° C.; 1 minute), and extension (72° C.; 90 seconds), except during the first cycle in which the denaturing time is increased to 5 minutes, and during the last cycle in which the extension time is increased to 5 minutes.

PCR products are purified using Qia-quick® PCR purification kits (Qiagen, cat# 28104; Chatsworth, Calif.). Yield and purity of the PCR product determined spectrophotometrically at $OD_{260}$ on a Beckman DU 650 spectrophotometer.

2. Dideoxy Sequence Analysis

Fluorescent dye is attached to PCR products for automated sequencing using the Taq Dye Terminator® Kit (Perkin-Elmer cat# 401628). DNA sequencing is performed in both forward and reverse directions on an Applied Biosystems, Inc. (ABI) Foster City, Calif., automated Model 377® sequencer. The software used for analysis of the resulting data is "Sequence Navigator® software" purchased through ABI. The BRCA1$^{(omi2)}$ SEQ. ID. NO.: 3 sequence is entered into the Sequence Navigator® software as the Standard for comparison. The Sequence Navigator® software compares the sample sequence to the BRCA1$^{(omi2)}$ SEQ. ID. NO.: 3 standard, base by base. The Sequence Navigator® software highlights all differences between the BRCA1$^{(omi2)}$ SEQ. ID. NO.: 3 DNA sequence and the patient's sample sequence.

A first technologist checks the computerized results by comparing visually the BRCA1$^{(omi2)}$ SEQ. ID. NO.: 3 standard against the patient's sample, and again highlights any differences between the standard and the sample. The first primary technologist then interprets the sequence variations at each position along the sequence. Chromatograms from each sequence variation are generated by the Sequence Navigator® software and printed on a color printer. The peaks are interpreted by the first primary technologist and a second primary technologist. A secondary technologist then reviews the chromatograms. The results are finally interpreted by a geneticist. In each instance, a variation is compared to known polymorphisms for position and base change. Mutations are noted by the length of non-matching variation. Such a lengthy mismatch pattern occurs with deletions and substitutions.

3. Result

Using the above PCR amplification and standard fluorescent sequencing technology, The 3888delGA mutation may be found. The 3888delGA mutation The BRCA1 gene lies in segment "K" of exon 11. The DNA sequence results demonstrate the presence of a two base pair deletion at nucleotides 3888 and 3889 of the published BRCA1$^{(omi)}$ sequence. This mutation interrupts the reading frame of the BRCA1 transcript, resulting in the appearance of an in-frame terminator (TAG) at codon position 1265. This mutation is, therefore, predicted to result in a truncated, and most likely, non-functional protein. The formal name of the mutation will be 3888delGA. This mutation is named in accordance with the suggested nomenclature for naming mutations, Baudet, A et al., *Human Mutation* 2:245-248, (1993).

EXAMPLE 5

Use of the BRCA1$^{(omi1)}$ Gene Therapy

The growth of ovarian, breast or prostate cancer can be arrested by increasing the expression of the BRCA1 gene where inadequate expression of that gene is responsible for hereditary ovarian, breast and prostate cancer. It has been demonstrated that transfection of BRCA1 into cancer cells inhibits their growth and reduces tumorigenesis. Gene therapy is performed on a patient to reduce the size of a tumor. The LXSN vector is transformed with any of the BRCA1$^{(omi1)}$ SEQ. ID. NO.:1, BRCA1$^{(omi2)}$ SEQ. ID. NO.:3, or BRCA1$^{(omi3)}$ SEQ. ID. NO.:5 coding region.

Vector

The LXSN vector is transformed with wildtype BRCA1$^{(omi1)}$ SEQ. ID. NO.:1 coding sequence. The LXSN-BRCA1$^{(omi1)}$ retroviral expression vector is constructed by cloning a SalI-linkered BRCA1$^{(omi1)}$ cDNA (nucleotides 1-5711) into the XhoI site of the vector LXSN. Constructs are confirmed by DNA sequencing. Holt et al. *Nature Genetics* 12: 298-302 (1996). Retroviral vectors are manufactured from viral producer cells using serum free and phenol-red free conditions and tested for sterility, absence of specific pathogens, and absence of replication-competent retrovirus by standard assays. Retrovirus is stored frozen in aliquots which have been tested.

Patients receive a complete physical exam, blood, and urine tests to determine overall health. They may also have a chest X-ray, electrocardiogram, and appropriate radiologic procedures to assess tumor stage.

Patients with metastatic ovarian cancer are treated with retroviral gene therapy by infusion of recombinant LXSN- BRCA1$^{(omi1)}$ retroviral vectors into peritoneal sites containing tumor, between 10$^9$ and 10$^{10}$ viral particles per dose. Blood samples are drawn each day and tested for the presence of retroviral vector by sensitive polymerase chain reaction (PCR)-based assays. The fluid which is removed is analyzed to determine:

1. The percentage of cancer cells which are taking up the recombinant LXSN-BRCA1$^{(omi1)}$ retroviral vector combination. Successful transfer of BRCA1 gene into cancer cells is shown by both RT-PCR analysis and in situ hybridization. RT-PCR is performed with by the method of Thompson et al. *Nature Genetics* 9: 444–450 (1995), using primers derived from BRCA1$^{(omi1)}$ SEQ. ID. NO.:1. Cell lysates are prepared and immunoblotting is performed by the method of Jensen et al. *Nature Genetics* 12: 303–308 1996) and Jensen et al. *Biochemistry* 31: 10887–10892 (1992).

2. Presence of programmed cell death using ApoTAG® in situ apoptosis detection kit (Oncor, Inc., Gaithersburg, Md.) and DNA analysis.

3. Measurement of BRCA I gene expression by slide immunofluorescence or western blot.

Patients with measurable disease are also evaluated for a clinical response to LXSN-BRCAI, especially those that do not undergo a palliative intervention immediately after retroviral vector therapy. Fluid cytology, abdominal girth, CT scans of the abdomen, and local symptoms are followed.

For other sites of disease, conventional response criteria are used as follows:

1. Complete Response (CR), complete disappearance of all measurable lesions and of all signs and symptoms of disease for at least 4 weeks.

2. Partial Response (PR), decrease of at least 50% of the sum of the products of the 2 largest perpendicular diameters of all measurable lesions as determined by 2 observations not less than 4 weeks apart. To be considered a PR, no new lesions should have appeared during this period and none should have increased in size.

3. Stable Disease, less than 25% change in tumor volume from previous evaluations.

4. Progressive Disease, greater than 25% increase in tumor measurements from prior evaluations.

The number of doses depends upon the response to treatment.

For further information related to this gene therpay approach see in "BRCA1 Retroviral Gene Therapy for Ovarian Cancer" a Human Gene Transfer Protocol: NIH ORDA Registration #: 9603-149 Jeffrey Holt, J T, M.D. and Carlos L. Arteaga, M.D.

TABLE OF REFERENCES

1. Sanger, F., et al., *J. Mol. Biol.* 42:1617, (1980).
2. Beaucage, et al., *Tetrahedron Letters* 22:1859–1862, (1981).
3. Maniatis, et. al. in *Molecular Cloning: A Laboratory Manual*, Cold Spring Harbor, N.Y., p 280–281, (1982).
4. Conner, et. al., *Proc. Natl. Acad. Sci. U.S.A.* 80:278, (1983)
5. Saiki, et. al., *Bio/Technology* 3:1008–1012, (1985)
6. Landgren, et. al., *Science* 241:1007, (1988)
7. Landgren, et. al., *Science* 242:229–237, (1988).
8. PCR. A Practical Approach, ILR Press, Eds. M. J. McPherson, P. Quirke, and G. R. Taylor, (1992).
9. Easton et al., *American Journal of Human Genetics* 52:678–701, (1993).
10. U.S. Pat. No. 4,458,066.
11. Rowell, S., et al., *American Journal of Human Genetics* 55:861–865, (1994)
12. Miki, Y. et al., *Science* 266:66–71, (1994).
13. Friedman, L. et al., *Nature Genetics* 8:399–404, (1994).
14. Baudet, A et al., *Human Mutation* 2:245–248, (1993).
15. Friend, S. et al., *Nature Genetics* 11:238, (1995).
16. Arteaga, C L and J T Holt *Cancer Research* 56:1098–1103 (1996).
17. Holt, J T et al., *Nature Genetics* 12:298–302 (1996).
18. Jensen, R A et al., *Nature Genetics* 12:303–308 (1996).
19. Steeg, P. *Nature Genetics* 12:223–225 (1996).
20. Thompson, M E et al., *Nature Genetics* 9: 444–450 (1995)
21. Holt, J T, and C. Arteaga, Gene Therapy Protocol ORDA #: 9603-149 ORDA approved Protocol for BRCA1 Gene Therapy.

"Breast and Ovarian cancer" is understood by those skilled in the art to include breast and ovarian cancer in women and also breast and prostate cancer in men. BRCA1 is associated genetic susceptibility to inherited breast and ovarian cancer in women and also breast and prostate cancer in men. Therefore, claims in this document which recite breast and/or ovarian cancer refer to breast, ovarian and prostate cancers in men and women. Although the invention has been described with reference to the presently preferred embodiments, it should be understood that various modifications can be made without departing from the spirit of the invention. Accordingly, the invention is limited only by the following claims.

We claim:

1. An isolated coding sequence of the BRCA1 gene as set forth in SEQ. ID. NO.: 5.

2. A method of identifying individuals having a BRCA1 gene with a BRCA1 coding sequence not associated with ovarian or breast cancer disease, comprising:
   (a) amplifying a DNA fragment of an individual's BRCA1 coding sequence using an oligonucleotide primer which specifically hybridizes to sequences within the gene;
   (b) sequencing said amplified DNA fragment by dideoxy sequencing;
   (c) repeating steps (a) and (b) until said individual's BRCA1 coding sequence is completely sequenced;
   (d) comparing the sequence of said amplified DNA fragment to a BRCA1$^{(omi)}$ DNA sequence selected from the group consisting of: SEQ ID NO: 1 together with SEQ ID NO: 3, SEQ ID NO: 1 together with SEQ ID NO: 5, SEQ ID NO: 3 together with SEQ ID NO: 5, SEQ ID NO: 1 together with SEQ ID NO: 3 together with SEQ ID NO: 5, SEQ ID NO: 3 and SEQ ID NO: 5;
   (e) determining the presence or absence of each of the following polymorphic variations in said individual's BRCA1 coding sequence:
      (i) C and T at position 2201,
      (ii) T and C at position 2430,
      (iii) C and T at position 2731,
      (iv) A and G at position 3232,
      (v) A and G at position 3667,
      (vi) T and C at position 4427, and
      (vii) A and G at position 4956;
   (f) determining any sequence differences between said individual's BRCA1 coding sequences and a BRCA1$^{(omi)}$ DNA sequence selected from the group consisting of: SEQ ID NO: 1 together with SEQ ID NO: 3, SEQ ID NO: 1 together with SEQ ID NO: 5, SEQ ID NO: 3 together with SEQ ID NO: 5, SEQ ID NO: 1 together with SEQ ID NO: 3 together with SEQ ID NO: 5, SEQ ID NO: 3 and SEQ ID NO: 5, wherein the presence of said polymorphic variations and the absence of a variation outside of positions 2201, 2430, 2731, 3232, 3667, 4427 and 4956 is correlated with an absence of increased genetic susceptibility to breast or ovarian cancer resulting from a BRCA1 mutation in the BRCA1 coding sequence.

3. A method of identifying individuals having a BRCA1 gene with a BRCA1 coding sequence not associated with ovarian or breast cancer disease, comprising:
   (a) amplifying a DNA fragment of an individual's BRCA1 coding sequence using an oligonucleotide primer which specifically hybridizes to sequences within the gene;

(b) sequencing said amplified DNA fragment by dideoxy sequencing;

(c) repeating steps (a) and (b) until said individual's BRCA1 coding sequence is completely sequenced;

(d) comparing the sequence of said amplified DNA fragment to a BRCA1$^{(omi)}$ DNA sequence selected from the group consisting of: SEQ ID NO: 1 together with SEQ ID NO: 3, SEQ ID NO: 1 together with SEQ ID NO: 5, SEQ ID NO: 3 together with SEQ ID NO: 5, SEQ ID NO: 1 together with SEQ ID NO: 3 together with SEQ ID NO: 5, SEQ ID NO: 3 and SEQ ID NO: 5;

(e) determining the presence or absence of each of the following polymorphic variations in said individual's BRCA1 coding sequence:
  (i) C and T at position 2201,
  (ii) T and C at position 2430,
  (iii) C an d T at position 2731,
  (iv) A and G at position 3232,
  (v) A and G at position 3667,
  (vi) T and C at position 4427, and
  (vii) A and G at position 4956; and (f) determining any sequence differences between said individual's BRCA1 coding sequences and a BRCA1$^{(omi)}$ DNA sequence selected from the group consisting of: SEQ ID NO: 1 together with SEQ ID NO: 3, SEQ ID NO: 1 together with SEQ ID NO: 5, SEQ ID NO: 3 together with SEQ ID NO: 5, SEQ ID NO: 1 together with SEQ ID NO: 3 together with SEQ ID NO: 5, SEQ ID NO: 3 and SEQ ID NO: 5, wherein the presence of said polymorphic variations and the absence of a variation outside of positions 2201, 2430, 2731, 3232, 3667, 4427 and 4956 is correlated with an absence of increased genetic susceptibility to breast or ovarian cancer resulting from a BRCA1 mutation in the BRCA1 coding sequence;

wherein codon variations occur at the following frequencies, respectively, in a Caucasian population of individuals with no family history of breast or ovarian cancer:

(i) at position 2201, C and T occur at frequencies from about 35 to about 45%, and from about 55 to about 65%, respectively;

(ii) at position 2430, T and C occur at frequencies from about 35 to about 45%, and from about 55 to about 65%, respectively;

(iii) at position 2731, C and T occur at frequencies from about 25 to about 35%, and from about 65 to about 75%, respectively;

(iv) at position 3232, A and G occur at frequencies from about 35 to about 45%, and from about 55 to about 65%, respectively;

(v) at position 3667, A and G occur at frequencies from about 35 to about 45%, and from about 55 to about 65%, respectively;

(vi) at position 4427, T and C occur at frequencies from about 45 to about 55%, and from about 45 to about 55%, respectively; and (vii) at position 4956, A and G occur at frequencies from about 35 to about 45%, and from about 55 to about 65%, respectively.

4. A method according to claims 2 or 3, wherein said oligonucleotide primer is labeled with a radiolabel, a fluorescent label, a bioluminescent label, a chemiluminescent label, or an enzyme label.

5. A method of detecting an increased genetic susceptibility to breast and ovarian cancer in an individual resulting from the presence of a mutation in the BRCA1 coding sequence, comprising:

(a) amplifying a DNA fragment of an individual's BRCA1 coding sequence using an oligonucleotide primer which specifically hybridizes to sequences within the gene;

(b) sequencing said amplified DNA fragment by dideoxy sequencing;

(c) repeating steps (a) and (b) until said individual's BRCA1 coding sequence is completely sequenced;

(d) comparing the sequence of said amplified DNA fragment to a BRCA1$^{(omi)}$ DNA sequence selected from the group consisting of: SEQ ID NO: 1 together with SEQ ID NO: 3, SEQ ID NO: 1 together with SEQ ID NO: 5, SEQ ID NO: 3 together with SEQ ID NO: 5, SEQ ID NO: 1 together with SEQ ID NO: 3 together with SEQ ID NO: 5, SEQ ID NO: 3 and SEQ ID NO: 5;

(e) determining any sequence differences between said individual's BRCA1 coding sequences and a BRCA1$^{(omi)}$ DNA sequence selected from the group consisting of: SEQ. ID. NO.: 1 together with SEQ ID NO: 3, SEQ ID NO: 1 together with SEQ ID NO: 5, SEQ ID NO: 3 together with SEQ ID NO: 5, SEQ ID NO: 1 together with SEQ ID NO: 3 together with SEQ ID NO: 5, SEQ ID NO: 3 and SEQ ID NO: 5 in order to determine the presence or absence of base changes in said individual's BRCA1 coding sequence wherein a base change which is not any one of the following:
  (i) C and T at position 2201,
  (ii) T and C at position 2430,
  (iii) C and T at position 2731,
  (iv) A and G at position 3232,
  (v) A and G at position 3667,
  (vi) T and C at position 4427, and
  (vii) A and G at position 4956, is correlated with the potential of increased genetic susceptibility to breast or ovarian cancer resulting from a BRCA1 mutation in the BRCA1 coding sequence.

6. A method of detecting an increased genetic susceptibility to breast and ovarian cancer in an individual resulting from the presence of a mutation in the BRCA1 coding sequence, comprising:

(a) amplifying a DNA fragment of an individual's BRCA1 coding sequence using an oligonucleotide primer which specifically hybridizes to sequences within the gene;

(b) sequencing said amplified DNA fragment by dideoxy sequencing;

(c) repeating steps (a) and (b) until said individual's BRCA1 coding sequence is completely sequenced;

(d) comparing the sequence of said amplified DNA fragment to a BRCA1$^{(omi)}$ DNA sequence selected from the group consisting of: SEQ ID NO: 1 together with SEQ ID NO: 3, SEQ ID NO: 1 together with SEQ ID NO: 5, SEQ ID NO: 3 together with SEQ ID NO: 5, SEQ ID NO: 1 together with SEQ ID NO: 3 together with SEQ ID NO: 5, SEQ ID NO: 3 and SEQ ID NO: 5;

(e) determining any sequence differences between said individual's BRCA1 coding sequences and a BRCA1$^{(omi)}$ DNA sequence selected from the group consisting of: SEQ ID NO: 1 together with SEQ ID NO: 3, SEQ ID NO: 1 together with SEQ ID NO: 5, SEQ ID NO: 3 together with SEQ ID NO: 5, SEQ ID NO: 1 together with SEQ ID NO: 3 together with SEQ ID NO: 5, SEQ ID NO: 3 and SEQ ID NO: 5 in order to determine the presence or absence of base changes in said individual's BRCA1 coding sequence wherein a base change which is not any one of the following:
(i) C and T at position 2201,
(ii) T and C at position 2430,
(iii) C and T at position 2731,
(iv) A and G at position 3232,
(v) A and G at position 3667,
(vi) T and C at position 4427, and
(vii) A and G at position 4956, is correlated with the potential of increased genetic susceptibility to breast or ovarian cancer resulting from a BRCA1 mutation in the BRCA1 coding sequence, wherein codon variations occur at the following frequencies, respectively, in a Caucasian population of individuals with no family history of breast or ovarian cancer:
(i) at position 2201, C and T occur at frequencies from about 35 to about 45%, and from about 55 to about 65%, respectively;
(ii) at position 2430, T and C occur at frequencies from about 35 to about 45%, and from about 55 to about 65%, respectively;
(iii) at position 2731, C and T occur at frequencies from about 25 to about 35%, and from about 65 to about 75%, respectively;
(iv) at position 3232, A and G occur at frequencies from about 35 to about 45%, and from about 55 to about 65%, respectively;
(v) at position 3667, A and G occur at frequencies from about 35 to about 45%, and from about 55 to about 65%, respectively;
(vi) at position 4427, T and C occur at frequencies from about 45 to about 55%, and from about 45 to about 55%, respectively; and (vii) at position 4956, A and G occur at frequencies from about 35 to about 45%, and from about 55 to about 65%, respectively.

7. A method according to claims 5 or 6, wherein said oligonucleotide primer is labeled with a radiolabel, a fluorescent label, a bioluminescent label, a chemiluminescent label, or an enzyme label.

8. A BRCA1 coding sequence according to claim 5 wherein the codon pairs occur at the following frequencies, in a Caucasian population of individuals with no family history of breast or ovarian cancer:

(i) at position 2201, C and T occur at frequencies of about 40%, and from about 55% to about 65%, respectively;
(ii) at position 2430, T and C occur at frequencies of about 35 to about 45%, and from about 55% to about 65%, respectively;
(iii) at position 2731, C and T occur at frequencies of about 25 to about 35%, and from about 65% to about 75%, respectively;
(iv) at position 3232, A and G occur at frequencies of about 35 to about 45%, and from about 55% to about 65%, respectively;
(v) at position 3667, A and G occur at frequencies of about 35 to about 45%, and from about 55% to about 65%, respectively;
(vi) at position 4427, T and C occur at frequencies of about 45 to about 55%, and from about 45% to about 55%, respectively; and
(ii) at position 4956, A and G occur at frequencies of about 35 to about 45%, and from about 55% to about 65%, respectively.

* * * * *

UNITED STATES PATENT AND TRADEMARK OFFICE
CERTIFICATE OF CORRECTION

PATENT NO. : 5,750,400
DATED : May 12, 1998
INVENTOR(S) : Patricia D. Murphy et al.

Page 1 of 1

It is certified that error appears in the above-identified patent and that said Letters Patent is hereby corrected as shown below:

Column 2,
Lines 42-43, delete "BRCA1$^{(omi2)}$ SEQ ID NO: 3 and BRCA1$^{(omi3)}$ SEQ ID NO: 5" and add -- BRCA1$^{(omi2)}$ SEQ ID NO: 5 and BRCA1$^{(omi3)}$ SEQ ID NO: 3 --.

Column 4,
Lines 29-30, delete "SEQ ID NO: 3 and SEQ ID NO: 5 respectively" and add -- SEQ ID NO: 5 and SEQ ID NO: 3 respectively --.

Column 21,
Line 41, delete "SEQ ID NO: 3" and add -- SEQ ID NO: 5 --.

Column 22,
Lines 42, 45, 58 and 67, delete "SEQ ID NO: 3" and add -- SEQ ID NO: 5 --.

Column 23,
Line 63, delete "SEQ ID NO: 3" and add -- SEQ ID NO: 5 --.

Column 24,
Lines 2 and 5, delete "SEQ ID NO: 3" and add -- SEQ ID NO: 5 --.

Signed and Sealed this

Seventeenth Day of February, 2004

JON W. DUDAS
*Acting Director of the United States Patent and Trademark Office*

SEQUENCE LISTING ( 1 ) GENERAL INFORMATION:

( i i i ) NUMBER OF SEQUENCES: 72

( 2 ) INFORMATION FOR SEQ ID NO:1:

( i ) SEQUENCE CHARACTERISTICS:
        ( A ) LENGTH: 5711 base pairs
        ( B ) TYPE: nucleic acid
        ( C ) STRANDEDNESS: Not Relevant
        ( D ) TOPOLOGY: linear ( i i ) MOLECULE TYPE: cDNA ( v i ) ORIGINAL SOURCE:
        ( A ) ORGANISM: Homo sapiens
        ( B ) STRAIN: BRCA1

(viii) POSITION IN GENOME:
  (A) CHROMOSOME/SEGMENT: 17
  (B) MAP POSITION: 17q21

(xi) SEQUENCE DESCRIPTION: SEQ ID NO:1:

```
AGCTCGCTGA GACTTCCTGG ACCCCGCACC AGGCTGTGGG GTTTCTCAGA TAACTGGGCC      60
CCTGCGCTCA GGAGGCCTTC ACCCTCTGCT CTGGGTAAAG TTCATTGGAA CAGAAAGAAA     120
TGGATTTATC TGCTCTTCGC GTTGAAGAAG TACAAAATGT CATTAATGCT ATGCAGAAAA     180
TCTTAGAGTG TCCCATCTGT CTGGAGTTGA TCAAGGAACC TGTCTCCACA AAGTGTGACC     240
ACATATTTTG CAAATTTTGC ATGCTGAAAC TTCTCAACCA GAAGAAGGG  CCTTCACAGT     300
GTCCTTTATG TAAGAATGAT ATAACCAAAA GGAGCCTACA AGAAAGTACG AGATTTAGTC     360
AACTTGTTGA AGAGCTATTG AAAATCATTT GTGCTTTTCA GCTTGACACA GGTTTGGAGT     420
ATGCAAACAG CTATAATTTT GCAAAAAAGG AAAATAACTC TCCTGAACAT CTAAAAGATG     480
AAGTTTCTAT CATCCAAAGT ATGGGCTACA GAAACCGTGC CAAAAGACTT CTACAGAGTG     540
AACCCGAAAA TCCTTCCTTG CAGGAAACCA GTCTCAGTGT CCAACTCTCT AACCTTGGAA     600
CTGTGAGAAC TCTGAGGACA AAGCAGCGGA TACAACCTCA AAAGACGTCT GTCTACATTG     660
AATTGGGATC TGATTCTTCT GAAGATACCG TTAATAAGGC AACTTATTGC AGTGTGGGAG     720
ATCAAGAATT GTTACAAATC ACCCCTCAAG GAACCAGGGA TGAAATCAGT TTGGATTCTG     780
CAAAAAAGGC TGCTTGTGAA TTTTCTGAGA CGGATGTAAC AAATACTGAA CATCATCAAC     840
CCAGTAATAA TGATTTGAAC ACCACTGAGA AGCGTGCAGC TGAGAGGCAT CCAGAAAAGT     900
ATCAGGGTAG TTCTGTTTCA AACTTGCATG TGGAGCCATG TGGCACAAAT ACTCATGCCA     960
GCTCATTACA GCATGAGAAC AGCAGTTTAT TACTCACTAA AGACAGAATG AATGTAGAAA    1020
AGGCTGAATT CTGTAATAAA AGCAAACAGC CTGGCTTAGC AAGGAGCCAA CATAACAGAT    1080
GGGCTGGAAG TAAGGAAACA TGTAATGATA GGCGGACTCC CAGCACAGAA AAAAGGTAG     1140
ATCTGAATGC TGATCCCCTG TGTGAGAGAA AGAATGGAA  TAAGCAGAAA CTGCCATGCT    1200
CAGAGAATCC TAGAGATACT GAAGATGTTC CTTGGATAAC ACTAAATAGC AGCATTCAGA    1260
AAGTTAATGA GTGGTTTTCC AGAAGTGATG AACTGTTAGG TTCTGATGAC TCACATGATG    1320
GGGAGTCTGA ATCAAATGCC AAAGTAGCTG ATGTATTGGA CGTTCTAAAT GAGGTAGATG    1380
AATATTCTGG TTCTTCAGAG AAAATAGACT TACTGGCCAG TGATCCTCAT GAGGCTTTAA    1440
TATGTAAAAG TGAAAGAGTT CACTCCAAAT CAGTAGAGAG TAATATTGAA GACAAAATAT    1500
TTGGGAAAAC CTATCGGAAG AAGGCAAGCC TCCCCAACTT AAGCCATGTA ACTGAAAATC    1560
TAATTATAGG AGCATTTGTT ACTGAGCCAC AGATAATACA AGAGCGTCCC CTCACAAATA    1620
AATTAAAGCG TAAAAGGAGA CCTACATCAG GCCTTCATCC TGAGGATTTT ATCAAGAAAG    1680
CAGATTTGGC AGTTCAAAAG ACTCCTGAAA TGATAAATCA GGGAACTAAC CAAACGGAGC    1740
AGAATGGTCA AGTGATGAAT ATTACTAATA GTGGTCATGA GAATAAAACA AAAGGTGATT    1800
CTATTCAGAA TGAGAAAAAT CCTAACCCAA TAGAATCACT CGAAAAGAA  TCTGCTTTCA    1860
AAACGAAAGC TGAACCTATA AGCAGCAGTA TAAGCAATAT GGAACTCGAA TTAAATATCC    1920
ACAATTCAAA AGCACCTAAA AAGAATAGGC TGAGGAGGAA GTCTTCTACC AGGCATATTC    1980
ATGCGCTTGA ACTAGTAGTC AGTAGAAATC TAAGCCCACC TAATTGTACT GAATTGCAAA    2040
TTGATAGTTG TTCTAGCAGT GAAGAGATAA AGAAAAAAA  GTACAACCAA ATGCCAGTCA    2100
GGCACAGCAG AAACCTACAA CTCATGGAAG GTAAAGAACC TGCAACTGGA GCCAAGAAGA    2160
GTAACAAGCC AAATGAACAG ACAAGTAAAA GACATGACAG TGATACTTTC CCAGAGCTGA    2220
```

| | | | | | |
|---|---|---|---|---|---|
| AGTTAACAAA | TGCACCTGGT | TCTTTTACTA | AGTGTTCAAA | TACCAGTGAA | CTTAAAGAAT | 2280 |
| TTGTCAATCC | TAGCCTTCCA | AGAGAAGAAA | AAGAAGAGAA | ACTAGAAACA | GTTAAAGTGT | 2340 |
| CTAATAATGC | TGAAGACCCC | AAAGATCTCA | TGTTAAGTGG | AGAAAGGGTT | TTGCAAACTG | 2400 |
| AAAGATCTGT | AGAGAGTAGC | AGTATTTCAC | TGGTACCTGG | TACTGATTAT | GGCACTCAGG | 2460 |
| AAAGTATCTC | GTTACTGGAA | GTTAGCACTC | TAGGGAAGGC | AAAAACAGAA | CCAAATAAAT | 2520 |
| GTGTGAGTCA | GTGTGCAGCA | TTTGAAAACC | CCAAGGGACT | AATTCATGGT | TGTTCCAAAG | 2580 |
| ATAATAGAAA | TGACACAGAA | GGCTTTAAGT | ATCCATTGGG | ACATGAAGTT | AACCACAGTC | 2640 |
| GGGAAACAAG | CATAGAAATG | GAAGAAAGTG | AACTTGATGC | TCAGTATTTG | CAGAATACAT | 2700 |
| TCAAGGTTTC | AAAGCGCCAG | TCATTTGCTC | TGTTTTCAAA | TCCAGGAAAT | GCAGAAGAGG | 2760 |
| AATGTGCAAC | ATTCTCTGCC | CACTCTGGGT | CCTTAAAGAA | ACAAAGTCCA | AAAGTCACTT | 2820 |
| TTGAATGTGA | ACAAAAGGAA | GAAAATCAAG | GAAAGAATGA | GTCTAATATC | AAGCCTGTAC | 2880 |
| AGACAGTTAA | TATCACTGCA | GGCTTTCCTG | TGGTTGGTCA | GAAAGATAAG | CCAGTTGATA | 2940 |
| ATGCCAAATG | TAGTATCAAA | GGAGGCTCTA | GGTTTGTCT | ATCATCTCAG | TTCAGAGGCA | 3000 |
| ACGAAACTGG | ACTCATTACT | CCAAATAAAC | ATGGACTTTT | ACAAAACCCA | TATCGTATAC | 3060 |
| CACCACTTTT | TCCCATCAAG | TCATTTGTTA | AAACTAAATG | TAAGAAAAAT | CTGCTAGAGG | 3120 |
| AAAACTTTGA | GGAACATTCA | ATGTCACCTG | AAAGAGAAAT | GGGAAATGAG | AACATTCCAA | 3180 |
| GTACAGTGAG | CACAATTAGC | CGTAATAACA | TTAGAGAAAA | TGTTTTTAAA | GGAGCCAGCT | 3240 |
| CAAGCAATAT | TAATGAAGTA | GGTTCCAGTA | CTAATGAAGT | GGGCTCCAGT | ATTAATGAAA | 3300 |
| TAGGTTCCAG | TGATGAAAAC | ATTCAAGCAG | AACTAGGTAG | AAACAGAGGG | CCAAAATTGA | 3360 |
| ATGCTATGCT | TAGATTAGGG | GTTTTGCAAC | CTGAGGTCTA | TAAACAAAGT | CTTCCTGGAA | 3420 |
| GTAATTGTAA | GCATCCTGAA | ATAAAAAAGC | AAGAATATGA | AGAAGTAGTT | CAGACTGTTA | 3480 |
| ATACAGATTT | CTCTCCATAT | CTGATTTCAG | ATAACTTAGA | ACAGCCTATG | GGAAGTAGTC | 3540 |
| ATGCATCTCA | GGTTTGTTCT | GAGACACCTG | ATGACCTGTT | AGATGATGGT | GAAATAAAGG | 3600 |
| AAGATACTAG | TTTTGCTGAA | AATGACATTA | AGGAAAGTTC | TGCTGTTTTT | AGCAAAAGCG | 3660 |
| TCCAGAGAGG | AGAGCTTAGC | AGGAGTCCTA | GCCCTTTCAC | CCATACACAT | TTGGCTCAGG | 3720 |
| GTTACCGAAG | AGGGGCCAAG | AAATTAGAGT | CCTCAGAAGA | GAACTTATCT | AGTGAGGATG | 3780 |
| AAGAGCTTCC | CTGCTTCCAA | CACTTGTTAT | TTGGTAAAGT | AAACAATATA | CCTTCTCAGT | 3840 |
| CTACTAGGCA | TAGCACCGTT | GCTACCGAGT | GTCTGTCTAA | GAACACAGAG | GAGAATTTAT | 3900 |
| TATCATTGAA | GAATAGCTTA | AATGACTGCA | GTAACCAGGT | AATATTGGCA | AAGGCATCTC | 3960 |
| AGGAACATCA | CCTTAGTGAG | GAAACAAAAT | GTTCTGCTAG | CTTGTTTTCT | TCACAGTGCA | 4020 |
| GTGAATTGGA | AGACTTGACT | GCAAATACAA | ACACCCAGGA | TCCTTTCTTG | ATTGGTTCTT | 4080 |
| CCAAACAAAT | GAGGCATCAG | TCTGAAAGCC | AGGGAGTTGG | TCTGAGTGAC | AAGGAATTGG | 4140 |
| TTTCAGATGA | TGAAGAAAGA | GGAACGGGCT | TGGAAGAAAA | TAATCAAGAA | GAGCAAAGCA | 4200 |
| TGGATTCAAA | CTTAGGTGAA | GCAGCATCTG | GGTGTGAGAG | TGAAACAAGC | GTCTCTGAAG | 4260 |
| ACTGCTCAGG | GCTATCCTCT | CAGAGTGACA | TTTTAACCAC | TCAGCAGAGG | GATACCATGC | 4320 |
| AACATAACCT | GATAAAGCTC | CAGCAGGAAA | TGGCTGAACT | AGAAGCTGTG | TTAGAACAGC | 4380 |
| ATGGGAGCCA | GCCTTCTAAC | AGCTACCCTT | CCATCATAAG | TGACTCCTCT | GCCCTTGAGG | 4440 |
| ACCTGCGAAA | TCCAGAACAA | AGCACATCAG | AAAAAGCAGT | ATTAACTTCA | CAGAAAAGTA | 4500 |
| GTGAATACCC | TATAAGCCAG | AATCCAGAAG | GCCTTTCTGC | TGACAAGTTT | GAGGTGTCTG | 4560 |
| CAGATAGTTC | TACCAGTAAA | AATAAAGAAC | CAGGAGTGGA | AAGGTCATCC | CCTTCTAAAT | 4620 |

-continued

| | | | | | |
|---|---|---|---|---|---|
| GCCCATCATT | AGATGATAGG | TGGTACATGC | ACAGTTGCTC | TGGGAGTCTT | CAGAATAGAA | 4680 |
| ACTACCCATC | TCAAGAGGAG | CTCATTAAGG | TTGTTGATGT | GGAGGAGCAA | CAGCTGGAAG | 4740 |
| AGTCTGGGCC | ACACGATTTG | ACGGAAACAT | CTTACTTGCC | AAGGCAAGAT | CTAGAGGGAA | 4800 |
| CCCCTTACCT | GGAATCTGGA | ATCAGCCTCT | TCTCTGATGA | CCCTGAATCT | GATCCTTCTG | 4860 |
| AAGACAGAGC | CCCAGAGTCA | GCTCGTGTTG | GCAACATACC | ATCTTCAACC | TCTGCATTGA | 4920 |
| AAGTTCCCCA | ATTGAAAGTT | GCAGAATCTG | CCCAGGGTCC | AGCTGCTGCT | CATACTACTG | 4980 |
| ATACTGCTGG | GTATAATGCA | ATGGAAGAAA | GTGTGAGCAG | GGAGAAGCCA | GAATTGACAG | 5040 |
| CTTCAACAGA | AAGGGTCAAC | AAAAGAATGT | CCATGGTGGT | GTCTGGCCTG | ACCCCAGAAG | 5100 |
| AATTTATGCT | CGTGTACAAG | TTTGCCAGAA | AACACCACAT | CACTTTAACT | AATCTAATTA | 5160 |
| CTGAAGAGAC | TACTCATGTT | GTTATGAAAA | CAGATGCTGA | GTTTGTGTGT | GAACGGACAC | 5220 |
| TGAAATATTT | TCTAGGAATT | GCGGGAGGAA | AATGGGTAGT | TAGCTATTTC | TGGGTGACCC | 5280 |
| AGTCTATTAA | AGAAAGAAAA | ATGCTGAATG | AGCATGATTT | TGAAGTCAGA | GGAGATGTGG | 5340 |
| TCAATGGAAG | AAACCACCAA | GGTCCAAAGC | GAGCAAGAGA | ATCCCAGGAC | AGAAAGATCT | 5400 |
| TCAGGGGGCT | AGAAATCTGT | TGCTATGGGC | CCTTCACCAA | CATGCCCACA | GATCAACTGG | 5460 |
| AATGGATGGT | ACAGCTGTGT | GGTGCTTCTG | TGGTGAAGGA | GCTTTCATCA | TTCACCCTTG | 5520 |
| GCACAGGTGT | CCACCCAATT | GTGGTTGTGC | AGCCAGATGC | CTGGACAGAG | GACAATGGCT | 5580 |
| TCCATGCAAT | TGGGCAGATG | TGTGAGGCAC | CTGTGGTGAC | CCGAGAGTGG | GTGTTGGACA | 5640 |
| GTGTAGCACT | CTACCAGTGC | CAGGAGCTGG | ACACCTACCT | GATACCCCAG | ATCCCCCACA | 5700 |
| GCCACTACTG | A | | | | | 5711 |

( 2 ) INFORMATION FOR SEQ ID NO:2:

( i ) SEQUENCE CHARACTERISTICS:
        ( A ) LENGTH: 1863 amino acids
        ( B ) TYPE: amino acid
        ( C ) STRANDEDNESS: Not Relevant
        ( D ) TOPOLOGY: Not Relevant ( i i ) MOLECULE TYPE: protein ( v i ) ORIGINAL SOURCE:
        ( A ) ORGANISM: Homo sapiens
        ( B ) STRAIN: BRCA1

( v i i i ) POSITION IN GENOME:
        ( A ) CHROMOSOME/SEGMENT: 17
        ( B ) MAP POSITION: 17q21

( x i ) SEQUENCE DESCRIPTION: SEQ ID NO:2:

```
Met Asp Leu Ser Ala Leu Arg Val Glu Glu Val Gln Asn Val Ile Asn
 1               5                  10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
           100                 105                 110
```

-continued

| | | | | | | | | | | | | | | |
|---|---|---|---|---|---|---|---|---|---|---|---|---|---|---|
| Asn | Ser | Pro 115 | Glu | His | Leu | Lys | Asp 120 | Glu | Val | Ser | Ile | Ile 125 | Gln | Ser | Met |
| Gly | Tyr 130 | Arg | Asn | Arg | Ala | Lys 135 | Arg | Leu | Leu | Gln | Ser 140 | Glu | Pro | Glu | Asn |
| Pro 145 | Ser | Leu | Gln | Glu | Thr 150 | Ser | Leu | Ser | Val | Gln 155 | Leu | Ser | Asn | Leu | Gly 160 |
| Thr | Val | Arg | Thr | Leu 165 | Arg | Thr | Lys | Gln | Arg 170 | Ile | Gln | Pro | Gln | Lys 175 | Thr |
| Ser | Val | Tyr | Ile 180 | Glu | Leu | Gly | Ser | Asp 185 | Ser | Ser | Glu | Asp | Thr 190 | Val | Asn |
| Lys | Ala | Thr 195 | Tyr | Cys | Ser | Val | Gly 200 | Asp | Gln | Glu | Leu | Leu 205 | Gln | Ile | Thr |
| Pro | Gln 210 | Gly | Thr | Arg | Asp | Glu 215 | Ile | Ser | Leu | Asp | Ser 220 | Ala | Lys | Lys | Ala |
| Ala 225 | Cys | Glu | Phe | Ser | Glu 230 | Thr | Asp | Val | Thr | Asn 235 | Thr | Glu | His | His | Gln 240 |
| Pro | Ser | Asn | Asn | Asp 245 | Leu | Asn | Thr | Thr | Glu 250 | Lys | Arg | Ala | Ala | Glu 255 | Arg |
| His | Pro | Glu | Lys 260 | Tyr | Gln | Gly | Ser | Ser 265 | Val | Ser | Asn | Leu | His 270 | Val | Glu |
| Pro | Cys | Gly 275 | Thr | Asn | Thr | His | Ala 280 | Ser | Ser | Leu | Gln | His 285 | Glu | Asn | Ser |
| Ser | Leu 290 | Leu | Leu | Thr | Lys | Asp 295 | Arg | Met | Asn | Val | Glu 300 | Lys | Ala | Glu | Phe |
| Cys 305 | Asn | Lys | Ser | Lys | Gln 310 | Pro | Gly | Leu | Ala | Arg 315 | Ser | Gln | His | Asn | Arg 320 |
| Trp | Ala | Gly | Ser | Lys 325 | Glu | Thr | Cys | Asn | Asp 330 | Arg | Arg | Thr | Pro | Ser 335 | Thr |
| Glu | Lys | Lys | Val 340 | Asp | Leu | Asn | Ala | Asp 345 | Pro | Leu | Cys | Glu | Arg 350 | Lys | Glu |
| Trp | Asn | Lys 355 | Gln | Lys | Leu | Pro | Cys 360 | Ser | Glu | Asn | Pro | Arg 365 | Asp | Thr | Glu |
| Asp | Val 370 | Pro | Trp | Ile | Thr | Leu 375 | Asn | Ser | Ser | Ile | Gln 380 | Lys | Val | Asn | Glu |
| Trp 385 | Phe | Ser | Arg | Ser | Asp 390 | Glu | Leu | Leu | Gly | Ser 395 | Asp | Asp | Ser | His | Asp 400 |
| Gly | Glu | Ser | Glu | Ser 405 | Asn | Ala | Lys | Val | Ala 410 | Asp | Val | Leu | Asp | Val 415 | Leu |
| Asn | Glu | Val | Asp 420 | Glu | Tyr | Ser | Gly | Ser 425 | Ser | Glu | Lys | Ile | Asp 430 | Leu | Leu |
| Ala | Ser | Asp | Pro 435 | His | Glu | Ala | Leu | Ile 440 | Cys | Lys | Ser | Glu | Arg 445 | Val | His |
| Ser | Lys 450 | Ser | Val | Glu | Ser | Asn 455 | Ile | Glu | Asp | Lys | Ile 460 | Phe | Gly | Lys | Thr |
| Tyr 465 | Arg | Lys | Lys | Ala | Ser 470 | Leu | Pro | Asn | Leu | Ser 475 | His | Val | Thr | Glu | Asn 480 |
| Leu | Ile | Ile | Gly | Ala 485 | Phe | Val | Thr | Glu | Pro 490 | Gln | Ile | Ile | Gln | Glu 495 | Arg |
| Pro | Leu | Thr | Asn 500 | Lys | Leu | Lys | Arg | Lys 505 | Arg | Arg | Pro | Thr | Ser 510 | Gly | Leu |
| His | Pro | Glu 515 | Asp | Phe | Ile | Lys | Lys 520 | Ala | Asp | Leu | Ala | Val 525 | Gln | Lys | Thr |
| Pro | Glu 530 | Met | Ile | Asn | Gln | Gly 535 | Thr | Asn | Gln | Thr | Glu 540 | Gln | Asn | Gly | Gln |

```
Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Thr Arg His Ile His Ala Leu Glu
610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
    755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
850                 855                 860

Lys Arg Gln Ser Phe Ala Leu Phe Ser Asn Pro Gly Asn Ala Glu Glu
865                 870                 875                 880

Glu Cys Ala Thr Phe Ser Ala His Ser Gly Ser Leu Lys Lys Gln Ser
            885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
```

```
              965                    970                      975
Pro  Tyr  Arg  Ile  Pro  Pro  Leu  Phe  Pro  Ile  Lys  Ser  Phe  Val  Lys  Thr
                    980                      985                      990
Lys  Cys  Lys  Lys  Asn  Leu  Leu  Glu  Glu  Asn  Phe  Glu  Glu  His  Ser  Met
               995                      1000                     1005
Ser  Pro  Glu  Arg  Glu  Met  Gly  Asn  Glu  Asn  Ile  Pro  Ser  Thr  Val  Ser
          1010                     1015                     1020
Thr  Ile  Ser  Arg  Asn  Asn  Ile  Arg  Glu  Asn  Val  Phe  Lys  Gly  Ala  Ser
1025                     1030                     1035                     1040
Ser  Ser  Asn  Ile  Asn  Glu  Val  Gly  Ser  Ser  Thr  Asn  Glu  Val  Gly  Ser
                    1045                     1050                     1055
Ser  Ile  Asn  Glu  Ile  Gly  Ser  Ser  Asp  Glu  Asn  Ile  Gln  Ala  Glu  Leu
                1060                     1065                     1070
Gly  Arg  Asn  Arg  Gly  Pro  Lys  Leu  Asn  Ala  Met  Leu  Arg  Leu  Gly  Val
               1075                     1080                     1085
Leu  Gln  Pro  Glu  Val  Tyr  Lys  Gln  Ser  Leu  Pro  Gly  Ser  Asn  Cys  Lys
          1090                     1095                     1100
His  Pro  Glu  Ile  Lys  Lys  Gln  Glu  Tyr  Glu  Glu  Val  Val  Gln  Thr  Val
1105                     1110                     1115                     1120
Asn  Thr  Asp  Phe  Ser  Pro  Tyr  Leu  Ile  Ser  Asp  Asn  Leu  Glu  Gln  Pro
                    1125                     1130                     1135
Met  Gly  Ser  Ser  His  Ala  Ser  Gln  Val  Cys  Ser  Glu  Thr  Pro  Asp  Asp
               1140                     1145                     1150
Leu  Leu  Asp  Asp  Gly  Glu  Ile  Lys  Glu  Asp  Thr  Ser  Phe  Ala  Glu  Asn
          1155                     1160                     1165
Asp  Ile  Lys  Glu  Ser  Ser  Ala  Val  Phe  Ser  Lys  Ser  Val  Gln  Arg  Gly
     1170                     1175                     1180
Glu  Leu  Ser  Arg  Ser  Pro  Ser  Pro  Phe  Thr  His  Thr  His  Leu  Ala  Gln
1185                     1190                     1195                     1200
Gly  Tyr  Arg  Arg  Gly  Ala  Lys  Lys  Leu  Glu  Ser  Ser  Glu  Glu  Asn  Leu
                    1205                     1210                     1215
Ser  Ser  Glu  Asp  Glu  Glu  Leu  Pro  Cys  Phe  Gln  His  Leu  Leu  Phe  Gly
               1220                     1225                     1230
Lys  Val  Asn  Asn  Ile  Pro  Ser  Gln  Ser  Thr  Arg  His  Ser  Thr  Val  Ala
          1235                     1240                     1245
Thr  Glu  Cys  Leu  Ser  Lys  Asn  Thr  Glu  Glu  Asn  Leu  Leu  Ser  Leu  Lys
     1250                     1255                     1260
Asn  Ser  Leu  Asn  Asp  Cys  Ser  Asn  Gln  Val  Ile  Leu  Ala  Lys  Ala  Ser
1265                     1270                     1275                     1280
Gln  Glu  His  His  Leu  Ser  Glu  Glu  Thr  Lys  Cys  Ser  Ala  Ser  Leu  Phe
                    1285                     1290                     1295
Ser  Ser  Gln  Cys  Ser  Glu  Leu  Glu  Asp  Leu  Thr  Ala  Asn  Thr  Asn  Thr
               1300                     1305                     1310
Gln  Asp  Pro  Phe  Leu  Ile  Gly  Ser  Ser  Lys  Gln  Met  Arg  His  Gln  Ser
          1315                     1320                     1325
Glu  Ser  Gln  Gly  Val  Gly  Leu  Ser  Asp  Lys  Glu  Leu  Val  Ser  Asp  Asp
     1330                     1335                     1340
Glu  Glu  Arg  Gly  Thr  Gly  Leu  Glu  Glu  Asn  Asn  Gln  Glu  Glu  Gln  Ser
1345                     1350                     1355                     1360
Met  Asp  Ser  Asn  Leu  Gly  Glu  Ala  Ala  Ser  Gly  Cys  Glu  Ser  Glu  Thr
                    1365                     1370                     1375
Ser  Val  Ser  Glu  Asp  Cys  Ser  Gly  Leu  Ser  Ser  Gln  Ser  Asp  Ile  Leu
               1380                     1385                     1390
```

```
Thr Thr Gln Gln Arg Asp Thr Met Gln His Asn Leu Ile Lys Leu Gln
        1395                1400                1405
Gln Glu Met Ala Glu Leu Glu Ala Val Leu Glu Gln His Gly Ser Gln
    1410                1415                1420
Pro Ser Asn Ser Tyr Pro Ser Ile Ile Ser Asp Ser Ser Ala Leu Glu
1425                1430                1435                1440
Asp Leu Arg Asn Pro Glu Gln Ser Thr Ser Glu Lys Ala Val Leu Thr
            1445                1450                1455
Ser Gln Lys Ser Ser Glu Tyr Pro Ile Ser Gln Asn Pro Glu Gly Leu
        1460                1465                1470
Ser Ala Asp Lys Phe Glu Val Ser Ala Asp Ser Ser Thr Ser Lys Asn
    1475                1480                1485
Lys Glu Pro Gly Val Glu Arg Ser Ser Pro Ser Lys Cys Pro Ser Leu
    1490                1495                1500
Asp Asp Arg Trp Tyr Met His Ser Cys Ser Gly Ser Leu Gln Asn Arg
1505                1510                1515                1520
Asn Tyr Pro Ser Gln Glu Glu Leu Ile Lys Val Val Asp Val Glu Glu
            1525                1530                1535
Gln Gln Leu Glu Glu Ser Gly Pro His Asp Leu Thr Glu Thr Ser Tyr
        1540                1545                1550
Leu Pro Arg Gln Asp Leu Glu Gly Thr Pro Tyr Leu Glu Ser Gly Ile
        1555                1560                1565
Ser Leu Phe Ser Asp Asp Pro Glu Ser Asp Pro Ser Glu Asp Arg Ala
    1570                1575                1580
Pro Glu Ser Ala Arg Val Gly Asn Ile Pro Ser Ser Thr Ser Ala Leu
1585                1590                1595                1600
Lys Val Pro Gln Leu Lys Val Ala Glu Ser Ala Gln Gly Pro Ala Ala
            1605                1610                1615
Ala His Thr Thr Asp Thr Ala Gly Tyr Asn Ala Met Glu Glu Ser Val
            1620                1625                1630
Ser Arg Glu Lys Pro Glu Leu Thr Ala Ser Thr Glu Arg Val Asn Lys
    1635                1640                1645
Arg Met Ser Met Val Val Ser Gly Leu Thr Pro Glu Glu Phe Met Leu
    1650                1655                1660
Val Tyr Lys Phe Ala Arg Lys His His Ile Thr Leu Thr Asn Leu Ile
1665                1670                1675                1680
Thr Glu Glu Thr Thr His Val Val Met Lys Thr Asp Ala Glu Phe Val
                1685                1690                1695
Cys Glu Arg Thr Leu Lys Tyr Phe Leu Gly Ile Ala Gly Gly Lys Trp
        1700                1705                1710
Val Val Ser Tyr Phe Trp Val Thr Gln Ser Ile Lys Glu Arg Lys Met
        1715                1720                1725
Leu Asn Glu His Asp Phe Glu Val Arg Gly Asp Val Val Asn Gly Arg
    1730                1735                1740
Asn His Gln Gly Pro Lys Arg Ala Arg Glu Ser Gln Asp Arg Lys Ile
1745                1750                1755                1760
Phe Arg Gly Leu Glu Ile Cys Cys Tyr Gly Pro Phe Thr Asn Met Pro
            1765                1770                1775
Thr Asp Gln Leu Glu Trp Met Val Gln Leu Cys Gly Ala Ser Val Val
        1780                1785                1790
Lys Glu Leu Ser Ser Phe Thr Leu Gly Thr Gly Val His Pro Ile Val
        1795                1800                1805
Val Val Gln Pro Asp Ala Trp Thr Glu Asp Asn Gly Phe His Ala Ile
    1810                1815                1820
```

```
                Gly  Gln  Met  Cys  Glu  Ala  Pro  Val  Val  Thr  Arg  Glu  Trp  Val  Leu  Asp
                1825                 1830                     1835                      1840

Ser  Val  Ala  Leu  Tyr  Gln  Cys  Gln  Glu  Leu  Asp  Thr  Tyr  Leu  Ile  Pro
                                    1845                     1850                      1855

Gln  Ile  Pro  His  Ser  His  Tyr
                               1860
```

( 2 ) INFORMATION FOR SEQ ID NO:3:

( i ) SEQUENCE CHARACTERISTICS:
        ( A ) LENGTH: 5711 base pairs
        ( B ) TYPE: nucleic acid
        ( C ) STRANDEDNESS: Not Relevant
        ( D ) TOPOLOGY: linear ( i i ) MOLECULE TYPE: cDNA ( v i ) ORIGINAL SOURCE:
        ( A ) ORGANISM: Homo sapiens
        ( B ) STRAIN: BRCA1

( v i i i ) POSITION IN GENOME:
        ( A ) CHROMOSOME/SEGMENT: 17
        ( B ) MAP POSITION: 17q21

( x i ) SEQUENCE DESCRIPTION: SEQ ID NO:3:

```
AGCTCGCTGA  GACTTCCTGG  ACCCCGCACC  AGGCTGTGGG  GTTTCTCAGA  TAACTGGGCC    60
CCTGCGCTCA  GGAGGCCTTC  ACCCTCTGCT  CTGGGTAAAG  TTCATTGGAA  CAGAAAGAAA   120
TGGATTTATC  TGCTCTTCGC  GTTGAAGAAG  TACAAAATGT  CATTAATGCT  ATGCAGAAAA   180
TCTTAGAGTG  TCCCATCTGT  CTGGAGTTGA  TCAAGGAACC  TGTCTCCACA  AAGTGTGACC   240
ACATATTTTG  CAAATTTTGC  ATGCTGAAAC  TTCTCAACCA  GAAGAAAGGG  CCTTCACAGT   300
GTCCTTTATG  TAAGAATGAT  ATAACCAAAA  GGAGCCTACA  AGAAAGTACG  AGATTTAGTC   360
AACTTGTTGA  AGAGCTATTG  AAAATCATTT  GTGCTTTTCA  GCTTGACACA  GGTTTGGAGT   420
ATGCAAACAG  CTATAATTTT  GCAAAAAAGG  AAAATAACTC  TCCTGAACAT  CTAAAAGATG   480
AAGTTTCTAT  CATCCAAAGT  ATGGGCTACA  GAAACCGTGC  CAAAAGACTT  CTACAGAGTG   540
AACCCGAAAA  TCCTTCCTTG  CAGGAAACCA  GTCTCAGTGT  CCAACTCTCT  AACCTTGGAA   600
CTGTGAGAAC  TCTGAGGACA  AAGCAGCGGA  TACAACCTCA  AAAGACGTCT  GTCTACATTG   660
AATTGGGATC  TGATTCTTCT  GAAGATACCG  TTAATAAGGC  AACTTATTGC  AGTGTGGGAG   720
ATCAAGAATT  GTTACAAATC  ACCCCTCAAG  GAACCAGGGA  TGAAATCAGT  TTGGATTCTG   780
CAAAAAAGGC  TGCTTGTGAA  TTTTCTGAGA  CGGATGTAAC  AAATACTGAA  CATCATCAAC   840
CCAGTAATAA  TGATTTGAAC  ACCACTGAGA  AGCGTGCAGC  TGAGAGGCAT  CCAGAAAAGT   900
ATCAGGGTAG  TTCTGTTTCA  AACTTGCATG  TGGAGCCATG  TGGCACAAAT  ACTCATGCCA   960
GCTCATTACA  GCATGAGAAC  AGCAGTTTAT  TACTCACTAA  AGACAGAATG  AATGTAGAAA  1020
AGGCTGAATT  CTGTAATAAA  AGCAAACAGC  CTGGCTTAGC  AAGGAGCCAA  CATAACAGAT  1080
GGGCTGGAAG  TAAGGAAACA  TGTAATGATA  GGCGGACTCC  CAGCACAGAA  AAAAGGTAG   1140
ATCTGAATGC  TGATCCCCTG  TGTGAGAGAA  AGAATGGAA   TAAGCAGAAA  CTGCCATGCT  1200
CAGAGAATCC  TAGAGATACT  GAAGATGTTC  CTTGGATAAC  ACTAAATAGC  AGCATTCAGA  1260
AAGTTAATGA  GTGGTTTTCC  AGAAGTGATG  AACTGTTAGG  TTCTGATGAC  TCACATGATG  1320
GGGAGTCTGA  ATCAAATGCC  AAAGTAGCTG  ATGTATTGGA  CGTTCTAAAT  GAGGTAGATG  1380
AATATTCTGG  TTCTTCAGAG  AAAATAGACT  TACTGGCCAG  TGATCCTCAT  GAGGCTTTAA  1440
TATGTAAAAG  TGAAAGAGTT  CACTCCAAAT  CAGTAGAGAG  TAATATTGAA  GACAAAATAT  1500
```

```
TTGGGAAAAC CTATCGGAAG AAGGCAAGCC TCCCCAACTT AAGCCATGTA ACTGAAAATC      1560

TAATTATAGG AGCATTTGTT ACTGAGCCAC AGATAATACA AGAGCGTCCC CTCACAAATA      1620

AATTAAAGCG TAAAAGGAGA CCTACATCAG GCCTTCATCC TGAGGATTTT ATCAAGAAAG      1680

CAGATTTGGC AGTTCAAAAG ACTCCTGAAA TGATAAATCA GGGAACTAAC CAAACGGAGC      1740

AGAATGGTCA AGTGATGAAT ATTACTAATA GTGGTCATGA GAATAAAACA AAAGGTGATT      1800

CTATTCAGAA TGAGAAAAAT CCTAACCCAA TAGAATCACT CGAAAAAGAA TCTGCTTTCA      1860

AAACGAAAGC TGAACCTATA AGCAGCAGTA TAAGCAATAT GGAACTCGAA TTAAATATCC      1920

ACAATTCAAA AGCACCTAAA AAGAATAGGC TGAGGAGGAA GTCTTCTACC AGGCATATTC      1980

ATGCGCTTGA ACTAGTAGTC AGTAGAAATC TAAGCCCACC TAATTGTACT GAATTGCAAA      2040

TTGATAGTTG TTCTAGCAGT GAAGAGATAA AGAAAAAAA GTACAACCAA ATGCCAGTCA       2100

GGCACAGCAG AAACCTACAA CTCATGGAAG GTAAAGAACC TGCAACTGGA GCCAAGAAGA      2160

GTAACAAGCC AAATGAACAG ACAAGTAAAA GACATGACAG CGATACTTTC CCAGAGCTGA      2220

AGTTAACAAA TGCACCTGGT TCTTTTACTA AGTGTTCAAA TACCAGTGAA CTTAAAGAAT      2280

TTGTCAATCC TAGCCTTCCA AGAGAAGAAA AAGAAGAGAA ACTAGAAACA GTTAAAGTGT      2340

CTAATAATGC TGAAGACCCC AAAGATCTCA TGTTAAGTGG AGAAAGGGTT TTGCAAACTG      2400

AAAGATCTGT AGAGAGTAGC AGTATTTCAT GGTACCTGG TACTGATTAT GGCACTCAGG       2460

AAAGTATCTC GTTACTGGAA GTTAGCACTC TAGGGAAGGC AAAAACAGAA CCAAATAAAT      2520

GTGTGAGTCA GTGTGCAGCA TTTGAAAACC CCAAGGGACT AATTCATGGT TGTTCCAAAG      2580

ATAATAGAAA TGACACAGAA GGCTTTAAGT ATCCATTGGG ACATGAAGTT AACCACAGTC      2640

GGGAAACAAG CATAGAAATG GAAGAAAGTG AACTTGATGC TCAGTATTTG CAGAATACAT      2700

TCAAGGTTTC AAAGCGCCAG TCATTTGCTC TGTTTTCAAA TCCAGGAAAT GCAGAAGAGG      2760

AATGTGCAAC ATTCTCTGCC CACTCTGGGT CCTTAAAGAA ACAAAGTCCA AAAGTCACTT      2820

TTGAATGTGA ACAAAAGGAA GAAAATCAAG GAAAGAATGA GTCTAATATC AAGCCTGTAC      2880

AGACAGTTAA TATCACTGCA GGCTTTCCTG TGGTTGGTCA GAAAGATAAG CCAGTTGATA      2940

ATGCCAAATG TAGTATCAAA GGAGGCTCTA GGTTTTGTCT ATCATCTCAG TTCAGAGGCA      3000

ACGAAACTGG ACTCATTACT CCAAATAAAC ATGGACTTTT ACAAAACCCA ATCGTATAC      3060

CACCACTTTT TCCCATCAAG TCATTTGTTA AAACTAAATG TAAGAAAAAT CTGCTAGAGG      3120

AAAACTTTGA GGAACATTCA ATGTCACCTG AAAGAGAAAT GGGAAATGAG AACATTCCAA      3180

GTACAGTGAG CACAATTAGC CGTAATAACA TTAGAGAAAA TGTTTTTAAA GAAGCCAGCT      3240

CAAGCAATAT TAATGAAGTA GGTTCCAGTA CTAATGAAGT GGGCTCCAGT ATTAATGAAA      3300

TAGGTTCCAG TGATGAAAAC ATTCAAGCAG AACTAGGTAG AAACAGAGGG CCAAAATTGA      3360

ATGCTATGCT TAGATTAGGG GTTTTGCAAC CTGAGGTCTA TAAACAAAGT CTTCCTGGAA      3420

GTAATTGTAA GCATCCTGAA ATAAAAAGC AAGAATATGA AGAAGTAGTT CAGACTGTTA       3480

ATACAGATTT CTCTCCATAT CTGATTTCAG ATAACTTAGA ACAGCCTATG GGAAGTAGTC      3540

ATGCATCTCA GGTTTGTTCT GAGACACCTG ATGACCTGTT AGATGATGGT GAAATAAAGG      3600

AAGATACTAG TTTTGCTGAA AATGACATTA AGGAAGTTC TGCTGTTTT AGCAAAAGCG        3660

TCCAGAAAGG AGAGCTTAGC AGGAGTCCTA GCCCTTTCAC CCATACACAT TTGGCTCAGG      3720

GTTACCGAAG AGGGGCCAAG AAATTAGAGT CCTCAGAAGA GAACTTATCT AGTGAGGATG      3780

AAGAGCTTCC CTGCTTCCAA CACTTGTTAT TTGGTAAAGT AAACAATATA CCTTCTCAGT      3840

CTACTAGGCA TAGCACCGTT GCTACCGAGT GTCTGTCTAA GAACACAGAG GAGAATTTAT      3900
```

-continued

```
TATCATTGAA GAATAGCTTA AATGACTGCA GTAACCAGGT AATATTGGCA AAGGCATCTC   3960
AGGAACATCA CCTTAGTGAG GAAACAAAAT GTTCTGCTAG CTTGTTTTCT TCACAGTGCA   4020
GTGAATTGGA AGACTTGACT GCAAATACAA ACACCCAGGA TCCTTTCTTG ATTGGTTCTT   4080
CCAAACAAAT GAGGCATCAG TCTGAAAGCC AGGGAGTTGG TCTGAGTGAC AAGGAATTGG   4140
TTTCAGATGA TGAAGAAAGA GGAACGGGCT TGGAAGAAAA TAATCAAGAA GAGCAAAGCA   4200
TGGATTCAAA CTTAGGTGAA GCAGCATCTG GGTGTGAGAG TGAAACAAGC GTCTCTGAAG   4260
ACTGCTCAGG GCTATCCTCT CAGAGTGACA TTTTAACCAC TCAGCAGAGG GATACCATGC   4320
AACATAACCT GATAAAGCTC CAGCAGGAAA TGGCTGAACT AGAAGCTGTG TTAGAACAGC   4380
ATGGGAGCCA GCCTTCTAAC AGCTACCCTT CCATCATAAG TGACTCTTCT GCCCTTGAGG   4440
ACCTGCGAAA TCCAGAACAA AGCACATCAG AAAAAGCAGT ATTAACTTCA CAGAAAAGTA   4500
GTGAATACCC TATAAGCCAG AATCCAGAAG GCCTTTCTGC TGACAAGTTT GAGGTGTCTG   4560
CAGATAGTTC TACCAGTAAA AATAAAGAAC CAGGAGTGGA AAGGTCATCC CCTTCTAAAT   4620
GCCCATCATT AGATGATAGG TGGTACATGC ACAGTTGCTC TGGGAGTCTT CAGAATAGAA   4680
ACTACCCATC TCAAGAGGAG CTCATTAAGG TTGTTGATGT GGAGGAGCAA CAGCTGGAAG   4740
AGTCTGGGCC ACACGATTTG ACGGAAACAT CTTACTTGCC AAGGCAAGAT CTAGAGGGAA   4800
CCCCTTACCT GGAATCTGGA ATCAGCCTCT TCTCTGATGA CCCTGAATCT GATCCTTCTG   4860
AAGACAGAGC CCCAGAGTCA GCTCGTGTTG GCAACATACC ATCTTCAACC TCTGCATTGA   4920
AAGTTCCCCA ATTGAAAGTT GCAGAATCTG CCCAGAGTCC AGCTGCTGCT CATACTACTG   4980
ATACTGCTGG GTATAATGCA ATGGAAGAAA GTGTGAGCAG GGAGAAGCCA GAATTGACAG   5040
CTTCAACAGA AAGGGTCAAC AAAAGAATGT CCATGGTGGT GTCTGGCCTG ACCCCAGAAG   5100
AATTTATGCT CGTGTACAAG TTTGCCAGAA AACACCACAT CACTTTAACT AATCTAATTA   5160
CTGAAGAGAC TACTCATGTT GTTATGAAAA CAGATGCTGA GTTTGTGTGT GAACGGACAC   5220
TGAAATATTT TCTAGGAATT GCGGGAGGAA AATGGGTAGT TAGCTATTTC TGGGTGACCC   5280
AGTCTATTAA AGAAAGAAAA ATGCTGAATG AGCATGATTT TGAAGTCAGA GGAGATGTGG   5340
TCAATGGAAG AAACCACCAA GGTCCAAAGC GAGCAAGAGA ATCCAGGAC AGAAAGATCT   5400
TCAGGGGGCT AGAAATCTGT TGCTATGGGC CCTTCACCAA CATGCCCACA GATCAACTGG   5460
AATGGATGGT ACAGCTGTGT GGTGCTTCTG TGGTGAAGGA GCTTTCATCA TTCACCCTTG   5520
GCACAGGTGT CCACCCAATT GTGGTTGTGC AGCCAGATGC CTGGACAGAG GACAATGGCT   5580
TCCATGCAAT TGGGCAGATG TGTGAGGCAC CTGTGGTGAC CCGAGAGTGG GTGTTGGACA   5640
GTGTAGCACT CTACCAGTGC CAGGAGCTGG ACACCTACCT GATACCCCAG ATCCCCCACA   5700
GCCACTACTG A                                                       5711
```

( 2 ) INFORMATION FOR SEQ ID NO:4:

( i ) SEQUENCE CHARACTERISTICS:
        ( A ) LENGTH: 1863 amino acids
        ( B ) TYPE: amino acid
        ( C ) STRANDEDNESS: Not Relevant
        ( D ) TOPOLOGY: Not Relevant ( i i ) MOLECULE TYPE: protein ( v i ) ORIGINAL SOURCE:
        ( A ) ORGANISM: Homo sapiens
        ( B ) STRAIN: BRCA1

( v i i i ) POSITION IN GENOME:
        ( A ) CHROMOSOME/SEGMENT: 17

( B ) MAP POSITION: 17q21

( x i ) SEQUENCE DESCRIPTION: SEQ ID NO:4:

```
Met Asp Leu Ser Ala Leu Arg Val Glu Glu Val Gln Asn Val Ile Asn
 1               5                  10                  15
Ala Met Gln Lys Ile Leu Glu Cys Pro Ile Cys Leu Glu Leu Ile Lys
            20                  25                  30
Glu Pro Val Ser Thr Lys Cys Asp His Ile Phe Cys Lys Phe Cys Met
        35                  40                  45
Leu Lys Leu Leu Asn Gln Lys Lys Gly Pro Ser Gln Cys Pro Leu Cys
    50                  55                  60
Lys Asn Asp Ile Thr Lys Arg Ser Leu Gln Glu Ser Thr Arg Phe Ser
65                  70                  75                  80
Gln Leu Val Glu Glu Leu Leu Lys Ile Ile Cys Ala Phe Gln Leu Asp
            85                  90                  95
Thr Gly Leu Glu Tyr Ala Asn Ser Tyr Asn Phe Ala Lys Lys Glu Asn
        100                 105                 110
Asn Ser Pro Glu His Leu Lys Asp Glu Val Ser Ile Ile Gln Ser Met
    115                 120                 125
Gly Tyr Arg Asn Arg Ala Lys Arg Leu Leu Gln Ser Glu Pro Glu Asn
130                 135                 140
Pro Ser Leu Gln Glu Thr Ser Leu Ser Val Gln Leu Ser Asn Leu Gly
145                 150                 155                 160
Thr Val Arg Thr Leu Arg Thr Lys Gln Arg Ile Gln Pro Gln Lys Thr
            165                 170                 175
Ser Val Tyr Ile Glu Leu Gly Ser Asp Ser Ser Glu Asp Thr Val Asn
        180                 185                 190
Lys Ala Thr Tyr Cys Ser Val Gly Asp Gln Glu Leu Leu Gln Ile Thr
    195                 200                 205
Pro Gln Gly Thr Arg Asp Glu Ile Ser Leu Asp Ser Ala Lys Lys Ala
210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
            245                 250                 255
His Pro Glu Lys Tyr Gln Gly Ser Ser Val Ser Asn Leu His Val Glu
        260                 265                 270
Pro Cys Gly Thr Asn Thr His Ala Ser Ser Leu Gln His Glu Asn Ser
    275                 280                 285
Ser Leu Leu Leu Thr Lys Asp Arg Met Asn Val Glu Lys Ala Glu Phe
290                 295                 300
Cys Asn Lys Ser Lys Gln Pro Gly Leu Ala Arg Ser Gln His Asn Arg
305                 310                 315                 320
Trp Ala Gly Ser Lys Glu Thr Cys Asn Asp Arg Arg Thr Pro Ser Thr
            325                 330                 335
Glu Lys Lys Val Asp Leu Asn Ala Asp Pro Leu Cys Glu Arg Lys Glu
        340                 345                 350
Trp Asn Lys Gln Lys Leu Pro Cys Ser Glu Asn Pro Arg Asp Thr Glu
    355                 360                 365
Asp Val Pro Trp Ile Thr Leu Asn Ser Ser Ile Gln Lys Val Asn Glu
370                 375                 380
Trp Phe Ser Arg Ser Asp Glu Leu Leu Gly Ser Asp Asp Ser His Asp
385                 390                 395                 400
Gly Glu Ser Glu Ser Asn Ala Lys Val Ala Asp Val Leu Asp Val Leu
```

-continued

|  |  |  | 405 |  |  |  |  | 410 |  |  |  |  | 415 |  |
|---|---|---|---|---|---|---|---|---|---|---|---|---|---|---|
| Asn | Glu | Val | Asp | Glu | Tyr | Ser | Gly | Ser | Ser | Glu | Lys | Ile | Asp | Leu | Leu |
|  |  |  | 420 |  |  |  |  | 425 |  |  |  |  | 430 |  |
| Ala | Ser | Asp | Pro | His | Glu | Ala | Leu | Ile | Cys | Lys | Ser | Glu | Arg | Val | His |
|  |  | 435 |  |  |  |  | 440 |  |  |  |  | 445 |  |  |
| Ser | Lys | Ser | Val | Glu | Ser | Asn | Ile | Glu | Asp | Lys | Ile | Phe | Gly | Lys | Thr |
|  | 450 |  |  |  |  | 455 |  |  |  |  | 460 |  |  |  |
| Tyr | Arg | Lys | Lys | Ala | Ser | Leu | Pro | Asn | Leu | Ser | His | Val | Thr | Glu | Asn |
| 465 |  |  |  |  | 470 |  |  |  |  | 475 |  |  |  |  | 480 |
| Leu | Ile | Ile | Gly | Ala | Phe | Val | Thr | Glu | Pro | Gln | Ile | Ile | Gln | Glu | Arg |
|  |  |  |  | 485 |  |  |  |  | 490 |  |  |  |  | 495 |  |
| Pro | Leu | Thr | Asn | Lys | Leu | Lys | Arg | Lys | Arg | Arg | Pro | Thr | Ser | Gly | Leu |
|  |  |  | 500 |  |  |  |  | 505 |  |  |  |  | 510 |  |
| His | Pro | Glu | Asp | Phe | Ile | Lys | Lys | Ala | Asp | Leu | Ala | Val | Gln | Lys | Thr |
|  |  | 515 |  |  |  |  | 520 |  |  |  |  | 525 |  |  |
| Pro | Glu | Met | Ile | Asn | Gln | Gly | Thr | Asn | Gln | Thr | Glu | Gln | Asn | Gly | Gln |
|  |  | 530 |  |  |  |  | 535 |  |  |  |  | 540 |  |  |
| Val | Met | Asn | Ile | Thr | Asn | Ser | Gly | His | Glu | Asn | Lys | Thr | Lys | Gly | Asp |
| 545 |  |  |  |  | 550 |  |  |  |  | 555 |  |  |  |  | 560 |
| Ser | Ile | Gln | Asn | Glu | Lys | Asn | Pro | Asn | Pro | Ile | Glu | Ser | Leu | Glu | Lys |
|  |  |  |  | 565 |  |  |  |  | 570 |  |  |  |  | 575 |  |
| Glu | Ser | Ala | Phe | Lys | Thr | Lys | Ala | Glu | Pro | Ile | Ser | Ser | Ser | Ile | Ser |
|  |  |  | 580 |  |  |  |  | 585 |  |  |  |  | 590 |  |
| Asn | Met | Glu | Leu | Glu | Leu | Asn | Ile | His | Asn | Ser | Lys | Ala | Pro | Lys | Lys |
|  |  | 595 |  |  |  |  | 600 |  |  |  |  | 605 |  |  |
| Asn | Arg | Leu | Arg | Arg | Lys | Ser | Thr | Arg | His | Ile | His | Ala | Leu | Glu |
|  | 610 |  |  |  |  | 615 |  |  |  |  | 620 |  |  |  |
| Leu | Val | Val | Ser | Arg | Asn | Leu | Ser | Pro | Pro | Asn | Cys | Thr | Glu | Leu | Gln |
| 625 |  |  |  |  | 630 |  |  |  |  | 635 |  |  |  |  | 640 |
| Ile | Asp | Ser | Cys | Ser | Ser | Ser | Glu | Glu | Ile | Lys | Lys | Lys | Lys | Tyr | Asn |
|  |  |  |  | 645 |  |  |  |  | 650 |  |  |  |  | 655 |  |
| Gln | Met | Pro | Val | Arg | His | Ser | Arg | Asn | Leu | Gln | Leu | Met | Glu | Gly | Lys |
|  |  |  | 660 |  |  |  |  | 665 |  |  |  |  | 670 |  |
| Glu | Pro | Ala | Thr | Gly | Ala | Lys | Lys | Ser | Asn | Lys | Pro | Asn | Glu | Gln | Thr |
|  |  |  | 675 |  |  |  |  | 680 |  |  |  |  | 685 |  |
| Ser | Lys | Arg | His | Asp | Ser | Asp | Thr | Phe | Pro | Glu | Leu | Lys | Leu | Thr | Asn |
|  | 690 |  |  |  |  | 695 |  |  |  |  | 700 |  |  |  |
| Ala | Pro | Gly | Ser | Phe | Thr | Lys | Cys | Ser | Asn | Thr | Ser | Glu | Leu | Lys | Glu |
| 705 |  |  |  |  | 710 |  |  |  |  | 715 |  |  |  |  | 720 |
| Phe | Val | Asn | Pro | Ser | Leu | Pro | Arg | Glu | Glu | Lys | Glu | Glu | Lys | Leu | Glu |
|  |  |  |  | 725 |  |  |  |  | 730 |  |  |  |  | 735 |  |
| Thr | Val | Lys | Val | Ser | Asn | Asn | Ala | Glu | Asp | Pro | Lys | Asp | Leu | Met | Leu |
|  |  |  | 740 |  |  |  |  | 745 |  |  |  |  | 750 |  |
| Ser | Gly | Glu | Arg | Val | Leu | Gln | Thr | Glu | Arg | Ser | Val | Glu | Ser | Ser | Ser |
|  |  | 755 |  |  |  |  | 760 |  |  |  |  | 765 |  |  |
| Ile | Ser | Leu | Val | Pro | Gly | Thr | Asp | Tyr | Gly | Thr | Gln | Glu | Ser | Ile | Ser |
|  | 770 |  |  |  |  | 775 |  |  |  |  | 780 |  |  |  |
| Leu | Leu | Glu | Val | Ser | Thr | Leu | Gly | Lys | Ala | Lys | Thr | Glu | Pro | Asn | Lys |
| 785 |  |  |  | 790 |  |  |  |  | 795 |  |  |  |  |  | 800 |
| Cys | Val | Ser | Gln | Cys | Ala | Ala | Phe | Glu | Asn | Pro | Lys | Gly | Leu | Ile | His |
|  |  |  |  | 805 |  |  |  |  | 810 |  |  |  |  | 815 |  |
| Gly | Cys | Ser | Lys | Asp | Asn | Arg | Asn | Asp | Thr | Glu | Gly | Phe | Lys | Tyr | Pro |
|  |  |  | 820 |  |  |  |  | 825 |  |  |  |  | 830 |  |

```
Leu Gly His Glu Val Asn His Ser Arg Glu Thr Ser Ile Glu Met Glu
        835                 840                 845
Glu Ser Glu Leu Asp Ala Gln Tyr Leu Gln Asn Thr Phe Lys Val Ser
    850                 855                 860
Lys Arg Gln Ser Phe Ala Leu Phe Ser Asn Pro Gly Asn Ala Glu Glu
865                 870                 875                 880
Glu Cys Ala Thr Phe Ser Ala His Ser Gly Ser Leu Lys Lys Gln Ser
                885                 890                 895
Pro Lys Val Thr Phe Glu Cys Glu Lys Glu Asn Gln Gly Lys
            900                 905                 910
Asn Glu Ser Asn Ile Lys Pro Val Gln Thr Val Asn Ile Thr Ala Gly
        915                 920                 925
Phe Pro Val Val Gly Gln Lys Asp Lys Pro Val Asp Asn Ala Lys Cys
        930                 935                 940
Ser Ile Lys Gly Gly Ser Arg Phe Cys Leu Ser Ser Gln Phe Arg Gly
945                 950                 955                 960
Asn Glu Thr Gly Leu Ile Thr Pro Asn Lys His Gly Leu Leu Gln Asn
                965                 970                 975
Pro Tyr Arg Ile Pro Pro Leu Phe Pro Ile Lys Ser Phe Val Lys Thr
            980                 985                 990
Lys Cys Lys Lys Asn Leu Leu Glu Glu Asn Phe Glu Glu His Ser Met
        995                 1000                1005
Ser Pro Glu Arg Glu Met Gly Asn Glu Asn Ile Pro Ser Thr Val Ser
    1010                1015                1020
Thr Ile Ser Arg Asn Asn Ile Arg Glu Asn Val Phe Lys Glu Ala Ser
1025                1030                1035                1040
Ser Ser Asn Ile Asn Glu Val Gly Ser Ser Thr Asn Glu Val Gly Ser
            1045                1050                1055
Ser Ile Asn Glu Ile Gly Ser Ser Asp Glu Asn Ile Gln Ala Glu Leu
    1060                1065                1070
Gly Arg Asn Arg Gly Pro Lys Leu Asn Ala Met Leu Arg Leu Gly Val
    1075                1080                1085
Leu Gln Pro Glu Val Tyr Lys Gln Ser Leu Pro Gly Ser Asn Cys Lys
    1090                1095                1100
His Pro Glu Ile Lys Lys Gln Glu Tyr Glu Glu Val Val Gln Thr Val
1105                1110                1115                1120
Asn Thr Asp Phe Ser Pro Tyr Leu Ile Ser Asp Asn Leu Glu Gln Pro
            1125                1130                1135
Met Gly Ser Ser His Ala Ser Gln Val Cys Ser Glu Thr Pro Asp Asp
            1140                1145                1150
Leu Leu Asp Asp Gly Glu Ile Lys Glu Asp Thr Ser Phe Ala Glu Asn
        1155                1160                1165
Asp Ile Lys Glu Ser Ser Ala Val Phe Ser Lys Ser Val Gln Lys Gly
        1170                1175                1180
Glu Leu Ser Arg Ser Pro Ser Pro Phe Thr His Thr His Leu Ala Gln
1185                1190                1195                1200
Gly Tyr Arg Arg Gly Ala Lys Lys Leu Glu Ser Ser Glu Glu Asn Leu
            1205                1210                1215
Ser Ser Glu Asp Glu Glu Leu Pro Cys Phe Gln His Leu Leu Phe Gly
            1220                1225                1230
Lys Val Asn Asn Ile Pro Ser Gln Ser Thr Arg His Ser Thr Val Ala
        1235                1240                1245
Thr Glu Cys Leu Ser Lys Asn Thr Glu Glu Asn Leu Leu Ser Leu Lys
    1250                1255                1260
```

```
Asn Ser Leu Asn Asp Cys Ser Asn Gln Val Ile Leu Ala Lys Ala Ser
1265                1270                1275                1280

Gln Glu His His Leu Ser Glu Glu Thr Lys Cys Ser Ala Ser Leu Phe
                     1285                1290                1295

Ser Ser Gln Cys Ser Glu Leu Glu Asp Leu Thr Ala Asn Thr Asn Thr
            1300                1305                1310

Gln Asp Pro Phe Leu Ile Gly Ser Ser Lys Gln Met Arg His Gln Ser
            1315                1320                1325

Glu Ser Gln Gly Val Gly Leu Ser Asp Lys Glu Leu Val Ser Asp Asp
            1330                1335                1340

Glu Glu Arg Gly Thr Gly Leu Glu Glu Asn Asn Gln Glu Glu Gln Ser
1345                1350                1355                1360

Met Asp Ser Asn Leu Gly Glu Ala Ala Ser Gly Cys Glu Ser Glu Thr
                1365                1370                1375

Ser Val Ser Glu Asp Cys Ser Gly Leu Ser Ser Gln Ser Asp Ile Leu
            1380                1385                1390

Thr Thr Gln Gln Arg Asp Thr Met Gln His Asn Leu Ile Lys Leu Gln
            1395                1400                1405

Gln Glu Met Ala Glu Leu Glu Ala Val Leu Glu Gln His Gly Ser Gln
        1410                1415                1420

Pro Ser Asn Ser Tyr Pro Ser Ile Ile Ser Asp Ser Ser Ala Leu Glu
1425                1430                1435                1440

Asp Leu Arg Asn Pro Glu Gln Ser Thr Ser Glu Lys Ala Val Leu Thr
                1445                1450                1455

Ser Gln Lys Ser Ser Glu Tyr Pro Ile Ser Gln Asn Pro Glu Gly Leu
            1460                1465                1470

Ser Ala Asp Lys Phe Glu Val Ser Ala Asp Ser Ser Thr Ser Lys Asn
            1475                1480                1485

Lys Glu Pro Gly Val Glu Arg Ser Ser Pro Ser Lys Cys Pro Ser Leu
        1490                1495                1500

Asp Asp Arg Trp Tyr Met His Ser Cys Ser Gly Ser Leu Gln Asn Arg
1505                1510                1515                1520

Asn Tyr Pro Ser Gln Glu Glu Leu Ile Lys Val Val Asp Val Glu Glu
                1525                1530                1535

Gln Gln Leu Glu Glu Ser Gly Pro His Asp Leu Thr Glu Thr Ser Tyr
            1540                1545                1550

Leu Pro Arg Gln Asp Leu Glu Gly Thr Pro Tyr Leu Glu Ser Gly Ile
            1555                1560                1565

Ser Leu Phe Ser Asp Asp Pro Glu Ser Asp Pro Ser Glu Asp Arg Ala
        1570                1575                1580

Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Ser Pro Ala Ala
                1605                1610                1615

Ala His Thr Thr Asp Thr Ala Gly Tyr Asn Ala Met Glu Glu Ser Val
            1620                1625                1630

Ser Arg Glu Lys Pro Glu Leu Thr Ala Ser Thr Glu Arg Val Asn Lys
            1635                1640                1645

Arg Met Ser Met Val Val Ser Gly Leu Thr Pro Glu Glu Phe Met Leu
        1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
```

|  | 1685 |  |  |  | 1690 |  |  |  | 1695 |  |  |
|---|---|---|---|---|---|---|---|---|---|---|---|
| Cys | Glu | Arg | Thr | Leu | Lys | Tyr | Phe | Leu | Gly | Ile | Ala | Gly | Gly | Lys | Trp |
|  |  |  | 1700 |  |  |  | 1705 |  |  |  | 1710 |
| Val | Val | Ser | Tyr | Phe | Trp | Val | Thr | Gln | Ser | Ile | Lys | Glu | Arg | Lys | Met |
|  |  |  | 1715 |  |  |  | 1720 |  |  |  | 1725 |
| Leu | Asn | Glu | His | Asp | Phe | Glu | Val | Arg | Gly | Asp | Val | Val | Asn | Gly | Arg |
|  | 1730 |  |  |  | 1735 |  |  |  | 1740 |
| Asn | His | Gln | Gly | Pro | Lys | Arg | Ala | Arg | Glu | Ser | Gln | Asp | Arg | Lys | Ile |
| 1745 |  |  |  | 1750 |  |  |  | 1755 |  |  |  | 1760 |
| Phe | Arg | Gly | Leu | Glu | Ile | Cys | Cys | Tyr | Gly | Pro | Phe | Thr | Asn | Met | Pro |
|  |  |  | 1765 |  |  |  | 1770 |  |  |  | 1775 |
| Thr | Asp | Gln | Leu | Glu | Trp | Met | Val | Gln | Leu | Cys | Gly | Ala | Ser | Val | Val |
|  |  |  | 1780 |  |  |  | 1785 |  |  |  | 1790 |
| Lys | Glu | Leu | Ser | Ser | Phe | Thr | Leu | Gly | Thr | Gly | Val | His | Pro | Ile | Val |
|  |  |  | 1795 |  |  |  | 1800 |  |  |  | 1805 |
| Val | Val | Gln | Pro | Asp | Ala | Trp | Thr | Glu | Asp | Asn | Gly | Phe | His | Ala | Ile |
|  | 1810 |  |  |  | 1815 |  |  |  | 1820 |
| Gly | Gln | Met | Cys | Glu | Ala | Pro | Val | Val | Thr | Arg | Glu | Trp | Val | Leu | Asp |
| 1825 |  |  |  | 1830 |  |  |  | 1835 |  |  |  | 1840 |
| Ser | Val | Ala | Leu | Tyr | Gln | Cys | Gln | Glu | Leu | Asp | Thr | Tyr | Leu | Ile | Pro |
|  |  |  | 1845 |  |  |  | 1850 |  |  |  | 1855 |
| Gln | Ile | Pro | His | Ser | His | Tyr |
|  | 1860 |

( 2 ) INFORMATION FOR SEQ ID NO:5:

( i ) SEQUENCE CHARACTERISTICS:
        ( A ) LENGTH: 5711 base pairs
        ( B ) TYPE: nucleic acid
        ( C ) STRANDEDNESS: Not Relevant
        ( D ) TOPOLOGY: linear ( i i ) MOLECULE TYPE: cDNA ( v i ) ORIGINAL SOURCE:
        ( A ) ORGANISM: Homo sapiens
        ( B ) STRAIN: BRCA1

( v i i i ) POSITION IN GENOME:
        ( A ) CHROMOSOME/SEGMENT: 17
        ( B ) MAP POSITION: 17q21

( x i ) SEQUENCE DESCRIPTION: SEQ ID NO:5:

| AGCTCGCTGA | GACTTCCTGG | ACCCCGCACC | AGGCTGTGGG | GTTTCTCAGA | TAACTGGGCC | 60 |
|---|---|---|---|---|---|---|
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAAGGG | CCTTCACAGT | 300 |
| GTCCTTTATG | TAAGAATGAT | ATAACCAAAA | GGAGCCTACA | AGAAAGTACG | AGATTTAGTC | 360 |
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAAGG | AAAATAACTC | TCCTGAACAT | CTAAAAGATG | 480 |
| AAGTTTCTAT | CATCCAAAGT | ATGGGCTACA | GAAACCGTGC | CAAAAGACTT | CTACAGAGTG | 540 |
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAAGACGTCT | GTCTACATTG | 660 |
| AATTGGGATC | TGATTCTTCT | GAAGATACCG | TTAATAAGGC | AACTTATTGC | AGTGTGGGAG | 720 |

-continued

| | | | | | |
|---|---|---|---|---|---|
| ATCAAGAATT | GTTACAAATC | ACCCCTCAAG | GAACCAGGGA | TGAAATCAGT | TTGGATTCTG | 780 |
| CAAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAAGGTAG | 1140 |
| ATCTGAATGC | TGATCCCCTG | TGTGAGAGAA | AGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |
| CAGATTTGGC | AGTTCAAAAG | ACTCCTGAAA | TGATAAATCA | GGGAACTAAC | CAAACGGAGC | 1740 |
| AGAATGGTCA | AGTGATGAAT | ATTACTAATA | GTGGTCATGA | GAATAAAACA | AAAGGTGATT | 1800 |
| CTATTCAGAA | TGAGAAAAAT | CCTAACCCAA | TAGAATCACT | CGAAAAAGAA | TCTGCTTTCA | 1860 |
| AAACGAAAGC | TGAACCTATA | AGCAGCAGTA | TAAGCAATAT | GGAACTCGAA | TTAAATATCC | 1920 |
| ACAATTCAAA | AGCACCTAAA | AAGAATAGGC | TGAGGAGGAA | GTCTTCTACC | AGGCATATTC | 1980 |
| ATGCGCTTGA | ACTAGTAGTC | AGTAGAAATC | TAAGCCCACC | TAATTGTACT | GAATTGCAAA | 2040 |
| TTGATAGTTG | TTCTAGCAGT | GAAGAGATAA | AGAAAAAAA | GTACAACCAA | ATGCCAGTCA | 2100 |
| GGCACAGCAG | AAACCTACAA | CTCATGGAAG | GTAAAGAACC | TGCAACTGGA | GCCAAGAAGA | 2160 |
| GTAACAAGCC | AAATGAACAG | ACAAGTAAAA | GACATGACAG | TGATACTTTC | CCAGAGCTGA | 2220 |
| AGTTAACAAA | TGCACCTGGT | TCTTTTACTA | AGTGTTCAAA | TACCAGTGAA | CTTAAAGAAT | 2280 |
| TTGTCAATCC | TAGCCTTCCA | AGAGAAGAAA | AAGAAGAGAA | ACTAGAAACA | GTTAAAGTGT | 2340 |
| CTAATAATGC | TGAAGACCCC | AAAGATCTCA | TGTTAAGTGG | AGAAAGGGTT | TTGCAAACTG | 2400 |
| AAAGATCTGT | AGAGAGTAGC | AGTATTTCAC | TGGTACCTGG | TACTGATTAT | GGCACTCAGG | 2460 |
| AAAGTATCTC | GTTACTGGAA | GTTAGCACTC | TAGGGAAGGC | AAAAACAGAA | CCAAATAAAT | 2520 |
| GTGTGAGTCA | GTGTGCAGCA | TTTGAAAACC | CCAAGGGACT | AATTCATGGT | TGTTCCAAAG | 2580 |
| ATAATAGAAA | TGACACAGAA | GGCTTTAAGT | ATCCATTGGG | ACATGAAGTT | AACCACAGTC | 2640 |
| GGGAAACAAG | CATAGAAATG | GAAGAAAGTG | AACTTGATGC | TCAGTATTTG | CAGAATACAT | 2700 |
| TCAAGGTTTC | AAAGCGCCAG | TCATTTGCTC | TGTTTTCAAA | TCCAGGAAAT | GCAGAAGAGG | 2760 |
| AATGTGCAAC | ATTCTCTGCC | CACTCTGGGT | CCTTAAAGAA | ACAAAGTCCA | AAAGTCACTT | 2820 |
| TTGAATGTGA | ACAAAAGGAA | GAAAATCAAG | GAAAGAATGA | GTCTAATATC | AAGCCTGTAC | 2880 |
| AGACAGTTAA | TATCACTGCA | GGCTTTCCTG | TGGTTGGTCA | GAAAGATAAG | CCAGTTGATA | 2940 |
| ATGCCAAATG | TAGTATCAAA | GGAGGCTCTA | GGTTTTGTCT | ATCATCTCAG | TTCAGAGGCA | 3000 |
| ACGAAACTGG | ACTCATTACT | CCAAATAAAC | ATGGACTTTT | ACAAAACCCA | TATCGTATAC | 3060 |
| CACCACTTTT | TCCCATCAAG | TCATTTGTTA | AAACTAAATG | TAAGAAAAAT | CTGCTAGAGG | 3120 |

| | | | | | |
|---|---|---|---|---|---|
| AAAACTTTGA | GGAACATTCA | ATGTCACCTG | AAAGAGAAAT | GGGAAATGAG | AACATTCCAA | 3180
| GTACAGTGAG | CACAATTAGC | CGTAATAACA | TTAGAGAAAA | TGTTTTAAA | GGAGCCAGCT | 3240
| CAAGCAATAT | TAATGAAGTA | GGTTCCAGTA | CTAATGAAGT | GGGCTCCAGT | ATTAATGAAA | 3300
| TAGGTTCCAG | TGATGAAAAC | ATTCAAGCAG | AACTAGGTAG | AAACAGAGGG | CCAAAATTGA | 3360
| ATGCTATGCT | TAGATTAGGG | GTTTTGCAAC | CTGAGGTCTA | TAAACAAAGT | CTTCCTGGAA | 3420
| GTAATTGTAA | GCATCCTGAA | ATAAAAAGC | AAGAATATGA | AGAAGTAGTT | CAGACTGTTA | 3480
| ATACAGATTT | CTCTCCATAT | CTGATTTCAG | ATAACTTAGA | ACAGCCTATG | GAAGTAGTC | 3540
| ATGCATCTCA | GGTTTGTTCT | GAGACACCTG | ATGACCTGTT | AGATGATGGT | GAAATAAAGG | 3600
| AAGATACTAG | TTTTGCTGAA | AATGACATTA | AGGAAAGTTC | TGCTGTTTTT | AGCAAAAGCG | 3660
| TCCAGAGAGG | AGAGCTTAGC | AGGAGTCCTA | GCCCTTTCAC | CCATACACAT | TTGGCTCAGG | 3720
| GTTACCGAAG | AGGGGCCAAG | AAATTAGAGT | CCTCAGAAGA | GAACTTATCT | AGTGAGGATG | 3780
| AAGAGCTTCC | CTGCTTCCAA | CACTTGTTAT | TTGGTAAAGT | AAACAATATA | CCTTCTCAGT | 3840
| CTACTAGGCA | TAGCACCGTT | GCTACCGAGT | GTCTGTCTAA | GAACACAGAG | GAGAATTTAT | 3900
| TATCATTGAA | GAATAGCTTA | AATGACTGCA | GTAACCAGGT | AATATTGGCA | AAGGCATCTC | 3960
| AGGAACATCA | CCTTAGTGAG | GAAACAAAAT | GTTCTGCTAG | CTTGTTTCT | TCACAGTGCA | 4020
| GTGAATTGGA | AGACTTGACT | GCAAATACAA | ACACCCAGGA | TCCTTTCTTG | ATTGGTTCTT | 4080
| CCAAACAAAT | GAGGCATCAG | TCTGAAAGCC | AGGGAGTTGG | TCTGAGTGAC | AAGGAATTGG | 4140
| TTTCAGATGA | TGAAGAAAGA | GGAACGGGCT | TGGAAGAAAA | TAATCAAGAA | GAGCAAAGCA | 4200
| TGGATTCAAA | CTTAGGTGAA | GCAGCATCTG | GGTGTGAGAG | TGAAACAAGC | GTCTCTGAAG | 4260
| ACTGCTCAGG | GCTATCCTCT | CAGAGTGACA | TTTTAACCAC | TCAGCAGAGG | GATACCATGC | 4320
| AACATAACCT | GATAAAGCTC | CAGCAGGAAA | TGGCTGAACT | AGAAGCTGTG | TTAGAACAGC | 4380
| ATGGGAGCCA | GCCTTCTAAC | AGCTACCCTT | CCATCATAAG | TGACTCTTCT | GCCCTTGAGG | 4440
| ACCTGCGAAA | TCCAGAACAA | AGCACATCAG | AAAAAGCAGT | ATTAACTTCA | CAGAAAAGTA | 4500
| GTGAATACCC | TATAAGCCAG | AATCCAGAAG | GCCTTTCTGC | TGACAAGTTT | GAGGTGTCTG | 4560
| CAGATAGTTC | TACCAGTAAA | AATAAAGAAC | CAGGAGTGGA | AAGGTCATCC | CCTTCTAAAT | 4620
| GCCCATCATT | AGATGATAGG | TGGTACATGC | ACAGTTGCTC | TGGGAGTCTT | CAGAATAGAA | 4680
| ACTACCCATC | TCAAGAGGAG | CTCATTAAGG | TTGTTGATGT | GGAGGAGCAA | CAGCTGGAAG | 4740
| AGTCTGGGCC | ACACGATTTG | ACGGAAACAT | CTTACTTGCC | AAGGCAAGAT | CTAGAGGGAA | 4800
| CCCCTTACCT | GGAATCTGGA | ATCAGCCTCT | TCTCTGATGA | CCCTGAATCT | GATCCTTCTG | 4860
| AAGACAGAGC | CCCAGAGTCA | GCTCGTGTTG | GCAACATACC | ATCTTCAACC | TCTGCATTGA | 4920
| AAGTTCCCCA | ATTGAAAGTT | GCAGAATCTG | CCCAGGGTCC | AGCTGCTGCT | CATACTACTG | 4980
| ATACTGCTGG | GTATAATGCA | ATGGAAGAAA | GTGTGAGCAG | GGAGAAGCCA | GAATTGACAG | 5040
| CTTCAACAGA | AAGGGTCAAC | AAAAGAATGT | CCATGGTGGT | GTCTGGCCTG | ACCCCAGAAG | 5100
| AATTTATGCT | CGTGTACAAG | TTTGCCAGAA | ACACCACAT | CACTTTAACT | AATCTAATTA | 5160
| CTGAAGAGAC | TACTCATGTT | GTTATGAAAA | CAGATGCTGA | GTTTGTGTGT | GAACGGACAC | 5220
| TGAAATATTT | TCTAGGAATT | GCGGGAGGAA | AATGGGTAGT | TAGCTATTTC | TGGGTGACCC | 5280
| AGTCTATTAA | AGAAGAAAA | ATGCTGAATG | AGCATGATTT | TGAAGTCAGA | GGAGATGTGG | 5340
| TCAATGGAAG | AAACCACCAA | GGTCCAAAGC | GAGCAAGAGA | ATCCCAGGAC | AGAAAGATCT | 5400
| TCAGGGGGCT | AGAAATCTGT | TGCTATGGGC | CCTTCACCAA | CATGCCCACA | GATCAACTGG | 5460
| AATGGATGGT | ACAGCTGTGT | GGTGCTTCTG | TGGTGAAGGA | GCTTTCATCA | TTCACCCTTG | 5520

```
GCACAGGTGT CCACCCAATT GTGGTTGTGC AGCCAGATGC CTGGACAGAG GACAATGGCT    5580

TCCATGCAAT TGGGCAGATG TGTGAGGCAC CTGTGGTGAC CCGAGAGTGG GTGTTGGACA    5640

GTGTAGCACT CTACCAGTGC CAGGAGCTGG ACACCTACCT GATACCCCAG ATCCCCCACA    5700

GCCACTACTG A                                                         5711
```

( 2 ) INFORMATION FOR SEQ ID NO:6:

( i ) SEQUENCE CHARACTERISTICS:
        ( A ) LENGTH: 1863 amino acids
        ( B ) TYPE: amino acid
        ( C ) STRANDEDNESS: Not Relevant
        ( D ) TOPOLOGY: Not Relevant ( i i ) MOLECULE TYPE: protein ( v i ) ORIGINAL SOURCE:
        ( A ) ORGANISM: Homo sapiens
        ( B ) STRAIN: BRCA1

( v i i i ) POSITION IN GENOME:
        ( A ) CHROMOSOME/SEGMENT: 17
        ( B ) MAP POSITION: 17q21

( x i ) SEQUENCE DESCRIPTION: SEQ ID NO:6:

```
Met Asp Leu Ser Ala Leu Arg Val Glu Glu Val Gln Asn Val Ile Asn
 1               5                  10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
 50                  55                  60

Lys Asn Asp Ile Thr Lys Arg Ser Leu Gln Glu Ser Thr Arg Phe Ser
 65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270
```

-continued

| | | | | | | | | | | | | | | |
|---|---|---|---|---|---|---|---|---|---|---|---|---|---|---|
|Pro|Cys|Gly|Thr|Asn|Thr|His|Ala|Ser|Ser|Leu|Gln|His|Glu|Asn|Ser|
| | |275| | | | |280| | | |285| | | | |
|Ser|Leu|Leu|Leu|Thr|Lys|Asp|Arg|Met|Asn|Val|Glu|Lys|Ala|Glu|Phe|
| |290| | | | |295| | | |300| | | | | |
|Cys|Asn|Lys|Ser|Lys|Gln|Pro|Gly|Leu|Ala|Arg|Ser|Gln|His|Asn|Arg|
|305| | | | |310| | | |315| | | | | |320|
|Trp|Ala|Gly|Ser|Lys|Glu|Thr|Cys|Asn|Asp|Arg|Arg|Thr|Pro|Ser|Thr|
| | | | |325| | | |330| | | | |335| | |
|Glu|Lys|Lys|Val|Asp|Leu|Asn|Ala|Asp|Pro|Leu|Cys|Glu|Arg|Lys|Glu|
| | | |340| | | | |345| | | |350| | | |
|Trp|Asn|Lys|Gln|Lys|Leu|Pro|Cys|Ser|Glu|Asn|Pro|Arg|Asp|Thr|Glu|
| | |355| | | | |360| | | |365| | | | |
|Asp|Val|Pro|Trp|Ile|Thr|Leu|Asn|Ser|Ser|Ile|Gln|Lys|Val|Asn|Glu|
| |370| | | | |375| | | |380| | | | | |
|Trp|Phe|Ser|Arg|Ser|Asp|Glu|Leu|Leu|Gly|Ser|Asp|Asp|Ser|His|Asp|
|385| | | | |390| | | |395| | | | | |400|
|Gly|Glu|Ser|Glu|Ser|Asn|Ala|Lys|Val|Ala|Asp|Val|Leu|Asp|Val|Leu|
| | | | |405| | | |410| | | |415| | | |
|Asn|Glu|Val|Asp|Glu|Tyr|Ser|Gly|Ser|Ser|Glu|Lys|Ile|Asp|Leu|Leu|
| | | |420| | | | |425| | | |430| | | |
|Ala|Ser|Asp|Pro|His|Glu|Ala|Leu|Ile|Cys|Lys|Ser|Glu|Arg|Val|His|
| | |435| | | | |440| | | |445| | | | |
|Ser|Lys|Ser|Val|Glu|Ser|Asn|Ile|Glu|Asp|Lys|Ile|Phe|Gly|Lys|Thr|
| |450| | | | |455| | | |460| | | | | |
|Tyr|Arg|Lys|Lys|Ala|Ser|Leu|Pro|Asn|Leu|Ser|His|Val|Thr|Glu|Asn|
|465| | | | |470| | | |475| | | | | |480|
|Leu|Ile|Ile|Gly|Ala|Phe|Val|Thr|Glu|Pro|Gln|Ile|Ile|Gln|Glu|Arg|
| | | | |485| | | |490| | | |495| | | |
|Pro|Leu|Thr|Asn|Lys|Leu|Lys|Arg|Lys|Arg|Arg|Pro|Thr|Ser|Gly|Leu|
| | | |500| | | |505| | | |510| | | | |
|His|Pro|Glu|Asp|Phe|Ile|Lys|Lys|Ala|Asp|Leu|Ala|Val|Gln|Lys|Thr|
| | |515| | | | |520| | | |525| | | | |
|Pro|Glu|Met|Ile|Asn|Gln|Gly|Thr|Asn|Gln|Thr|Glu|Gln|Asn|Gly|Gln|
| |530| | | | |535| | | |540| | | | | |
|Val|Met|Asn|Ile|Thr|Asn|Ser|Gly|His|Glu|Asn|Lys|Thr|Lys|Gly|Asp|
|545| | | | |550| | | |555| | | | | |560|
|Ser|Ile|Gln|Asn|Glu|Lys|Asn|Pro|Asn|Pro|Ile|Glu|Ser|Leu|Glu|Lys|
| | | | |565| | | |570| | | |575| | | |
|Glu|Ser|Ala|Phe|Lys|Thr|Lys|Ala|Glu|Pro|Ile|Ser|Ser|Ser|Ile|Ser|
| | | |580| | | |585| | | |590| | | | |
|Asn|Met|Glu|Leu|Glu|Leu|Asn|Ile|His|Asn|Ser|Lys|Ala|Pro|Lys|Lys|
| | |595| | | | |600| | | |605| | | | |
|Asn|Arg|Leu|Arg|Arg|Lys|Ser|Ser|Thr|Arg|His|Ile|His|Ala|Leu|Glu|
| |610| | | | |615| | | |620| | | | | |
|Leu|Val|Val|Ser|Arg|Asn|Leu|Ser|Pro|Pro|Asn|Cys|Thr|Glu|Leu|Gln|
|625| | | | |630| | | |635| | | | | |640|
|Ile|Asp|Ser|Cys|Ser|Ser|Ser|Glu|Glu|Ile|Lys|Lys|Lys|Lys|Tyr|Asn|
| | | |645| | | |650| | | |655| | | | |
|Gln|Met|Pro|Val|Arg|His|Ser|Arg|Asn|Leu|Gln|Leu|Met|Glu|Gly|Lys|
| | |660| | | | |665| | | |670| | | | |
|Glu|Pro|Ala|Thr|Gly|Ala|Lys|Lys|Ser|Asn|Lys|Pro|Asn|Glu|Gln|Thr|
| | |675| | | | |680| | | |685| | | | |
|Ser|Lys|Arg|His|Asp|Ser|Asp|Thr|Phe|Pro|Glu|Leu|Lys|Leu|Thr|Asn|
| |690| | | | |695| | | |700| | | | | |

```
Ala Pro Gly Ser Phe Thr Lys Cys Ser Asn Thr Ser Glu Leu Lys Glu
705                 710                 715                 720
Phe Val Asn Pro Ser Leu Pro Arg Glu Glu Lys Glu Glu Lys Leu Glu
                725                 730                 735
Thr Val Lys Val Ser Asn Asn Ala Glu Asp Pro Lys Asp Leu Met Leu
            740                 745                 750
Ser Gly Glu Arg Val Leu Gln Thr Glu Arg Ser Val Glu Ser Ser Ser
        755                 760                 765
Ile Ser Leu Val Pro Gly Thr Asp Tyr Gly Thr Gln Glu Ser Ile Ser
    770                 775                 780
Leu Leu Glu Val Ser Thr Leu Gly Lys Ala Lys Thr Glu Pro Asn Lys
785                 790                 795                 800
Cys Val Ser Gln Cys Ala Ala Phe Glu Asn Pro Lys Gly Leu Ile His
                805                 810                 815
Gly Cys Ser Lys Asp Asn Arg Asn Asp Thr Glu Gly Phe Lys Tyr Pro
            820                 825                 830
Leu Gly His Glu Val Asn His Ser Arg Glu Thr Ser Ile Glu Met Glu
        835                 840                 845
Glu Ser Glu Leu Asp Ala Gln Tyr Leu Gln Asn Thr Phe Lys Val Ser
850                 855                 860
Lys Arg Gln Ser Phe Ala Leu Phe Ser Asn Pro Gly Asn Ala Glu Glu
865                 870                 875                 880
Glu Cys Ala Thr Phe Ser Ala His Ser Gly Ser Leu Lys Lys Gln Ser
                885                 890                 895
Pro Lys Val Thr Phe Glu Cys Glu Gln Lys Glu Glu Asn Gln Gly Lys
            900                 905                 910
Asn Glu Ser Asn Ile Lys Pro Val Gln Thr Val Asn Ile Thr Ala Gly
        915                 920                 925
Phe Pro Val Val Gly Gln Lys Asp Lys Pro Val Asp Asn Ala Lys Cys
930                 935                 940
Ser Ile Lys Gly Gly Ser Arg Phe Cys Leu Ser Ser Gln Phe Arg Gly
945                 950                 955                 960
Asn Glu Thr Gly Leu Ile Thr Pro Asn Lys His Gly Leu Leu Gln Asn
                965                 970                 975
Pro Tyr Arg Ile Pro Pro Leu Phe Pro Ile Lys Ser Phe Val Lys Thr
            980                 985                 990
Lys Cys Lys Lys Asn Leu Leu Glu Glu Asn Phe Glu Glu His Ser Met
        995                 1000                1005
Ser Pro Glu Arg Glu Met Gly Asn Glu Asn Ile Pro Ser Thr Val Ser
    1010                1015                1020
Thr Ile Ser Arg Asn Asn Ile Arg Glu Asn Val Phe Lys Gly Ala Ser
1025                1030                1035                1040
Ser Ser Asn Ile Asn Glu Val Gly Ser Ser Thr Asn Glu Val Gly Ser
                1045                1050                1055
Ser Ile Asn Glu Ile Gly Ser Ser Asp Glu Asn Ile Gln Ala Glu Leu
            1060                1065                1070
Gly Arg Asn Arg Gly Pro Lys Leu Asn Ala Met Leu Arg Leu Gly Val
        1075                1080                1085
Leu Gln Pro Glu Val Tyr Lys Gln Ser Leu Pro Gly Ser Asn Cys Lys
    1090                1095                1100
His Pro Glu Ile Lys Lys Gln Glu Tyr Glu Glu Val Val Gln Thr Val
1105                1110                1115                1120
Asn Thr Asp Phe Ser Pro Tyr Leu Ile Ser Asp Asn Leu Glu Gln Pro
```

```
                          1125                      1130                       1135
Met  Gly  Ser  Ser  His  Ala  Ser  Gln  Val  Cys  Ser  Glu  Thr  Pro  Asp  Asp
                1140                      1145                      1150
Leu  Leu  Asp  Asp  Gly  Glu  Ile  Lys  Glu  Asp  Thr  Ser  Phe  Ala  Glu  Asn
           1155                      1160                      1165
Asp  Ile  Lys  Glu  Ser  Ser  Ala  Val  Phe  Ser  Lys  Ser  Val  Gln  Arg  Gly
           1170                      1175                      1180
Glu  Leu  Ser  Arg  Ser  Pro  Ser  Pro  Phe  Thr  His  Thr  His  Leu  Ala  Gln
1185                     1190                      1195                      1200
Gly  Tyr  Arg  Arg  Gly  Ala  Lys  Lys  Leu  Glu  Ser  Ser  Glu  Glu  Asn  Leu
                1205                      1210                      1215
Ser  Ser  Glu  Asp  Glu  Glu  Leu  Pro  Cys  Phe  Gln  His  Leu  Leu  Phe  Gly
                1220                      1225                      1230
Lys  Val  Asn  Asn  Ile  Pro  Ser  Gln  Ser  Thr  Arg  His  Ser  Thr  Val  Ala
           1235                      1240                      1245
Thr  Glu  Cys  Leu  Ser  Lys  Asn  Thr  Glu  Glu  Asn  Leu  Leu  Ser  Leu  Lys
           1250                      1255                      1260
Asn  Ser  Leu  Asn  Asp  Cys  Ser  Asn  Gln  Val  Ile  Leu  Ala  Lys  Ala  Ser
1265                     1270                      1275                      1280
Gln  Glu  His  His  Leu  Ser  Glu  Glu  Thr  Lys  Cys  Ser  Ala  Ser  Leu  Phe
                1285                      1290                      1295
Ser  Ser  Gln  Cys  Ser  Glu  Leu  Glu  Asp  Leu  Thr  Ala  Asn  Thr  Asn  Thr
           1300                      1305                      1310
Gln  Asp  Pro  Phe  Leu  Ile  Gly  Ser  Ser  Lys  Gln  Met  Arg  His  Gln  Ser
           1315                      1320                      1325
Glu  Ser  Gln  Gly  Val  Gly  Leu  Ser  Asp  Lys  Glu  Leu  Val  Ser  Asp  Asp
           1330                      1335                      1340
Glu  Glu  Arg  Gly  Thr  Gly  Leu  Glu  Glu  Asn  Asn  Gln  Glu  Glu  Gln  Ser
1345                     1350                      1355                      1360
Met  Asp  Ser  Asn  Leu  Gly  Glu  Ala  Ala  Ser  Gly  Cys  Glu  Ser  Glu  Thr
                1365                      1370                      1375
Ser  Val  Ser  Glu  Asp  Cys  Ser  Gly  Leu  Ser  Ser  Gln  Ser  Asp  Ile  Leu
                1380                      1385                      1390
Thr  Thr  Gln  Gln  Arg  Asp  Thr  Met  Gln  His  Asn  Leu  Ile  Lys  Leu  Gln
                1395                      1400                      1405
Gln  Glu  Met  Ala  Glu  Leu  Glu  Ala  Val  Leu  Glu  Gln  His  Gly  Ser  Gln
1410                     1415                      1420
Pro  Ser  Asn  Ser  Tyr  Pro  Ser  Ile  Ile  Ser  Asp  Ser  Ser  Ala  Leu  Glu
1425                     1430                      1435                      1440
Asp  Leu  Arg  Asn  Pro  Glu  Gln  Ser  Thr  Ser  Glu  Lys  Ala  Val  Leu  Thr
                1445                      1450                      1455
Ser  Gln  Lys  Ser  Ser  Glu  Tyr  Pro  Ile  Ser  Gln  Asn  Pro  Glu  Gly  Leu
                1460                      1465                      1470
Ser  Ala  Asp  Lys  Phe  Glu  Val  Ser  Ala  Asp  Ser  Ser  Thr  Ser  Lys  Asn
           1475                      1480                      1485
Lys  Glu  Pro  Gly  Val  Glu  Arg  Ser  Ser  Pro  Ser  Lys  Cys  Pro  Ser  Leu
           1490                      1495                      1500
Asp  Asp  Arg  Trp  Tyr  Met  His  Ser  Cys  Ser  Gly  Ser  Leu  Gln  Asn  Arg
1505                     1510                      1515                      1520
Asn  Tyr  Pro  Ser  Gln  Glu  Glu  Leu  Ile  Lys  Val  Val  Asp  Val  Glu  Glu
                1525                      1530                      1535
Gln  Gln  Leu  Glu  Glu  Ser  Gly  Pro  His  Asp  Leu  Thr  Glu  Thr  Ser  Tyr
                1540                      1545                      1550
```

| | | | | | | | | | | | | |
|---|---|---|---|---|---|---|---|---|---|---|---|---|
|Leu|Pro|Arg|Gln|Asp|Leu|Glu|Gly|Thr|Pro|Tyr|Leu|Glu|Ser|Gly|Ile|
| |   |1555|   |   |   |1560|   |   |   |1565|   |   |

Leu Pro Arg Gln Asp Leu Glu Gly Thr Pro Tyr Leu Glu Ser Gly Ile
         1555                1560                1565

Ser Leu Phe Ser Asp Asp Pro Glu Ser Asp Pro Ser Glu Asp Arg Ala
         1570                1575                1580

Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Gly Pro Ala Ala
             1605                1610                1615

Ala His Thr Thr Asp Thr Ala Gly Tyr Asn Ala Met Glu Glu Ser Val
             1620                1625                1630

Ser Arg Glu Lys Pro Glu Leu Thr Ala Ser Thr Glu Arg Val Asn Ly
        1635                1640                1645

Arg Met Ser Met Val Val Ser Gly Leu Thr Pro Glu Glu Phe Met Leu
1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
             1685                1690                1695

Cys Glu Arg Thr Leu Lys Tyr Phe Leu Gly Ile Ala Gly Gly Lys Trp
             1700                1705                1710

Val Val Ser Tyr Phe Trp Val Thr Gln Ser Ile Lys Glu Arg Lys Met
         1715                1720                1725

Leu Asn Glu His Asp Phe Glu Val Arg Gly Asp Val Val Asn Gly Arg
             1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
             1765                1770                1775

Thr Asp Gln Leu Glu Trp Met Val Gln Leu Cys Gly Ala Ser Val Val
             1780                1785                1790

Lys Glu Leu Ser Ser Phe Thr Leu Gly Thr Gly Val His Pro Ile Val
         1795                1800                1805

Val Val Gln Pro Asp Ala Trp Thr Glu Asp Asn Gly Phe His Ala Ile
1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
             1845                1850                1855

Gln Ile Pro His Ser His Tyr
             1860

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 2F primer ( x i ) SEQUENCE DESCRIPTION: SEQ ID NO:7:

GAAGTTGTCA TTTTATAAAC CTTT        24

( 2 ) INFORMATION FOR SEQ ID NO:8:

( i ) SEQUENCE CHARACTERISTICS:
    ( A ) LENGTH: 22 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 2R primer ( x i ) SEQUENCE DESCRIPTION: SEQ ID NO:8:

TGTCTTTTCT TCCCTAGTAT GT　　　　　　　　　　　　　　　　　　　　　　　　　22

( 2 ) INFORMATION FOR SEQ ID NO:9:

( i ) SEQUENCE CHARACTERISTICS:
    ( A ) LENGTH: 21 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 3F primer ( x i ) SEQUENCE DESCRIPTION: SEQ ID NO:9:

TCCTGACACA GCAGACATTT A　　　　　　　　　　　　　　　　　　　　　　　　　21

( 2 ) INFORMATION FOR SEQ ID NO:10:

( i ) SEQUENCE CHARACTERISTICS:
    ( A ) LENGTH: 21 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 3R primer ( x i ) SEQUENCE DESCRIPTION: SEQ ID NO:10:

TTGGATTTTC GTTCTCACTT A　　　　　　　　　　　　　　　　　　　　　　　　　21

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 5F primer ( x i ) SEQUENCE DESCRIPTION: SEQ ID NO:11:

CTCTTAAGGG CAGTTGTGAG　　　　　　　　　　　　　　　　　　　　　　　　　　20

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

```
        ( v i ) ORIGINAL SOURCE:
                  ( B ) STRAIN: 5R-M13* primer ( x i ) SEQUENCE DESCRIPTION: SEQ ID NO:12:

TTCCTACTGT GGTTGCTTCC                                                                    20

( 2 ) INFORMATION FOR SEQ ID NO:13:

( i ) SEQUENCE CHARACTERISTICS:
                  ( A ) LENGTH: 23 base pairs
                  ( B ) TYPE: nucleic acid
                  ( C ) STRANDEDNESS: Not Relevant
                  ( D ) TOPOLOGY: linear ( i i ) MOLECULE TYPE: DNA (genomic)

( v i ) ORIGINAL SOURCE:
                  ( B ) STRAIN: 6/7F primer ( x i ) SEQUENCE DESCRIPTION: SEQ ID NO:13:

CTTATTTTAG TGTCCTTAAA AGG                                                                23

( 2 ) INFORMATION FOR SEQ ID NO:14:

( i ) SEQUENCE CHARACTERISTICS:
                  ( A ) LENGTH: 22 base pairs
                  ( B ) TYPE: nucleic acid
                  ( C ) STRANDEDNESS: Not Relevant
                  ( D ) TOPOLOGY: linear ( i i ) MOLECULE TYPE: DNA (genomic)

( v i ) ORIGINAL SOURCE:
                  ( B ) STRAIN: 6R ( x i ) SEQUENCE DESCRIPTION: SEQ ID NO:14:

TTTCATGGAC AGCACTTGAG TG                                                                 22

( 2 ) INFORMATION FOR SEQ ID NO:15:

( i ) SEQUENCE CHARACTERISTICS:
                  ( A ) LENGTH: 23 base pairs
                  ( B ) TYPE: nucleic acid
                  ( C ) STRANDEDNESS: Not Relevant
                  ( D ) TOPOLOGY: linear ( i i ) MOLECULE TYPE: DNA (genomic)

( v i ) ORIGINAL SOURCE:
                  ( B ) STRAIN: 7F primer ( x i ) SEQUENCE DESCRIPTION: SEQ ID NO:15:

CACAACAAAG AGCATACATA GGG                                                                23

( 2 ) INFORMATION FOR SEQ ID NO:16:

( i ) SEQUENCE CHARACTERISTICS:
                  ( A ) LENGTH: 20 base pairs
                  ( B ) TYPE: nucleic acid
                  ( C ) STRANDEDNESS: Not Relevant
                  ( D ) TOPOLOGY: linear ( i i ) MOLECULE TYPE: DNA (genomic)

( v i ) ORIGINAL SOURCE:
                  ( B ) STRAIN: 6/7R primer ( x i ) SEQUENCE DESCRIPTION: SEQ ID NO:16:

TCGGGTTCAC TCTGTAGAAG                                                                    20
```

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 8F1 primer ( x i ) SEQUENCE DESCRIPTION: SEQ ID NO:17:

TTCTCTTCAG GAGGAAAAGC A                                         21

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 8R1 primer ( x i ) SEQUENCE DESCRIPTION: SEQ ID NO:18:

GCTGCCTACC ACAAATACAA A                                         21

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 9F primer ( x i ) SEQUENCE DESCRIPTION: SEQ ID NO:19:

CCACAGTAGA TGCTCAGTAA ATA                                       23

( 2 ) INFORMATION FOR SEQ ID NO:20:

( i ) SEQUENCE CHARACTERISTICS:
        ( A ) LENGTH: 23 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 9R primer ( x i ) SEQUENCE DESCRIPTION: SEQ ID NO:20:

TAGGAAAATA CCAGCTTCAT AGA                                       23

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
    ( B ) STRAIN: 10F primer ( x i ) SEQUENCE DESCRIPTION: SEQ ID NO:21:

TGGTCAGCTT TCTGTAATCG     20

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 10R primer ( x i ) SEQUENCE DESCRIPTION: SEQ ID NO:22:

GTATCTACCC ACTCTCTTCT TCAG     24

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11AF primer ( x i ) SEQUENCE DESCRIPTION: SEQ ID NO:23:

CCACCTCCAA GGTGTATCA     19

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11AR primer ( x i ) SEQUENCE DESCRIPTION: SEQ ID NO:24:

TGTTATGTTG GCTCCTTGCT     20

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11BF1 primer ( x i ) SEQUENCE DESCRIPTION: SEQ ID NO:25:

```
CACTAAAGAC AGAATGAATC TA                                                        22
```

( 2 ) INFORMATION FOR SEQ ID NO:26:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11BR1 primer ( x i ) SEQUENCE DESCRIPTION: SEQ ID NO:26:

```
GAAGAACCAG AATATTCATC TA                                                        22
```

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11CF1 primer ( x i ) SEQUENCE DESCRIPTION: SEQ ID NO:27:

```
TGATGGGGAG TCTGAATCAA                                                           20
```

( 2 ) INFORMATION FOR SEQ ID NO:28:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11CR1 primer ( x i ) SEQUENCE DESCRIPTION: SEQ ID NO:28:

```
TCTGCTTTCT TGATAAAATC CT                                                        22
```

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11DF1 primer ( x i ) SEQUENCE DESCRIPTION: SEQ ID NO:29:

```
AGCGTCCCCT CACAAATAAA                                                           20
```

( 2 ) INFORMATION FOR SEQ ID NO:30:

( i ) SEQUENCE CHARACTERISTICS:
        ( A ) LENGTH: 20 base pairs
        ( B ) TYPE: nucleic acid ( C ) STRANDEDNESS: Not Relevant
( D ) TOPOLOGY: linear ( i i ) MOLECULE TYPE: DNA (genomic)

( v i ) ORIGINAL SOURCE:
    ( B ) STRAIN: 11DR1 primer ( x i ) SEQUENCE DESCRIPTION: SEQ ID NO:30:

TCAAGCGCAT GAATATGCCT 20

( 2 ) INFORMATION FOR SEQ ID NO:31:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11EF primer ( x i ) SEQUENCE DESCRIPTION: SEQ ID NO:31:

GTATAAGCAA TATGGAACTC GA 22

( 2 ) INFORMATION FOR SEQ ID NO:32:

( i ) SEQUENCE CHARACTERISTICS:
        ( A ) LENGTH: 23 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11ER primer ( x i ) SEQUENCE DESCRIPTION: SEQ ID NO:32:

TTAAGTTCACT GGTATTTGAA CA 23

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11FF primer ( x i ) SEQUENCE DESCRIPTION: SEQ ID NO:33:

GACAGCGATA CTTTCCCAGA 20

( 2 ) INFORMATION FOR SEQ ID NO:34:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11FR primer ( x i ) SEQUENCE DESCRIPTION: SEQ ID NO:34:

TGGAACAACC ATGAATTAGT C                                                              2 1

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11GF primer ( x i ) SEQUENCE DESCRIPTION: SEQ ID NO:35:

GGAAGTTAGC ACTCTAGGGA                                                                2 0

( 2 ) INFORMATION FOR SEQ ID NO:36:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11GR primer ( x i ) SEQUENCE DESCRIPTION: SEQ ID NO:36:

GCAGTGATAT TAACTGTCTG TA                                                             2 2

( 2 ) INFORMATION FOR SEQ ID NO:37:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11HF primer ( x i ) SEQUENCE DESCRIPTION: SEQ ID NO:37:

TGGGTCCTTA AAGAAACAAA GT                                                             2 2

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11HR primer ( x i ) SEQUENCE DESCRIPTION: SEQ ID NO:38:

TCAGGTGACA TTGAATCTTC C                                                              2 1

( 2 ) INFORMATION FOR SEQ ID NO:39:

( i ) SEQUENCE CHARACTERISTICS:

(A) LENGTH: 21 base pairs
                (B) TYPE: nucleic acid
                (C) STRANDEDNESS: Not Relevant
                (D) TOPOLOGY: linear (ii) MOLECULE TYPE: DNA (genomic)

(vi) ORIGINAL SOURCE:
                (B) STRAIN: 11IF primer (xi) SEQUENCE DESCRIPTION: SEQ ID NO:39:

CCACTTTTTC CCATCAAGTC A                                                        21

(2) INFORMATION FOR SEQ ID NO:40:

(i) SEQUENCE CHARACTERISTICS:
                (A) LENGTH: 22 base pairs
                (B) TYPE: nucleic acid
                (C) STRANDEDNESS: Not Relevant
                (D) TOPOLOGY: linear (ii) MOLECULE TYPE: DNA (genomic)

(vi) ORIGINAL SOURCE:
                (B) STRAIN: 11IR primer (xi) SEQUENCE DESCRIPTION: SEQ ID NO:40:

TCAGGATGCT TACAATTACT TC                                                       22

(2) INFORMATION FOR SEQ ID NO:41:

(i) SEQUENCE CHARACTERISTICS:
                (A) LENGTH: 23 base pairs
                (B) TYPE: nucleic acid
                (C) STRANDEDNESS: Not Relevant
                (D) TOPOLOGY: linear (ii) MOLECULE TYPE: DNA (genomic)

(vi) ORIGINAL SOURCE:
                (B) STRAIN: 11JF primer (xi) SEQUENCE DESCRIPTION: SEQ ID NO:41:

CAAAATTGAA TGCTATGCTT AGA                                                      23

(2) INFORMATION FOR SEQ ID NO:42:

(i) SEQUENCE CHARACTERISTICS:
                (A) LENGTH: 20 base pairs
                (B) TYPE: nucleic acid
                (C) STRANDEDNESS: Not Relevant
                (D) TOPOLOGY: linear (ii) MOLECULE TYPE: DNA (genomic)

(vi) ORIGINAL SOURCE:
                (B) STRAIN: 11JR primer (xi) SEQUENCE DESCRIPTION: SEQ ID NO:42:

TCGGTAACCC TGAGCCAAAT                                                          20

(2) INFORMATION FOR SEQ ID NO:43:

(i) SEQUENCE CHARACTERISTICS:
                (A) LENGTH: 20 base pairs
                (B) TYPE: nucleic acid
                (C) STRANDEDNESS: Not Relevant
                (D) TOPOLOGY: linear (ii) MOLECULE TYPE: DNA (genomic)

(vi) ORIGINAL SOURCE:

( B ) STRAIN: 11KF primer ( x i ) SEQUENCE DESCRIPTION: SEQ ID NO:43:

GCAAAAGCGT CCAGAAAGGA 20

( 2 ) INFORMATION FOR SEQ ID NO:44:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11KR-1 primer ( x i ) SEQUENCE DESCRIPTION: SEQ ID NO:44:

TATTTGCAGT CAAGTCTTCC AA 22

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11LF-1 primer ( x i ) SEQUENCE DESCRIPTION: SEQ ID NO:45:

GTAATATTGG CAAAGGCATC T 21

( 2 ) INFORMATION FOR SEQ ID NO:46:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11LR primer ( x i ) SEQUENCE DESCRIPTION: SEQ ID NO:46:

TAAAATGTGC TCCCCAAAAG CA 22

( 2 ) INFORMATION FOR SEQ ID NO:47:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 12F primer ( x i ) SEQUENCE DESCRIPTION: SEQ ID NO:47:

GTCCTGCCAA TGAGAAGAAA 20

( 2 ) INFORMATION FOR SEQ ID NO:48:

( i ) SEQUENCE CHARACTERISTICS:
    ( A ) LENGTH: 21 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 12R primer ( x i ) SEQUENCE DESCRIPTION: SEQ ID NO:48:

TGTCAGCAAA CCTAAGAATG T                                21

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 13F primer ( x i ) SEQUENCE DESCRIPTION: SEQ ID NO:49:

AATGGAAAGC TTCTCAAAGT A                                21

( 2 ) INFORMATION FOR SEQ ID NO:50:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 13R primer ( x i ) SEQUENCE DESCRIPTION: SEQ ID NO:50:

ATGTTGGAGC TAGGTCCTTA C                                21

( 2 ) INFORMATION FOR SEQ ID NO:51:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 14F primer ( x i ) SEQUENCE DESCRIPTION: SEQ ID NO:51:

CTAACCTGAA TTATCACTAT CA                               22

( 2 ) INFORMATION FOR SEQ ID NO:52:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

(vi) ORIGINAL SOURCE:
        (B) STRAIN: 14R primer (xi) SEQUENCE DESCRIPTION: SEQ ID NO:52:

GTGTATAAAT GCCTGTATGC A                    21

(2) INFORMATION FOR SEQ ID NO:53:

(i) SEQUENCE CHARACTERISTICS:
        (A) LENGTH: 19 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 15F primer (xi) SEQUENCE DESCRIPTION: SEQ ID NO:53:

TGGCTGCCCA GGAAGTATG                       19

(2) INFORMATION FOR SEQ ID NO:54:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 15R primer (xi) SEQUENCE DESCRIPTION: SEQ ID NO:54:

AACCAGAATA TCTTTATGTA GGA                  23

(2) INFORMATION FOR SEQ ID NO:55:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 16F primer (xi) SEQUENCE DESCRIPTION: SEQ ID NO:55:

AATTCTTAAC AGAGACCAGA AC                   22

(2) INFORMATION FOR SEQ ID NO:56:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 16R primer (xi) SEQUENCE DESCRIPTION: SEQ ID NO:56:

AAAACTCTTT CCAGAATGTT GT                   22

( 2 ) INFORMATION FOR SEQ ID NO:57:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 17F primer ( x i ) SEQUENCE DESCRIPTION: SEQ ID NO:57:

GTGTAGAACG TGCAGGATTG                            20

( 2 ) INFORMATION FOR SEQ ID NO:58:

( i ) SEQUENCE CHARACTERISTICS:
        ( A ) LENGTH: 18 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 17R primer ( x i ) SEQUENCE DESCRIPTION: SEQ ID NO:58:

TCGCCTCATG TGGTTTTA                            18

( 2 ) INFORMATION FOR SEQ ID NO:59:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 18F primer ( x i ) SEQUENCE DESCRIPTION: SEQ ID NO:59:

GGCTCTTTAG CTTCTTAGGA C                        21

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 18R primer ( x i ) SEQUENCE DESCRIPTION: SEQ ID NO:60:

GAGACCATTT TCCCAGCATC                            20

( 2 ) INFORMATION FOR SEQ ID NO:61:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear (i i) MOLECULE TYPE: DNA (genomic)

(v i) ORIGINAL SOURCE:
    (B) STRAIN: 19F primer (x i) SEQUENCE DESCRIPTION: SEQ ID NO:61:

CTGTCATTCT TCCTGTGCTC  20

(2) INFORMATION FOR SEQ ID NO:62:

(i) SEQUENCE CHARACTERISTICS:
      (A) LENGTH: 21 base pairs
      (B) TYPE: nucleic acid
      (C) STRANDEDNESS: Not Relevant
      (D) TOPOLOGY: linear (i i) MOLECULE TYPE: DNA (genomic)

(v i) ORIGINAL SOURCE:
      (B) STRAIN: 19R primer (x i) SEQUENCE DESCRIPTION: SEQ ID NO:62:

CATTGTTAAG GAAAGTGGTG C  21

(2) INFORMATION FOR SEQ ID NO:63:

(i) SEQUENCE CHARACTERISTICS:
      (A) LENGTH: 20 base pairs
      (B) TYPE: nucleic acid
      (C) STRANDEDNESS: Not Relevant
      (D) TOPOLOGY: linear (i i) MOLECULE TYPE: DNA (genomic)

(v i) ORIGINAL SOURCE:
      (B) STRAIN: 20F primer (x i) SEQUENCE DESCRIPTION: SEQ ID NO:63:

ATATGACGTG TCTGCTCCAC  20

(2) INFORMATION FOR SEQ ID NO:64:

(i) SEQUENCE CHARACTERISTICS:
      (A) LENGTH: 20 base pairs
      (B) TYPE: nucleic acid
      (C) STRANDEDNESS: Not Relevant
      (D) TOPOLOGY: linear (i i) MOLECULE TYPE: DNA (genomic)

(v i) ORIGINAL SOURCE:
      (B) STRAIN: 20R primer (x i) SEQUENCE DESCRIPTION: SEQ ID NO:64:

GGGAATCCAA ATTACACAGC  20

(2) INFORMATION FOR SEQ ID NO:65:

(i) SEQUENCE CHARACTERISTICS:
      (A) LENGTH: 22 base pairs
      (B) TYPE: nucleic acid
      (C) STRANDEDNESS: Not Relevant
      (D) TOPOLOGY: linear (i i) MOLECULE TYPE: DNA (genomic)

(v i) ORIGINAL SOURCE:
      (B) STRAIN: 21F primer (x i) SEQUENCE DESCRIPTION: SEQ ID NO:65:

AAGCTCTTCC TTTTTGAAAG TC 22

( 2 ) INFORMATION FOR SEQ ID NO:66:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 21R primer ( x i ) SEQUENCE DESCRIPTION: SEQ ID NO:66:

GTAGAGAAAT AGAATAGCCT CT 22

( 2 ) INFORMATION FOR SEQ ID NO:67:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 22F primer ( x i ) SEQUENCE DESCRIPTION: SEQ ID NO:67:

TCCCATTGAG AGGTCTTGCT 20

( 2 ) INFORMATION FOR SEQ ID NO:68:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 22R primer ( x i ) SEQUENCE DESCRIPTION: SEQ ID NO:68:

GAGAAGACTT CTGAGGCTAC 20

( 2 ) INFORMATION FOR SEQ ID NO:69:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 23F-1 primer ( x i ) SEQUENCE DESCRIPTION: SEQ ID NO:69:

TGAAGTGACA GTTCCAGTAG T 21

( 2 ) INFORMATION FOR SEQ ID NO:70:

( i ) SEQUENCE CHARACTERISTICS:
        ( A ) LENGTH: 23 base pairs
        ( B ) TYPE: nucleic acid ( C ) STRANDEDNESS: Not Relevant
( D ) TOPOLOGY: linear ( i i ) MOLECULE TYPE: DNA (genomic)

( v i ) ORIGINAL SOURCE:
( B ) STRAIN: 23R-1 primer ( x i ) SEQUENCE DESCRIPTION: SEQ ID NO:70:

CATTTTAGCC ATTCATTCAA CAA 23

( 2 ) INFORMATION FOR SEQ ID NO:71:

( i ) SEQUENCE CHARACTERISTICS:
( A ) LENGTH: 22 base pairs
( B ) TYPE: nucleic acid
( C ) STRANDEDNESS: Not Relevant
( D ) TOPOLOGY: linear ( i i ) MOLECULE TYPE: DNA (genomic)

( v i ) ORIGINAL SOURCE:
( B ) STRAIN: 24F primer ( x i ) SEQUENCE DESCRIPTION: SEQ ID NO:71:

ATGAATTGAC ACTAATCTCT GC 22

( 2 ) INFORMATION FOR SEQ ID NO:72:

( i ) SEQUENCE CHARACTERISTICS:
( A ) LENGTH: 21 base pairs
( B ) TYPE: nucleic acid
( C ) STRANDEDNESS: Not Relevant
( D ) TOPOLOGY: linear ( i i ) MOLECULE TYPE: DNA (genomic)

( v i ) ORIGINAL SOURCE:
( B ) STRAIN: 24R primer ( x i ) SEQUENCE DESCRIPTION: SEQ ID NO:72:

GTAGCCAGGA CAGTAGAAGG A 21